(12) United States Patent
Gasiewski et al.

(10) Patent No.: US 12,140,551 B2
(45) Date of Patent: Nov. 12, 2024

(54) RADIOMETER AND RADIOMETER-BASED SOIL MOISTURE DETERMINATION METHOD

(71) Applicants: THE REGENTS OF THE UNIVERSITY OF COLORADO, Denver, CO (US); THE SOIL MOISTURE COMPANY, Boulder, CO (US)

(72) Inventors: Albin Gasiewski, Boulder, CO (US); Eryan Dai, Boulder, CO (US); Jack Elston, Boulder, CO (US); Maciej Stachura, Boulder, CO (US); Michael Hurowitz, Longmont, CO (US)

(73) Assignees: THE REGENTS OF THE UNIVERSITY OF COLORADO, A BODY CORPORATE, Denver, CO (US); THE SOIL MOISTURE COMPANY, Boulder, CO (US)

( * ) Notice: Subject to any disclaimer, the term of this patent is extended or adjusted under 35 U.S.C. 154(b) by 0 days.

(21) Appl. No.: 18/291,190

(22) PCT Filed: Jul. 25, 2022

(86) PCT No.: PCT/US2022/038241
§ 371 (c)(1),
(2) Date: Jan. 22, 2024

(87) PCT Pub. No.: WO2023/004202
PCT Pub. Date: Jan. 26, 2023

(65) Prior Publication Data
US 2024/0272091 A1     Aug. 15, 2024

Related U.S. Application Data

(60) Provisional application No. 63/225,422, filed on Jul. 23, 2021.

(51) Int. Cl.
*G01N 22/04* (2006.01)
*G01N 33/24* (2006.01)

(52) U.S. Cl.
CPC ........... *G01N 22/04* (2013.01); *G01N 33/246* (2013.01)

(58) Field of Classification Search
CPC ...... G01F 23/284; G01S 13/88; G01S 13/887; G01S 13/888; G01N 22/04; G01N 33/246
See application file for complete search history.

(56) References Cited

U.S. PATENT DOCUMENTS

| 4,873,481 A | 10/1989 | Nelson et al. |
| 5,526,676 A * | 6/1996 | Solheim ................. G01W 1/08 73/170.27 |

(Continued)

FOREIGN PATENT DOCUMENTS

CA        2916617 A1    1/2016

OTHER PUBLICATIONS

PCT/US2022/038241 International Search Report dated Oct. 14, 2022, 2 pages.

(Continued)

*Primary Examiner* — Peter M Bythrow
(74) *Attorney, Agent, or Firm* — Cozen O'Connor

(57) ABSTRACT

A method for determining soil moisture of a scene includes (i) generating a first antenna output in response to an upwelling thermal emission from the scene, (ii) generating a second antenna output in response to a downwelling thermal emission from sky above the scene, (iii) coupling the first antenna output and the second antenna output to yield a combined output having a quadrature phase difference between the first antenna output and the second antenna output, (iv) calculating a brightness-temperature difference based at least partially on the combined output, and (v)

(Continued)

calculating a soil moisture based on soil-vegetation radiative transfer model using the brightness-temperature difference.

16 Claims, 34 Drawing Sheets

(56)  References Cited

U.S. PATENT DOCUMENTS

| | | | |
|---|---|---|---|
| 5,777,481 A * | 7/1998 | Vivekanandan | G01N 22/04 |
| | | | 324/640 |
| 8,485,722 B1 | 7/2013 | Roeder et al. | |
| 2011/0307177 A1 * | 12/2011 | Hong | G01N 33/246 |
| | | | 702/2 |
| 2018/0180768 A1 * | 6/2018 | Wolf | G01W 1/12 |
| 2020/0292472 A1 | 9/2020 | Wolleben et al. | |
| 2021/0337721 A1 * | 11/2021 | Zhao | G01N 33/246 |
| 2022/0205930 A1 * | 6/2022 | Klein | G01V 3/17 |

OTHER PUBLICATIONS

PCT/US2022/038241 Written Opinion dated Oct. 14, 2022, 4 pages.
Schwank, M. et al. "ELBARA II, an L-Band Radiometer System for Soil Moisture Research", Sensors, vol. 10, No. 1, Jan. 13, 2009, pp. 584-612.

* cited by examiner

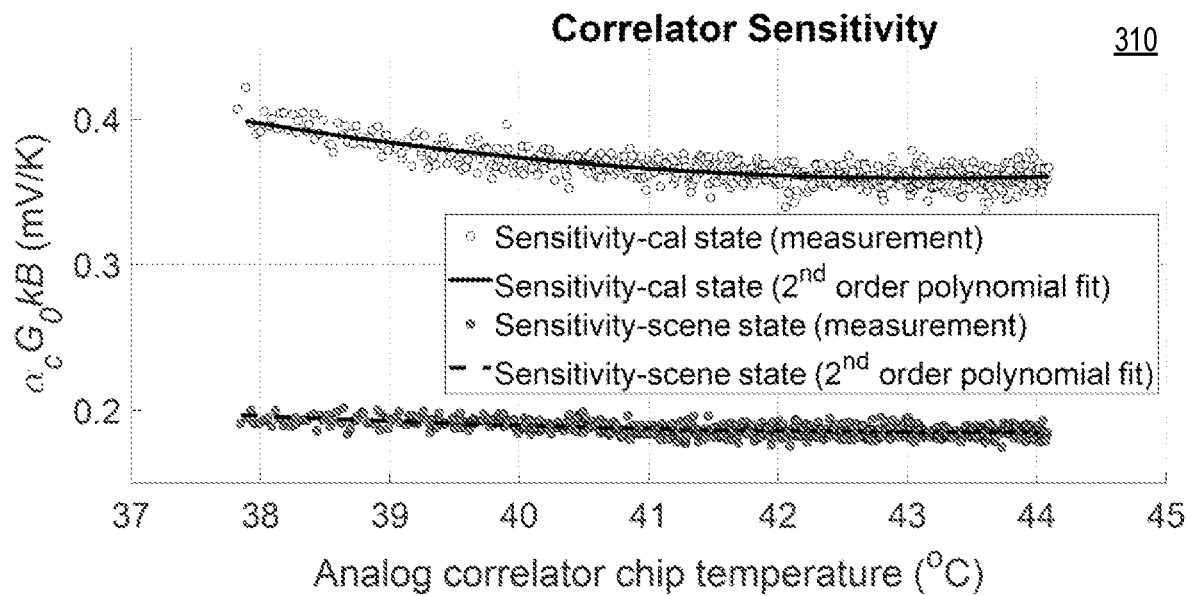
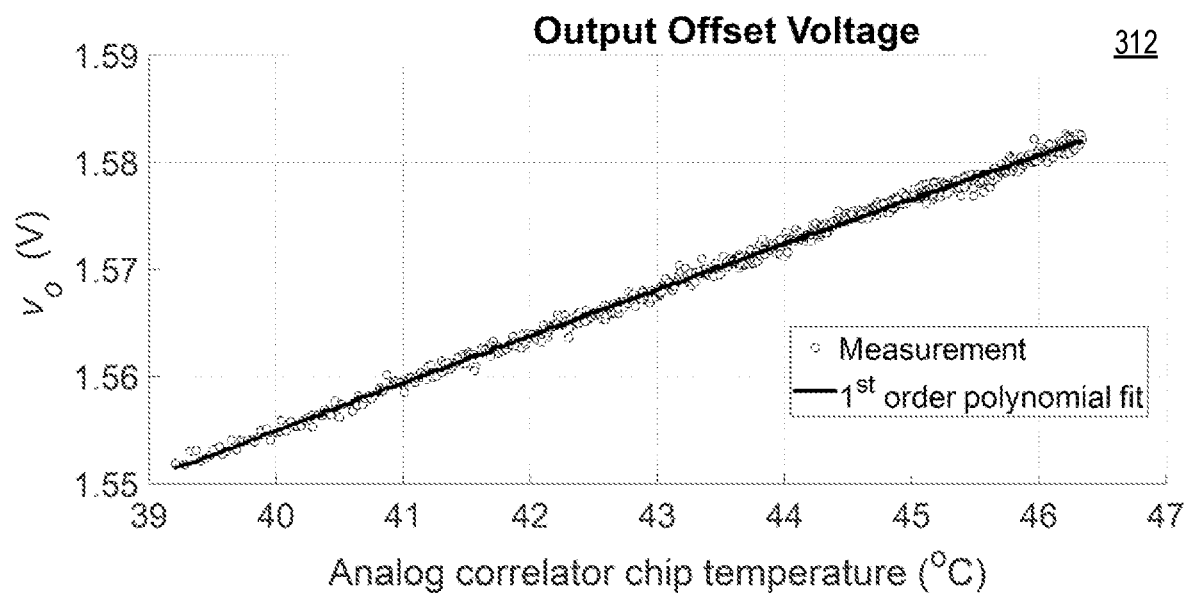
FIG. 3

| LDCR Rev A (analog correlator chip physical temperature of 316 K) | | | | | | |
|---|---|---|---|---|---|---|
| | Internal Source state | | | Scene state | | |
| Parameter | Pre-flight | In-flight | A-priori | Pre-flight | In-flight | A-priori |
| $\alpha_c G_o kB$ $\alpha_s G_o kB$ (mV/K) | 0.36 | 0.34 | 0.39 | 0.19 | 0.19 | 0.28 |
| $\sigma_{v_a}$ (mV) | 2.8 | 2.8 | 2.8 | 2.8 | 2.8 | 2.8 |
| $\Delta T_{RMS,c}$ $\Delta T_{RMS,s}$ (K) | 7.77 | 8.25 | 7.18 | 14.74 | 14.74 | 9.29 |

FIG. 4

| Land cover/vegetation type | $\omega_p$ | $b_h$ | $b_v$ | $h_R$ |
|---|---|---|---|---|
| Tall grass (Canton) | 0.05 | 0.57 | 0.43 | 0.156 |
| Short grass (IRF) | 0.05 | 0.13 | 0.13 | 0.156 |
| Corn | 0.10 | 0.18 | 0.20 | 0.094 |
| Wheat & grain sorghum | 0.00 | 0.10 | 0.30 | 0.083 |
| Soybean & sugar beets | 0.00 | 0.20 | 0.20 | 0.148 |
| Forest | 0.05 | 0.10 | 0.10 | 0.160 |
| Built | 0.4-0.95 | ∞ | ∞ | 0.000 |
| Bare Soil (road ways) | 0.00 | 0.00 | 0.00 | 0.150 |

FIG. 10

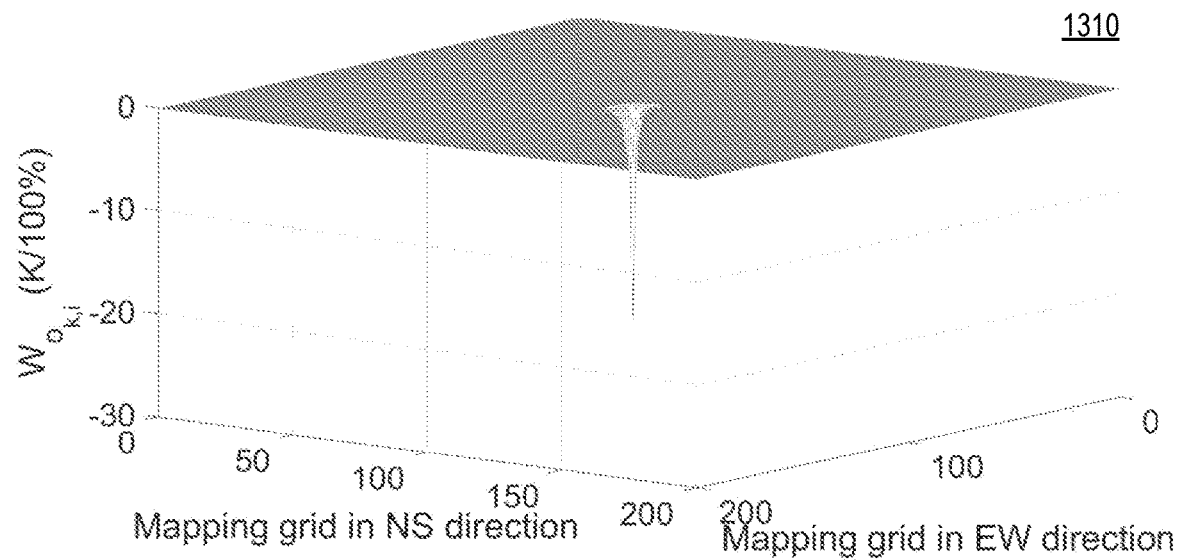
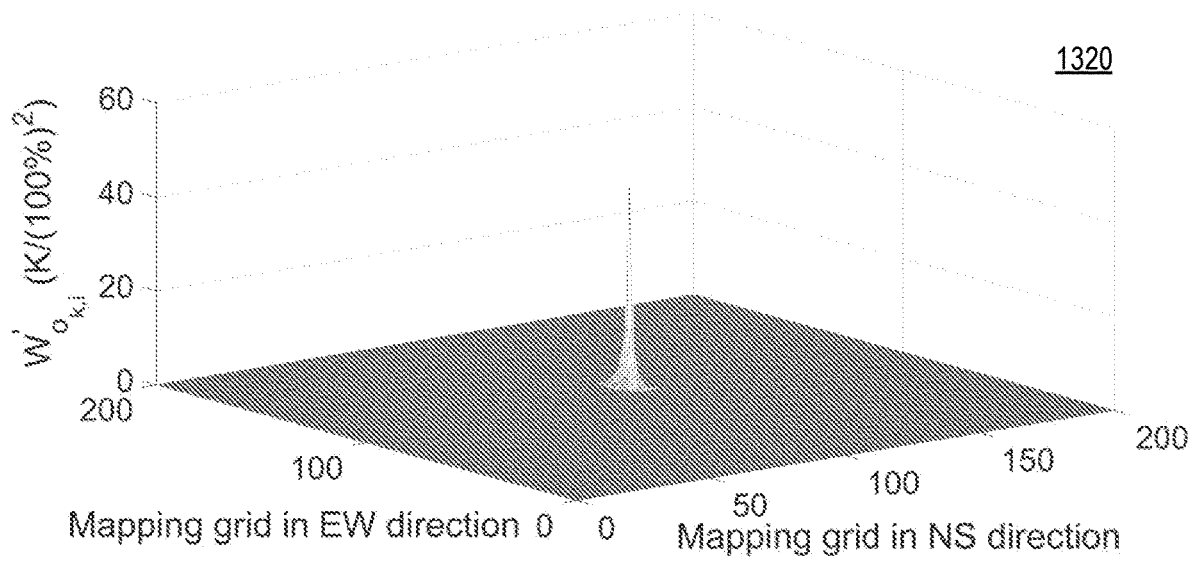
FIG. 13

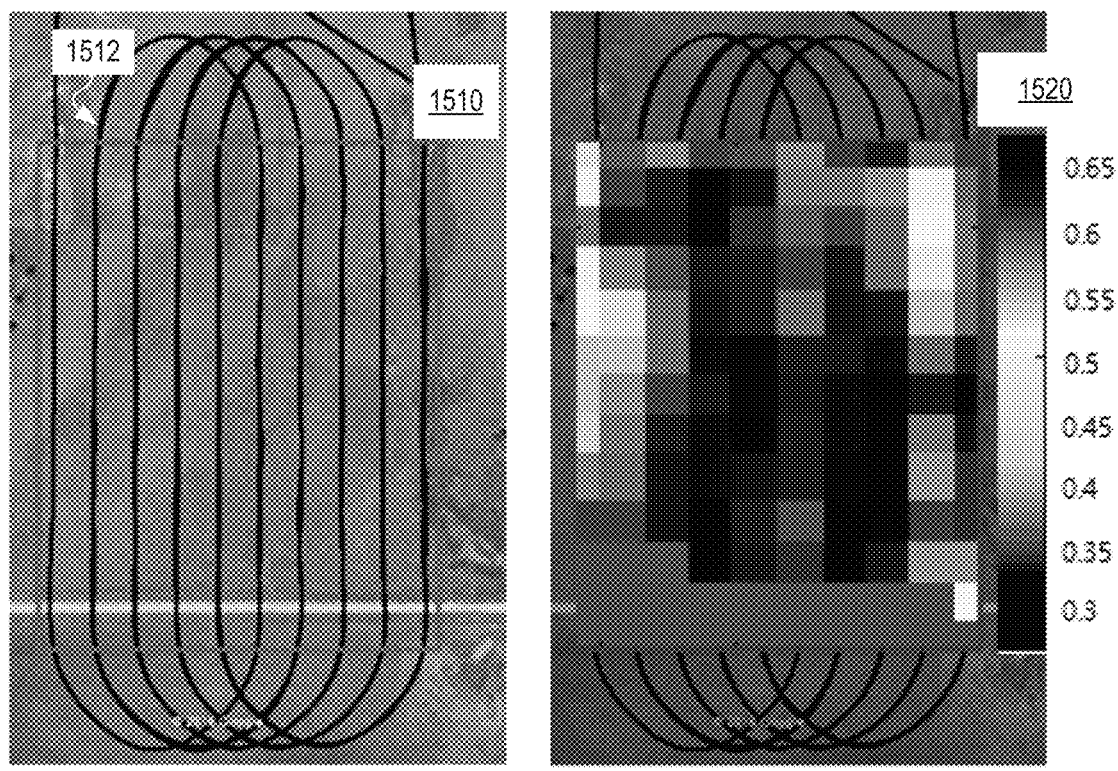
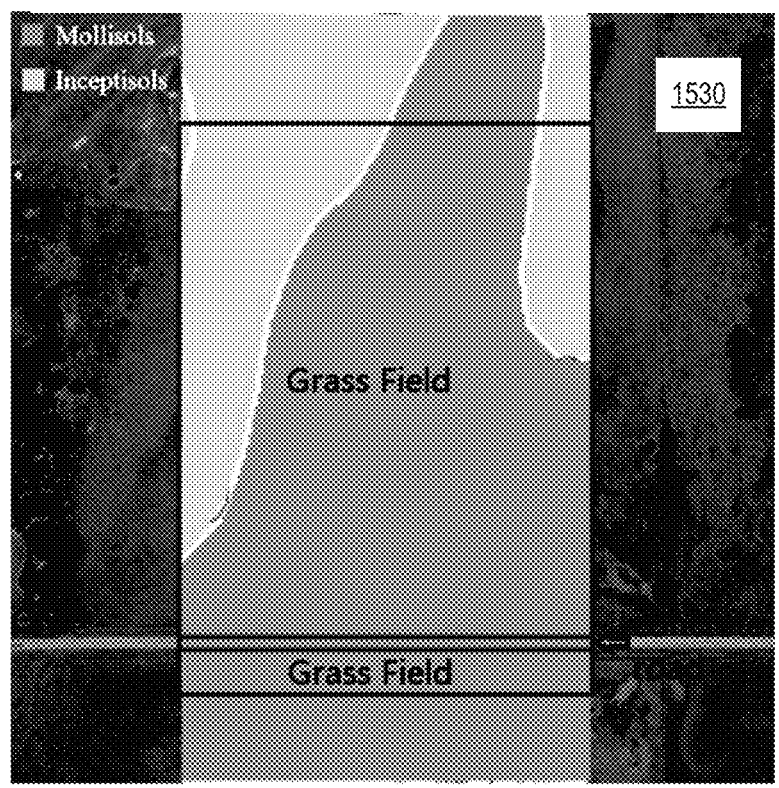
FIG. 15

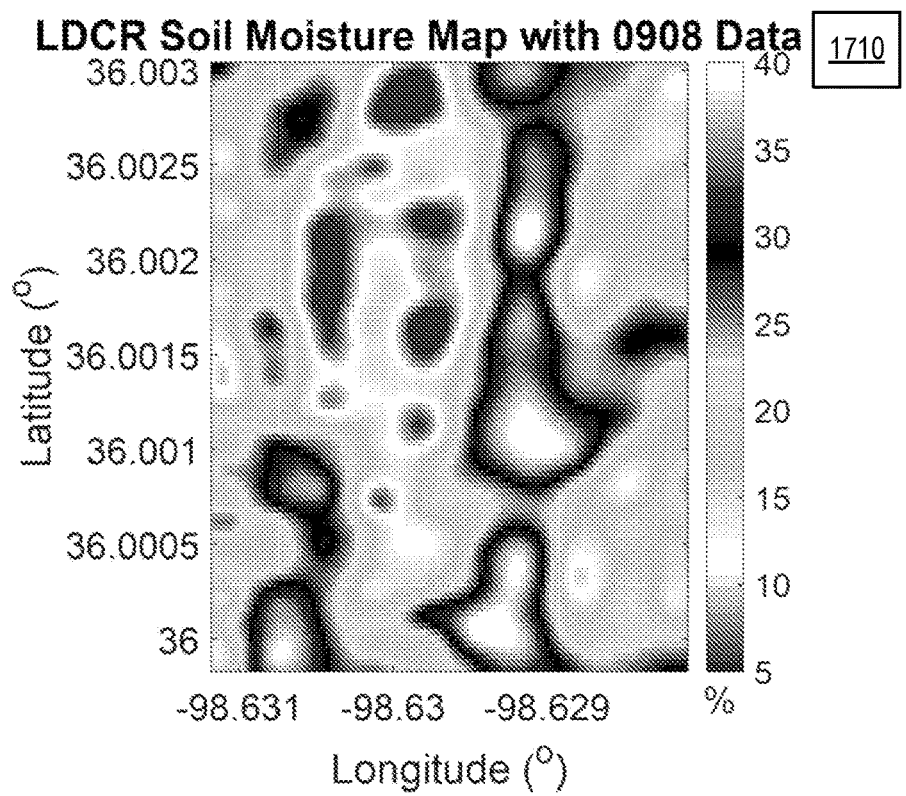
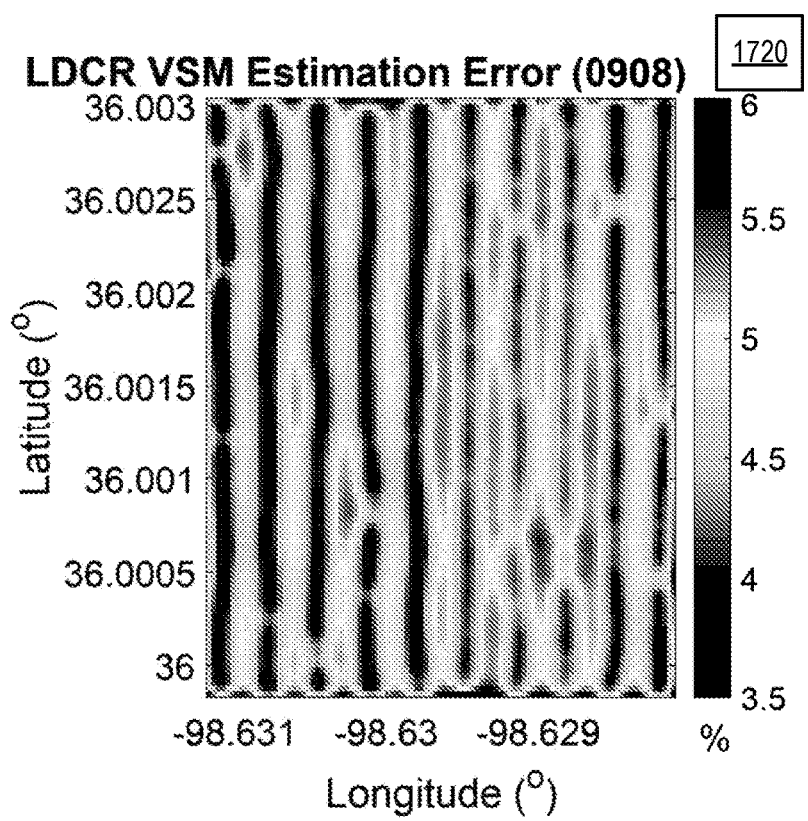
FIG. 17

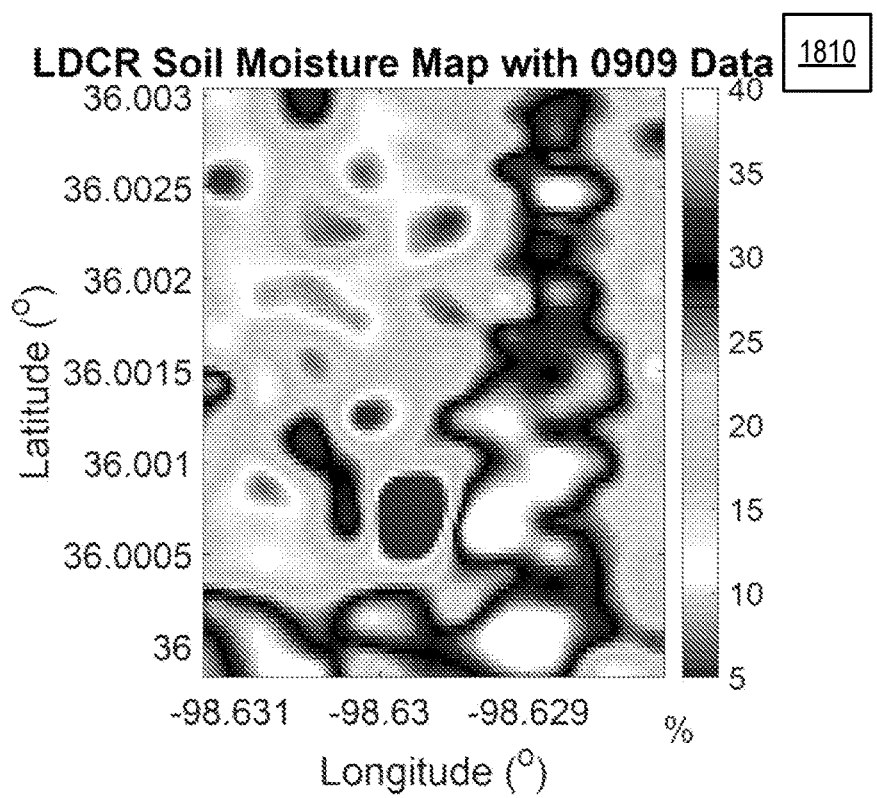
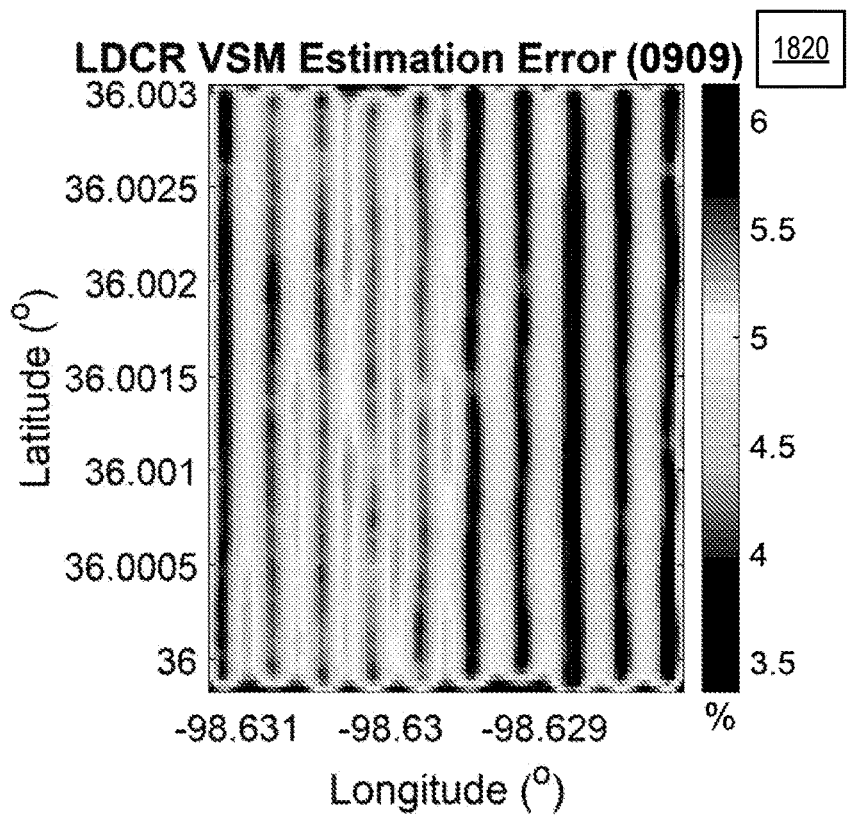
FIG. 18

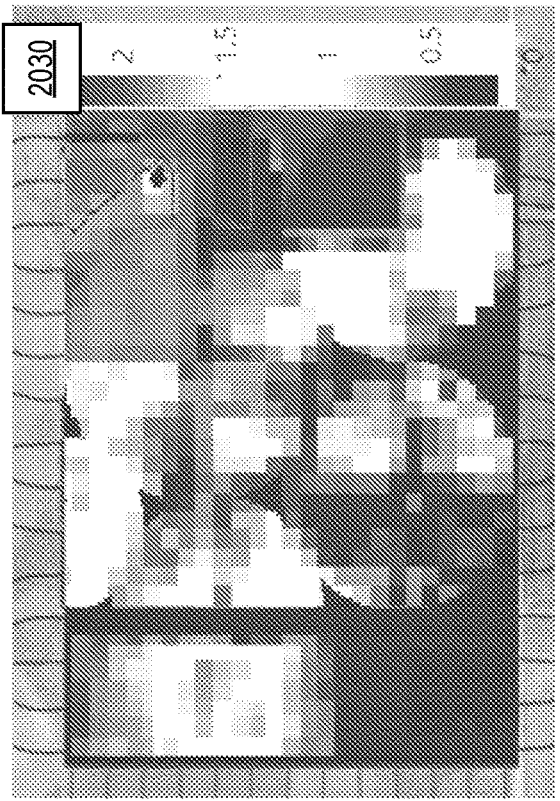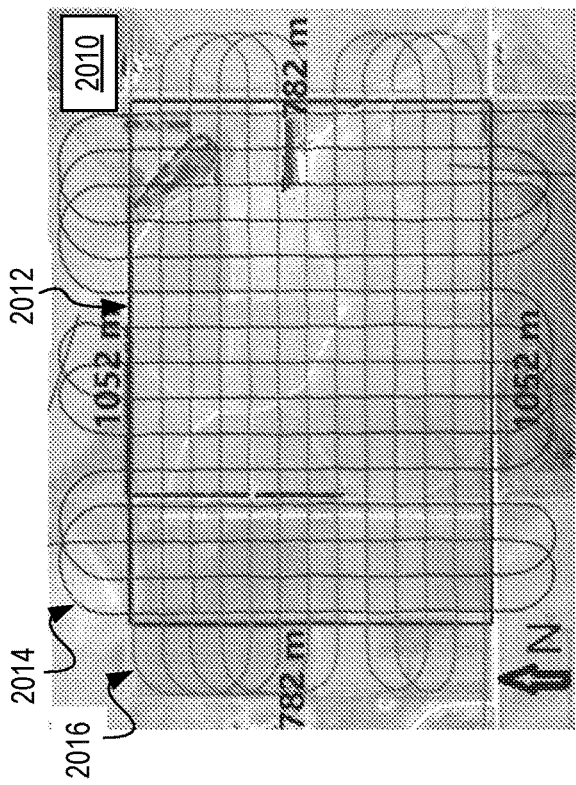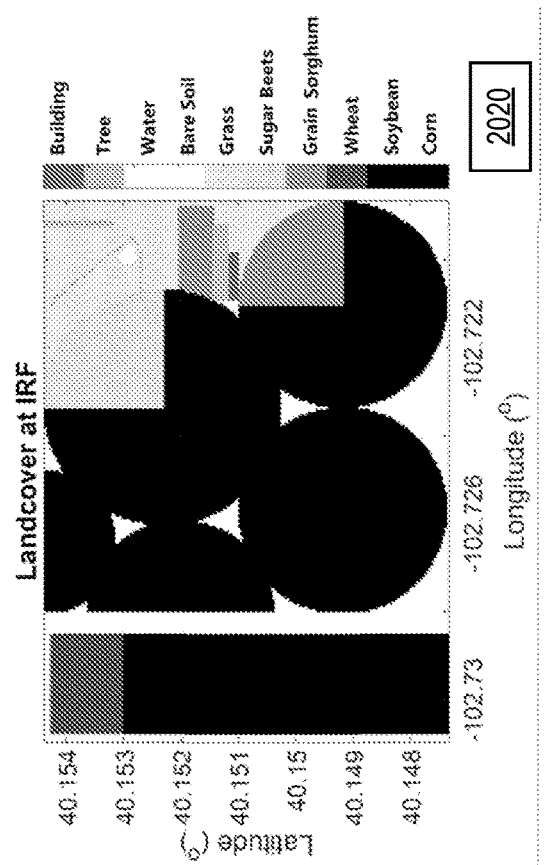
FIG. 20

| Soil Type | Description | Sand (%) | Clay (%) |
|---|---|---|---|
| 3 | Ascalon sandy loam, sandy substatu | 70 | 15 |
| 5 | Ascalon fine sandy loam | 70 | 15 |
| 19 | Haxtun sandy loam | 75 | 10 |
| 23 | Julesburg loamy sand | 75 | 10 |
| 37 | Rogo loam | 25 | 20 |

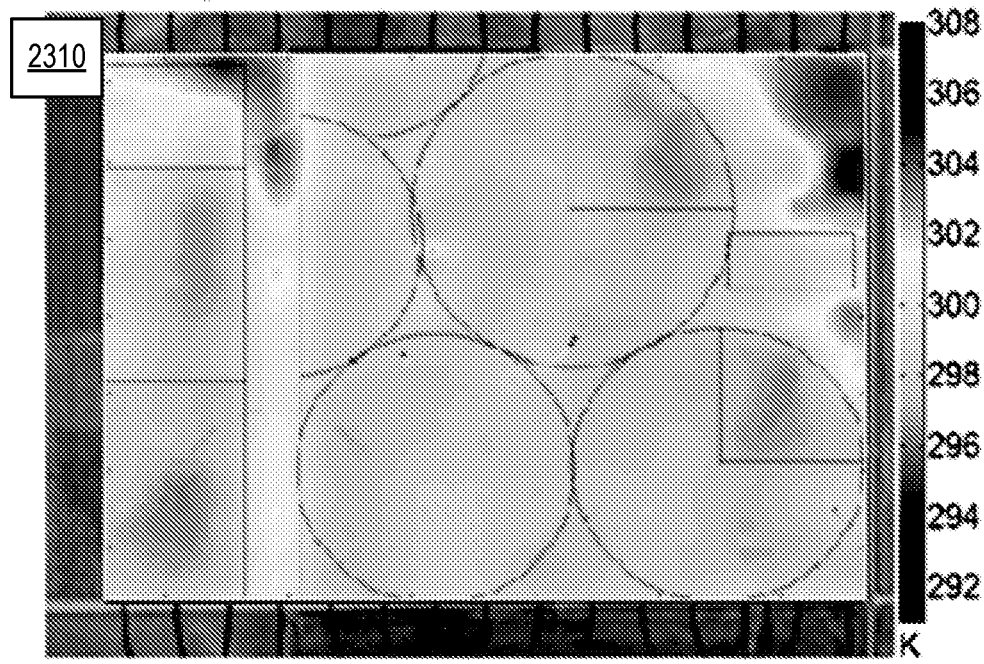
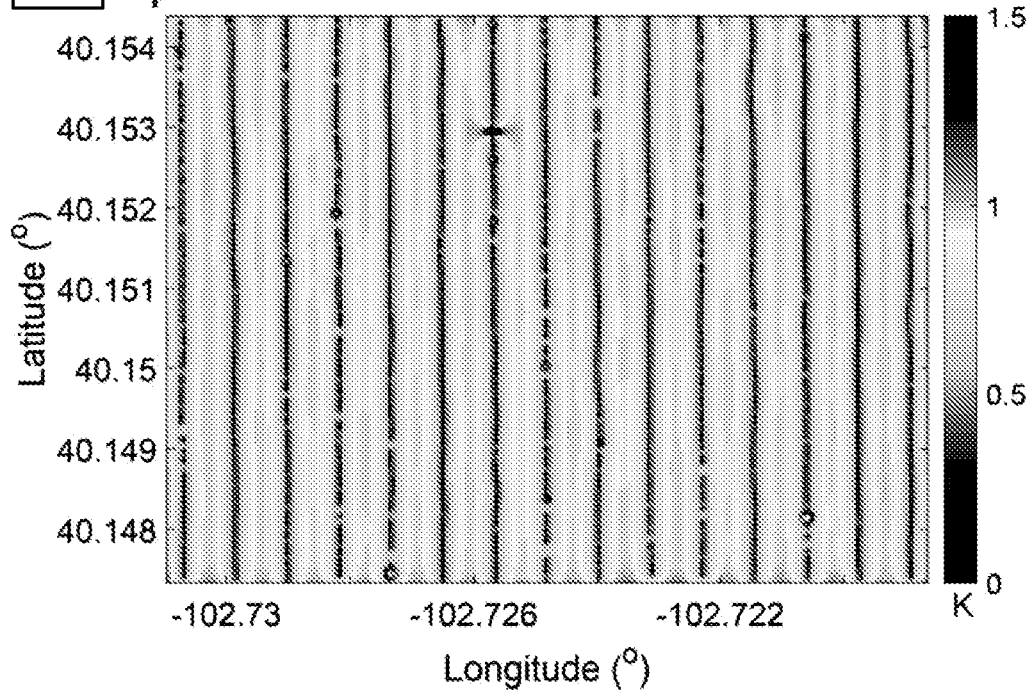
*FIG. 23*

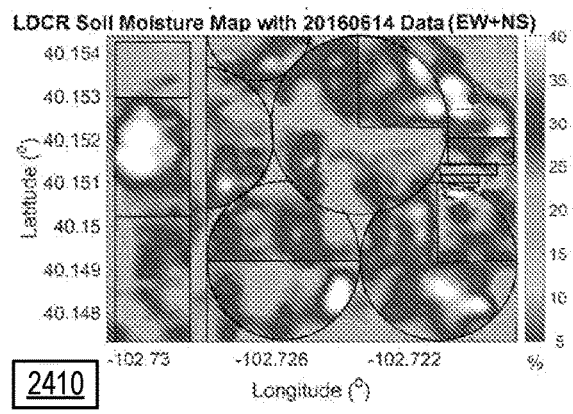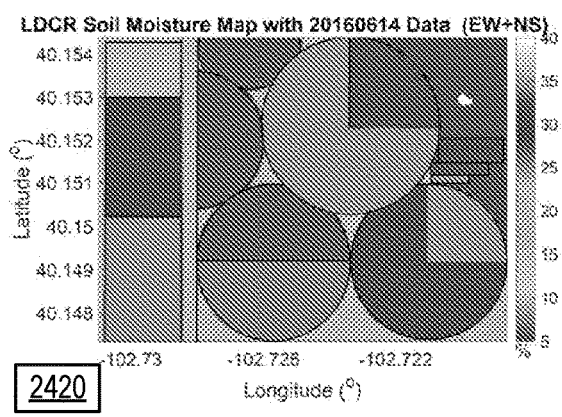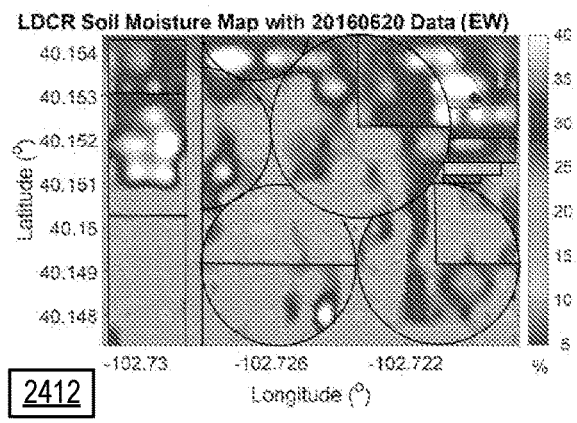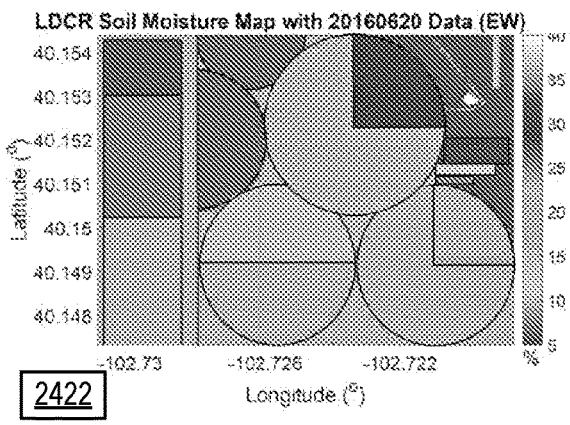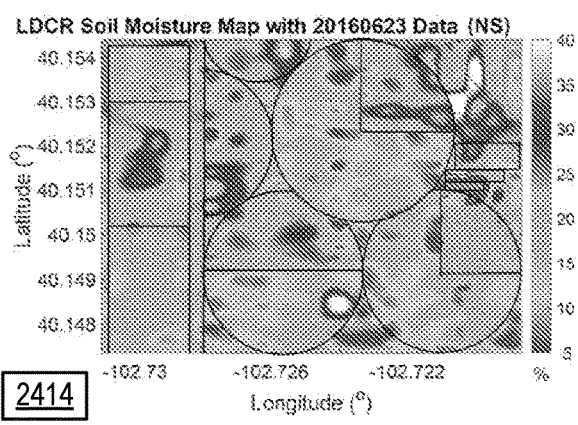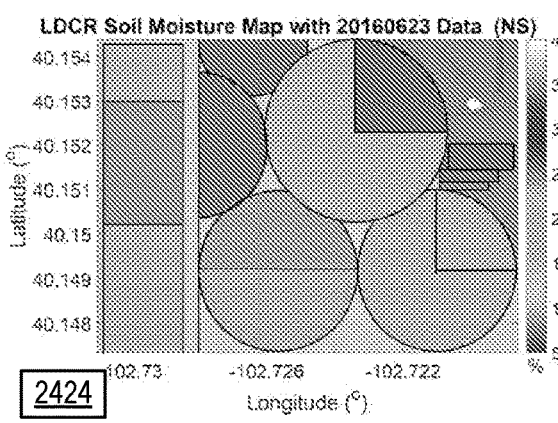
*FIG. 24*

| Probe | VSM on June 14 (%) | VSM on June 20 (%) | VSM on June 23 (%) |
|---|---|---|---|
| 2 | 23.92 | 13.10 | 11.08 |
| 3 | 35.09 | 22.64 | 18.27 |
| 4 | 21.93 | 16.86 | 14.68 |
| 5 | 27.94 | 17.68 | 20.84 |
| 6 | 28.63 | 17/65 | 12.87 |
| 7 | 31.96 | 21.73 | 16.45 |
| 8 | 24.32 | 12.81 | 12.55 |
| 9 | 27.13 | 12.79 | 15.36 |

| Sections (vegetation cover) | 06/14 VSM (LSC) | Irrigation | 06/20 VSM (LSC) | Irrigation | 06/23 VSM (LSC) |
| --- | --- | --- | --- | --- | --- |
| | UCLSC | | UCLSC | | UCLSC |
| Lateral (corn) | 31.7% | | 29.8% | | 21.5% |
| | 28.1% | | 25.5% | | 24.6% |
| Lateral (soybean) | 24.8% | | 18.3% | 0.5 inch on 06/22 | 17.6% |
| | 24.9% | | 17.7% | | 20.9% |
| Lateral (wheat) | 20.0% | 1 inch on 06/17 | 26.4% | | 17.7% |
| | 17.2% | | 27.2% | | 20.3% |
| Circle A NE (sorghum) | 25.4% | 0.5 inch on 06/17 | 19.3% | 0.5 inch on 06/21 | 17.9% |
| | 25.0% | | 18.6% | | 17.4% |
| Circle A (corn) | 30.4% | | 21.8% | 0.5 inch on 06/20 | 15.4% |
| | 28.3% | | 20.7% | | 18.3% |
| Circle B north half (corn) | 27.0% | | 15.9% | 0.5 inch on 06/21 | 21.1% |
| | 25.8% | | 14.3% | | 23.8% |
| Circle B south half (corn) | 26.6% | | 20.0% | | 16.4% |
| | 24.6% | | 18.1% | | 17.4% |
| Circle C NE (sugar beets) | 30.3% | 0.5 inch on 06/17 | 28.3% | | 23.2% |
| | 30.2% | | 29.3% | | 26.2% |
| Circle C (corn) | 25.5% | | 22.7% | 0.5 inch on 06/20 | 14.3% |
| | 23.6% | | 21.5% | | 16.1% |
| Non-irrigated land | 20.2% | | 15.1% | | 10.3% |
| | 20.0% | | 15.8% | | 11.5% |

*FIG. 29*

| Error Source | Corn | | Wheat | | Soybeans | |
|---|---|---|---|---|---|---|
| | Beneath Flight Line | Between Flight Line | Beneath Flight Line | Between Flight Line | Beneath Flight Line | Between Flight Line |
| $\Delta T_{RMS,s} = 2.58$ K | 3.76% | 6.66% | 3.78% | 6.73% | 3.88% | 6.77% |
| $\beta_{e_{W_v}} = 0.2$ kg/m² | 1.53% | 0.74% | 1.71% | 0.70% | 1.54% | 0.29% |
| $\sigma_{e_{W_v}} = 0.2$ kg/m² | 0.00% | 0.00% | 0.01% | 0.00% | 0.00% | 0.00% |
| $\beta_{e_{T_P}} = 5$ K | 0.54% | 0.21% | 0.56% | 0.19% | 0.53% | 0.18% |
| $\sigma_{e_{T_P}} = 5$ K | 0.00% | 0.00% | 0.00% | 0.00% | 0.00% | 0.00% |
| $\beta_{e_S} = 5\%$ | 0.08% | 0.00% | 0.08% | 0.00% | 0.07% | 0.02% |
| $\sigma_{e_S} = 5\%$ | 0.00% | 0.00% | 0.00% | 0.00% | 0.00% | 0.00% |
| $\beta_{e_C} = 5\%$ | 0.01% | 0.00% | 0.02% | 0.00% | 0.01% | 0.00% |
| $\sigma_{e_C} = 5\%$ | 0.00% | 0.00% | 0.00% | 0.00% | 0.00% | 0.00% |
| $\beta_{e_{b_h}} = 0.02$ | 0.42% | 0.10% | 0.33% | 0.12% | 0.53% | 0.18% |
| $\beta_{e_{b_v}} = 0.02$ | 0.13% | 0.00% | 0.10% | 0.00% | 0.17% | 0.02% |
| $\beta_{e_{h_R}} = 0.02$ | 0.10% | 0.00% | 0.10% | 0.00% | 0.10% | 0.00% |
| $\beta_{e_\omega} = 0.01$ | 0.10% | 0.00% | 0.10% | 0.00% | 0.10% | 0.00% |
| Nonlinearity | 0.00% | 0.00% | 0.00% | 0.00% | 0.00% | 0.00% |
| Total | 5.41% | 7.11% | 5.80% | 7.33% | 5.70% | 7.28% |

*FIG. 32*

RADIOMETER AND RADIOMETER-BASED SOIL MOISTURE DETERMINATION METHOD

RELATED APPLICATIONS

This application claims priority to U.S. Provisional Patent Application No. 63/225,422, filed Jul. 23, 2021, which is incorporated herein by reference in its entirety.

STATEMENT REGARDING FEDERALLY SPONSORED RESEARCH OR DEVELOPMENT

This invention was made with government support under grant number NNX14CG09C awarded by NASA. The government has certain rights in the invention.

BACKGROUND

Soil moisture is of fundamental importance to many hydrological, biological, and geochemical processes, and plays an important role in the development and evolution of convective weather and precipitation, and impacts water resource management, agriculture, and flood runoff prediction. Passive microwave remote sensing at L-band (1-2 GHz) is a promising approach to operationally measure soil moisture. Soil Moisture and Ocean Salinity (SMOS) mission launched by the European Space Agency (ESA) in November 2009 and NASA's Soil Moisture Active Passive (SMAP) mission launched in January 2015 have provided spaceborne global measurements of soil moisture and surface freeze-thaw state at fixed crossing times and with spatial resolutions as low as 9 km for some products. However, the observation of soil moisture on smaller spatial scales and at arbitrary diurnal times for satellite data validation, precision agriculture, and evaporation and transpiration studies of boundary layer heat transport is yet needed.

SUMMARY

The present embodiments include a method and a system of determining moisture content in soil using a lobe differencing correlation radiometer (LDCR). LDCR may be integrated in a lightweight small unmanned aircraft system (UAS), which provides several distinct advantages, foremost of which is sub-watershed coverage at a kilometer scale at a high spatial resolution in the range of a decameter. Embodiments disclosed herein are suitable for scaling studies, watershed and cropland management, and other applications such as trafficability at comparatively low fixed and operating costs.

In a first aspect, a method for determining soil moisture of a scene includes (i) generating a first antenna output in response to an upwelling thermal emission from the scene, (ii) generating a second antenna output in response to a downwelling thermal emission from sky above the scene, (iii) coupling the first antenna output and the second antenna output to yield a combined output having a quadrature phase difference between the first antenna output and the second antenna output, (iv) calculating a brightness-temperature difference based at least partially on the combined output, and (v) calculating a soil moisture based on soil-vegetation radiative transfer model using the brightness-temperature difference.

In a second aspect, a radiometer for determining soil moisture of a scene includes a first passive microwave antenna, a second passive microwave antenna, a quadrature coupler, and a signal correlator. The first passive microwave antenna has a nadir-pointing main lobe. The second passive microwave antenna has a zenith-pointing main lobe, and is vertically separated from the first passive microwave antenna by a quarter of a resonant wavelength of the second passive microwave antenna. The quadrature coupler has a first input connected to an output of the first passive microwave antenna and a second input connected to an output of the second passive microwave antenna. The signal correlator is coupled to an output of the quadrature coupler, and outputs a correlator voltage linearly related to a difference between the first and the second inputs of the quadrature coupler.

BRIEF DESCRIPTION OF THE FIGURES

FIG. 3 shows plots illustrating parameters from a preflight calibration of an embodiment of the LDCR of FIGS. 2A and 2B.

FIG. 4 is a table of calculated parameters from preflight and inflight calibrations of an embodiment of the LDCR of FIGS. 2A and 2B.

FIG. 10 is a table of land cover parameters for corrections in the soil-vegetation radiative transfer model of FIG. 8.

FIG. 13 shows plots illustrating fitting parameters for the antenna temperature contributions in the algorithm of FIG. 8.

FIG. 15 illustrates a flight path of an embodiment of the airborne LDCR system of FIG. 5 and the measured vegetation water content of a surveyed area at the Canton site.

FIGS. 17 and 18 show maps of measured volumetric soil moisture and the estimation error in the measurements of the surveyed area of FIG. 15.

FIG. 20 shows maps illustrating flight paths of an embodiment of the airborne LDCR system of FIG. 5, the land cover type, and vegetation water content of a mapping area at the TRF site.

FIGS. 22 and 23 show maps of surface temperature and the estimation error in the measurements of the mapping area of FIG. 20.

FIG. 24 shows maps of volumetric soil moisture retrieved from the mapping area of FIG. 20 using two different functions in the algorithm of FIG. 8.

FIG. 29 is a table showing calculated volumetric soil moisture for each section of the mapping area of FIG. 20 using two different functions of FIG. 24.

FIG. 32 is a table showing the estimation error in the data shown in FIG. 29.

DETAILED DESCRIPTION OF THE EMBODIMENTS

The first retrieved soil moisture maps using an unmanned aircraft system (UAS)-borne L-band radiometer in 2010 demonstrated the capabilities of drone platforms for high spatial resolution soil moisture mapping. Such capabilities have recently been further demonstrated using an embodiment of the current invention, an LDCR on a UAS platform, and are described herein. The LDCR provides airborne mapping of soil moisture on spatial scales as small as several meters (i.e., approximately the height of the aircraft platform). Embodiments disclosed herein include an integrated design of the LDCR on a lightweight UAS, which provides several distinct advantages, foremost of which is sub-watershed (~km scale) coverage at very high (~decameter) spatial resolution. Embodiments disclosed herein are suitable for scaling studies, watershed and cropland management, and other applications such as trafficability at comparatively low fixed and operating costs.

Observations of L-band require radiometric absolute accuracy of order ~1 K or better in the upwelling antenna temperature measurements. This level of accuracy has been achieved, as described below, using the LDCR by differencing the upwelling antenna temperature with the well-known downwelling temperature of cold space. Accordingly, the LDCR antenna structure is designed to have lobes that independently view both nadir and zenith using a unique lightweight microstrip collinear (MiCo) structure. The LDCR measures the difference in antenna temperature between these two lobes.

LDCR Hardware

Figure 1:
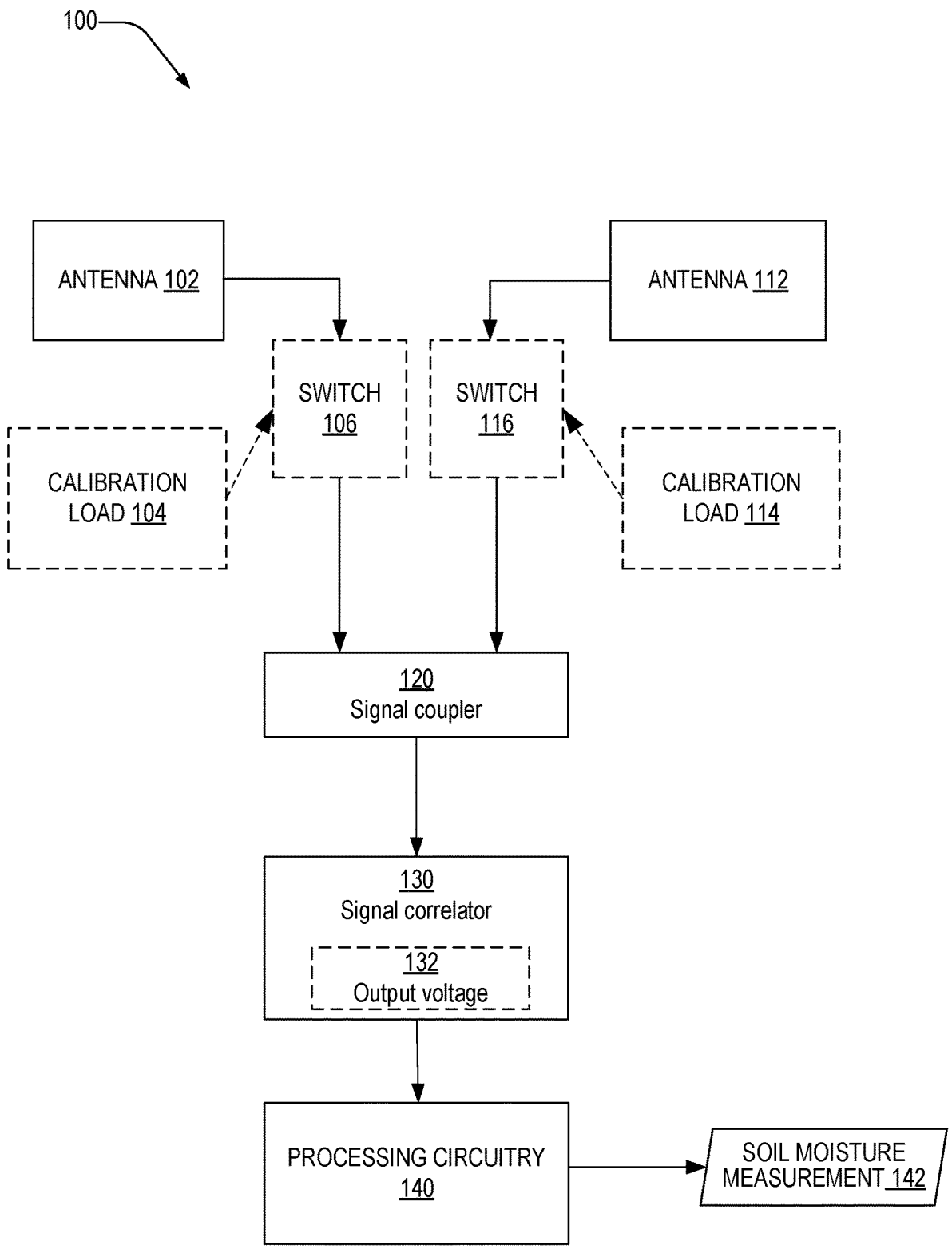
FIG. 1 is a block diagram of a radiometer for determining soil moisture, in an embodiment.

FIG. 1 is a block diagram of a radiometer 100 for determining soil moisture. In a use scenario, radiometer 100 is mounted on an aircraft for determining soil moisture. An example of radiometer 100 is the lobe differencing correlation radiometer (LDCR) shown in FIG. 2. Radiometer 100 includes an antenna 102, an antenna 112, a signal coupler 120, a signal correlator 130, and a processing circuitry 140. Antennas 102 and 112 may be microstrip collinear (MiCo) antennas.

In certain embodiments, antenna 102 is a passive microwave antenna having its main lobe pointing substantially in zenith direction to detect microwave emission from cosmic background. In such embodiments, antenna 102 measures a downwelling brightness temperature, or downwelling temperature ($T_D$). The cosmic background emission is a known stable parameter, and, therefore, the brightness temperature measured by antenna 102 may be used as a reference baseline for radiometer 100.

In certain embodiments, antenna 112 is a passive microwave antenna having its main lobe pointing substantially in nadir direction to detect microwave emission from the ground. In such embodiments, antenna 112 measures an upwelling brightness temperature, or upwelling temperature ($T_U$). Antennas 102 and 112 may be physically separated to create a phase difference in the measurements from the two antennas. For example, antenna 102 and antenna 112 may be separated vertically by a quarter of the operating wavelength of radiometer 100.

Signal coupler 120 couples respective output signals from antennas 102 and 112. Signal coupler 120 may be an RF hybrid coupler, which provides a 90° phase difference between the two output signals. In certain embodiments, the resulting phase difference, when combined with the quarter wavelength vertical separation between antennas 102 and 112, provides the quadrature phase difference and effectively implements main lobes in antenna 102 and 112 for downwelling and upwelling brightness temperature measurements, respectively.

Signal correlator 130, which may be an analog correlator or a digital correlator, calculates the difference between $T_D$ and $T_y$. In an embodiment, the output of signal correlator 130 is an output voltage 132, which may be an analog voltage. Output voltage 132 may be linearly related to the difference, $T_U$-$T_D$, with an offset that may have a dominant contribution from the correlator electronics. A relationship factor between the output voltage 132 and the input temperature difference may include correction factors coming from at least the signal loss in the electronics path of the signal, and may depend on the physical temperature of the correlator. These factors may be determined from a plurality of calibrations prior to operating radiometer 100 or during the operation of radiometer 100.

In operation of radiometer 100, output voltage 132 may drift and have sensitivity dependent on the physical temperature of electronics of signal correlator 130. Radiometer 100 may be equipped with a calibration mode to compensate for the physical temperature dependency, such that when radiometer 100 is in calibration mode, cold calibration load 104, $T_C$, may be connected to signal coupler 120 in place of downwelling antenna 102. Switch 106, which may be controlled by processing circuitry 140, selects which of the downwelling antenna 102 or cold calibration load 104 is connected to signal coupler 120. In addition, a hot calibration load 114, $T_H$, may be connected to signal coupler 120 in place of upwelling antenna 112 when radiometer 100 is in calibration mode. Switch 116, which may be controlled by processing circuitry 140, selects which of the upwelling antenna 112 or hot calibration load 114 is connected to signal coupler 120. In calibration mode, offset drift and sensitivity changes in the output of signal correlator 130 may be calculated based on calibrated characteristics of calibration loads 104 and 114.

Processing circuitry 140 may calculate soil moisture based on at least the output voltage 132 of signal correlator 130. Output voltage 132 may include, in addition to the measurements from antennas 102 and 112, temperature-dependent contributions from offset drift and sensitivity changes coming from at least signal correlator 130. Processing circuitry 140 may periodically select calibration mode to track at least offset drift and sensitivity changes in the output voltage of signal correlator 130 to compensate physical temperature dependency in calculation of soil moisture.

Figure 2A:
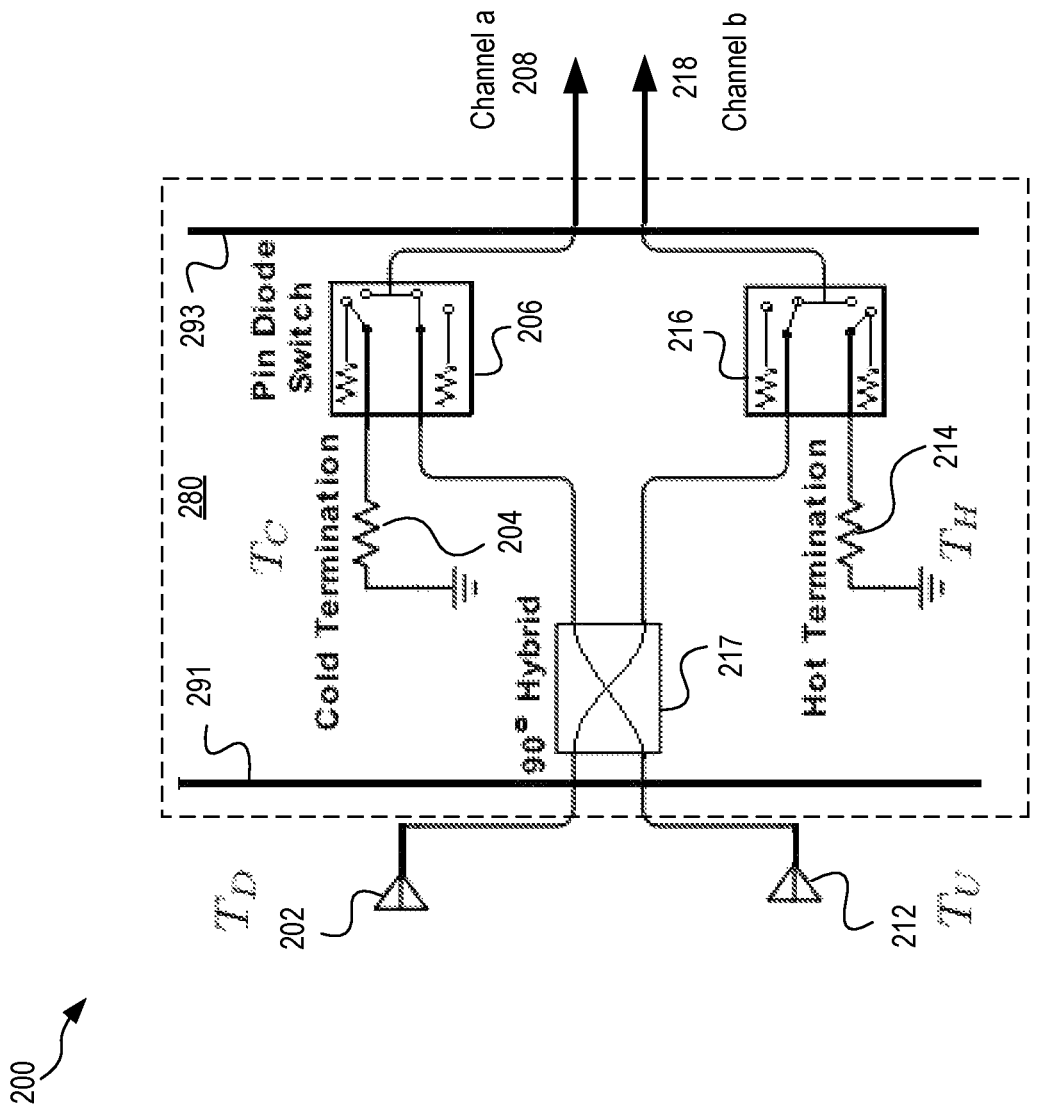
FIGS. 2A and 2B are block diagrams of a LDCR, which is an example of the radiometer of FIG. 1.
Figure 2B:
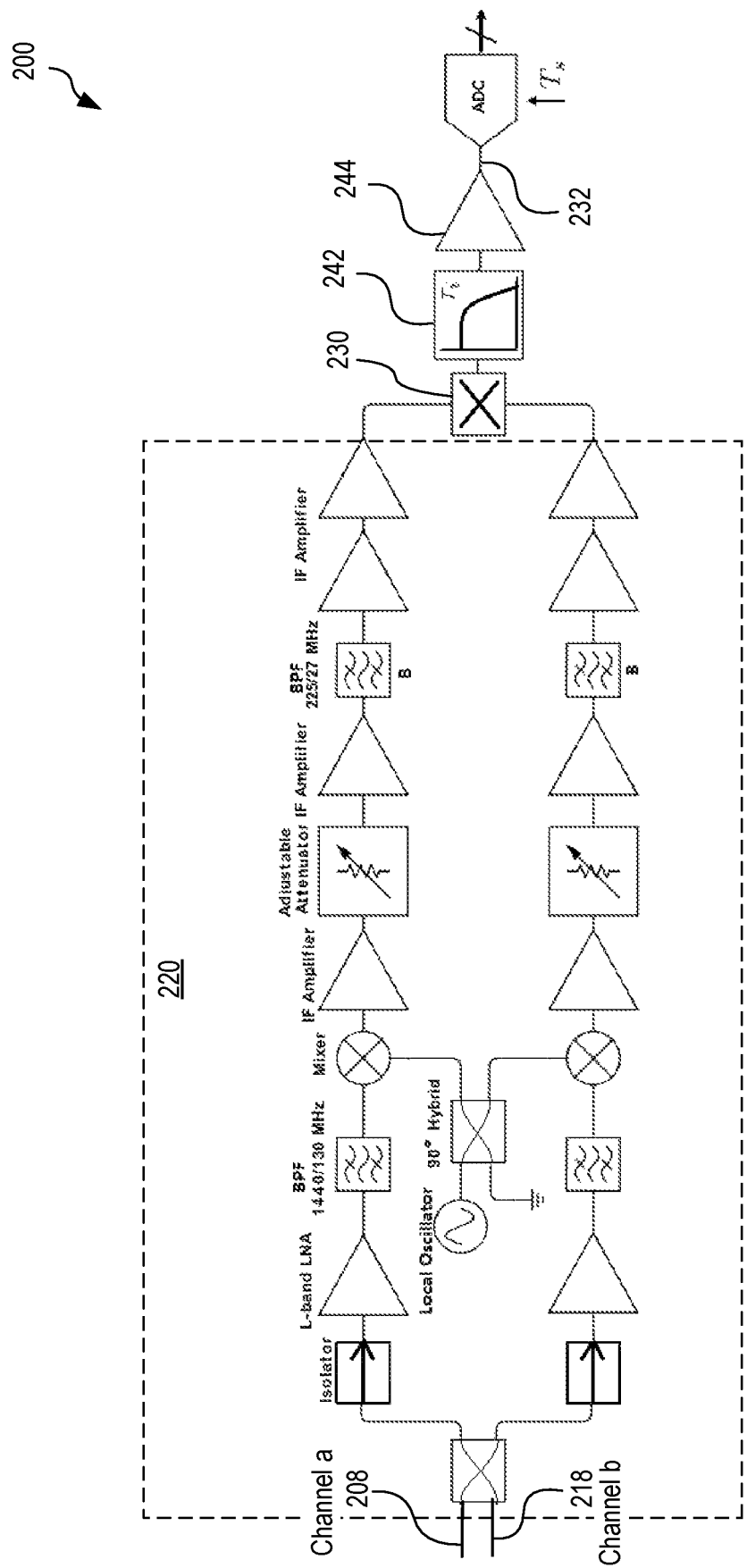

FIGS. 2A and 2B are block diagrams of a LDCR 200, which is an example of radiometer 100 of FIG. 1. LDCR 200, which is an example of a radiometer 100, may be fabricated on a single board and may be integrated into a small unmanned aircraft system (UAS). Examples of a UAS include, but are not limited to, a S2 aircraft built by Black Swift Technologies LLC or a Tempest aircraft that was modified by Black Swift Technologies LLC. FIGS. 2A and 2B are best viewed together in the following description of LDCR 200. FIG. 2A illustrates a radiofrequency (RF) frontend 280 of LDCR 200. RF frontend 280 includes an upwelling antenna 202 and a downwelling antenna 212, which are respective examples of antenna 102 and 112. Antennas 202 and 212 may be physically separated by a quarter of the operating wavelength of the radiometer. RF frontend 280 also includes calibration sources: a cold calibration load 204 and a hot calibration load 214, and switches 206 and 216, which are respective examples of calibration loads 104 and 114. and switches 106 and 116. FIG. 2A denotes a reference plane 293 and an antenna plane 291 for ease of description below.

Each of the switches 206 and 216 may operate independently of the other switch, such that there are four possible states, which are referred to as four switched states henceforth. The four switched states are: (i) internal source state: both calibration loads 204 and 214 are selected, (ii) scene state: both antennas 202 and 212 are selected, (iii) mixed hot-downwelling state: downwelling antenna 202 and hot calibration load 214 are selected, and (iv) mixed upwelling-cold state: upwelling antenna 212 and cold calibration load 204 are selected.

LDCR 200 includes a signal coupler 220 and a signal correlator 230, which are respective examples of signal coupler 120 and signal correlator 130 of radiometer 100. The corresponding outputs, selected channel a 208 and channel b 218, of switches 206 and 216 are fed into a signal coupler 220. The output of signal correlator 230, after being filtered by a low-pass filter 242 and a video amplifier 244, is an analog output voltage 232. Analog output voltage 232 is an example of output voltage 132.

In embodiments, switches 206 and 216 enable either antennas 202 or 212 or their respective calibration loads 204 or 214 to be periodically connected to each quadrature-summed radiometer channel. Consequently, LDCR 200 may be operated in one of four switched calibration states. For example, when antennas 202 and 212 are connected, the quadrature phase difference provided by the first 900 coupler, along with the 900 difference provided by the MiCo antenna's quarter-wavelength vertical separation, effectively implements upwelling and downwelling antenna lobes. The associated upwelling and downwelling signals are defined at reference plane 293. This lobe differential architecture using the stable downwelling brightness temperature of cold space as a reference, meanwhile the internal calibration references are used to determine the voltage offset and thermal drift of the entire system.

In each of the four calibration states, the analog correlator output voltage (e.g., output voltage 132, FIG. 1) is linearly correlated to the temperature differences at reference plane 293. In the following sections, for each of the calibration states, output voltage 132 is further described hereinbelow. The LDCR sensitivity and offset voltage may be characterized prior to usage (e.g., in the laboratory), the process referred to as preflight calibration hereinbelow. Additionally, the validation process during usage using the four switch state data is referred to as inflight calibration hereinbelow. Physical temperature effects that induce receiver drift may be accommodated in the calibration processes. The measurements and parameters shown hereinbelow are specific to a certain embodiment of a LDCR (e.g., Rev. A) and may be different in other embodiments.

LDCR Calibration Switch States

The analog correlator output voltage 232, $v_a$, after a RC low pass filter 242 and a video amplifier 244 for all switch states can be expressed as $$\langle v_a \rangle = G_0 k B (T_{A_b} - T_{A_a}) + v_0 \quad (1)$$

where $T_{A_a}$ and $T_{A_b}$ are input antenna temperature for channel a 208 and channel b 218 as defined at reference plane 293 for each of four switch states, and (*) denotes time averaging. The offset voltage $v_0$ is the output voltage with a null antenna temperature difference input, and k is the Boltzmann's constant. The gain $G_0$ is proportional to the geometric mean of the power gain of the two LDCR amplifying channels and RC low pass filter integration time constant $\tau_i$. In an embodiment, the instrument bandwidth B is 27 MHz (i.e., from 1400 to 1427 MHz) and $\tau_i$=RC is 1.5 ms.

The LDCR gain $G_0$ is estimated based on the sum of the gains and losses of all components including the RF, down-conversion, and intermediate frequency (IF) components, analog correlator, and video amplifier. Assuming the first 90° hybrid coupler is balanced and the two receiving channels a 208 and b 218 are uncoupled, the temperatures $T_{A_a}$ and $T_{A_b}$ at the reference plane are $$T_{A_a} = \begin{cases} \alpha_{a_c} T_C + (1 - \alpha_{a_c}) T_{P_{a_c}}, & \text{internal source} \\ \alpha_{a_s} T_D + (1 - \alpha_{a_s}) T_{P_{a_s}}, & \text{antenna input} \end{cases} \quad (2)$$

$$T_{A_b} = \begin{cases} \alpha_{b_c} T_H + (1 - \alpha_{b_c}) T_{P_{b_c}}, & \text{internal source} \\ \alpha_{b_s} T_U + (1 - \alpha_{b_s}) T_{P_{b_s}}, & \text{antenna input} \end{cases} \quad (3)$$

where $T_C$ and $T_H$ are the physical temperatures of cold and hot internal calibration loads 204 and 214, and $T_U$ and $T_D$ are the LDCR observed temperatures of upwelling and downwelling antennas 202 and 212. The internal calibration temperatures are typically cooled to ~273 K for $T_C$ and heated to ~328 K for $T_H$. The correction factor $\alpha_{a_c}$ is proportional to the internal calibration source path RF loss from the internal source to the reference plane, and the correction factor $\alpha_{a_s}$ is proportional to the antenna input path RF loss from the antenna plane to the reference plane for channel a 208. Similarly, $\alpha_{b_c}$ and $\alpha_{b_s}$ are correction factors for channel b 218. $T_{P_{x_i}}$ denotes a physical temperature in channel x with input i. For examples, the internal source paths and antenna input path have physical temperatures of $T_{P_{a_c}}$, $T_{P_{b_c}}$, $T_{P_{a_s}}$, and $T_{P_{b_s}}$, respectively.

On the LDCR receiving board, the microstrip transmission lines to the left of reference plane 293 in RF frontend 280 in both channels may be fabricated to be mirror symmetric. Consequently, for the PIN diode switches, examples of which include Hittite HMC284MS8G, the insertion loss for either path is the same to within 0.1 dB. Accordingly, the correction factors in channel a 208 and channel b 218 are assumed to be equal to within a few percent, that is $\alpha_c = \alpha_{a_c} \cong \alpha_b s$ and $\alpha_s = \alpha_{a_g} \cong \alpha_{b_s}$. The physical temperatures of all paths have the same value $T_{P_i}$ to within 0.1 K. With these assumptions, the reference temperature differences are modeled as Internal source state: $T_{A_b} - T_{A_b} = \alpha_c(T_H - T_C)$  (4)

Scene state: $T_{A_b} - T_{A_a} = \alpha_s(T_U - T_D)$

Mixed hot–downwelling state:

$T_{A_b} - T_{A_a} = \alpha_c T_H - \alpha_s T_D + (\alpha_s - \alpha_c)T_{P_i}$ Mixed upwelling–cold state:

$T_{A_b} - T_{A_a} = \alpha_s T_U - \alpha_c T_C + (\alpha_c - \alpha_s)T_{P_i}$ to within a temperature bias of less than ~3-4 K in the worst case of parameter error. The internal calibration source correction factor ac may be estimated from the internal calibration source emissivity (>99%) and PIN diode switch insertion loss (0.7 dB) to be $10^{-0.7/10} \times 99\% = 0.84$. The value of $\alpha_s$ for the antenna input may be similarly estimated using RF losses including the coaxial and microstrip line loss (1.2 dB), the insertion loss of the first 900 hybrid coupler (0.25 dB), and the PIN diode switch insertion loss (0.7 dB). In an embodiment, the value of $\alpha_s$ is thus approximately $10^{-(1.2+0.25+0.7)/10} = 0.61$.

For the four switch states, the analog output voltage can be expressed as

Internal source state: $\langle v_a \rangle_{HC} = \alpha_c G_0 kB(T_H - T_C) + v_0$  (5)

Scene state: $\langle v_a \rangle_{UD} = \alpha_s G_0 kB(T_U - T_D) + v_0$

Mixed hot–downwelling state:

$\langle v_a \rangle_{HD} = G_0 kB(\alpha_c T_H - \alpha_s T_D + (\alpha_s - \alpha_c)T_{P_i}) + v_0$ Mixed upwelling–cold state:

$\langle v_a \rangle_{UC} = G_0 kB(\alpha_s T_U - \alpha_c T_C + (\alpha_c - \alpha_s)T_{P_i}) + v_0$ The calibration process is based on internal source and scene switch states with the measurements from two mixed switch states used as supplementary data for bias correction purposes.

The LDCR $\Delta T_{rms}$ is a key performance statistic describing the minimum 1-sigma detectable temperature change and is defined with respect to reference plane 293:

$$\Delta T_{rms} = \frac{\sigma_{v_a}}{\frac{\partial \langle v_a \rangle}{\partial (T_{A_b} - T_{A_a})}} = \frac{\sqrt{T_{A_a}^2 + T_{A_b}^2 + (T_{R_a} + T_{R_b})(T_{A_a} + T_{A_b}) + 2T_{R_a}T_{R_b}}}{\sqrt{B\tau_i}} \quad (6)$$

where $\sigma_{v_a}$ is a standard deviation of correlator output voltage 232 and $T_{R_a}$ and $T_{R_b}$ are the receiver noise temperatures of the two LDCR receiving channels a 208 and b 218. Accordingly, $\sigma_{v_a} = G_0 kB \Delta T_{rms}$. Using these relations, the values of $T_{R_a}$ and $T_{R_b}$ may be empirically determined by parameter fitting to be 500±10 K by measuring $\sigma_{v_a}$, using ~2×10$^6$ independent samples, and presenting a variety of known input antenna temperatures $T_{A_a}$ and $T_{A_b}$. In this process, it is presumed that $T_{R_a} = T_{R_b}$ and that $G_0$, B, $\tau_i$, $\alpha_c$, and $\alpha_s$ are accurately known based on estimation. For the internal source and scene switch state, the output voltage and temperature differences of $T_H - T_C$ and $T_U - T_D$ are related to $T_{A_b} - T_{A_a}$.

Consequently, the $\Delta T_{rms}$ values for these two switch states are modified as Internal source state: $\Delta T_{rms,c} = \dfrac{\sigma_{v_a}}{\dfrac{\partial \langle v_a \rangle}{\partial (T_H - T_C)}} = \dfrac{\Delta T_{rms}}{\alpha_c}$  (7)

Scene state: $\Delta T_{rms,s} = \dfrac{\sigma_{v_a}}{\dfrac{\partial \langle v_a \rangle}{\partial (T_H - T_C)}} = \dfrac{\Delta T_{rms}}{s}$ where the modified values refer to fundamental precisions possible for measuring $T_H - T_C$ and $T_U - T_D$.

Preflight Calibration

The LDCR preflight calibration process determines the offset voltage $v_0$ and sensitivities $\alpha_c G_0 kB$ and $\alpha_s G_0 kB$ (in mV/K), all of which are found to be primarily dependent on the physical temperature of the analog correlator chip. The offset voltage $v_0$ is independent of switch states, while the sensitivities $\alpha_c G_0 kB$ and $\alpha_s G_0 kB$ differ by 0.4-0.7 dB. The offset $v_0$ may be estimated using equal physical temperatures at the reference plane for the two channels, and the sensitivities for the internal source and scene states may be estimated using known antenna temperature inputs as follows.

The sensitivity $\alpha_s G_0 kB$ for the scene state may be estimated by connecting a matched load to each of the two LDCR inputs through a connectorized 900 hybrid coupler 217. Using this method, the dual-lobe characteristics of the antenna may be simulated. In an embodiment, one of the matched loads is placed in liquid nitrogen (77.3 K), and the other left at room temperature (~295 K). The feedline and quadrature hybrid losses are properly accounted for in this process to provide a precision in $T_U - T_D$ of ~2.5 K. The product $\alpha_c G_0 kB$ for the internal source state may similarly be estimated using the internal calibration sources at known measured temperatures $T_H$ and $T_C$ to a precision in $T_H - T_C$ of ~0.5 K.

FIG. 3 shows plots 310 and 312 illustrating parameters from a preflight calibration of an embodiment of LDCR 200 of FIGS. 2A and 2B. The parameters include sensitivities and offset voltage $v_0$. Plot 310 shows the sensitivity of signal correlator 230 as a function of correlator temperature. Plot 312 shows the offset voltage $v_0$ as a function of correlator temperature. It is noted that: 1) the sensitivities decrease appreciably with correlator chip temperature; and 2) the offset voltage $v_0$ increases approximately linearly with correlator chip temperature from ambient to 319 K. Temperature-dependent models may then be constructed from polynomial fits to these quantities. In an embodiment, based on the estimated sensitivities and offset voltages and their estimation precisions, the LDCR upwelling antenna temperature $T_U$ is determined by the preflight calibration procedure to a precision estimated to be ~5-6 K in bias.

Inflight Calibration

Estimated sensitivities from the preflight calibration may be validated in inflight calibration. For inflight calibration, LDCR, which may be mounted on an UAS, may be flown over an area with known temperatures. To validate this calibration process, a LDCR mounted on a UAS was flown over a calm freshwater pond for a few seconds at approximately 15 m in altitude. The measured upwelling and downwelling antenna temperatures $T_U$ and $T_D$ were calculated from the measured pond surface temperature $T_{P_w}$ of 298 K and the well-known L-band downwelling sky brightness temperature of 5±0.4 K, which is the cold space temperature compensated by ~0.025 dB of atmospheric loss. The upwelling temperature $T_U$ was calculated using the measured polarimetric LDCR antenna gain pattern integrated over the upwelling terrain of view which includes pond and surrounding field, and the Fresnel reflectivity coefficient for flat freshwater. The measured antenna and radome ohmic efficiency of $\eta_l$=78+5% and measured antenna physical temperature $T_{P_A}$ were also considered in this calculation. The water and terrain physical temperature was measured by an LDCR IR sensor where the terrain had a physical temperature ~8 K higher than that of the water. The contribution of the land surrounding the pond to the overall $T_U$ calculation for the selected pond flight line was 0.2-1.5 K.

The analog output voltage vector (minus offset $v_0$) for all switch states may be expressed as $$\begin{bmatrix} \langle v_a \rangle_{UD} - v_0 \\ \langle v_a \rangle_{UC} - v_0 \\ \langle v_a \rangle_{HD} - v_0 \\ \langle v_a \rangle_{HC} - v_0 \end{bmatrix} = \begin{bmatrix} T_U - T_D & 0 \\ T_U - T_{P_i} & T_{P_i} - T_C \\ T_{P_i} - T_D & T_H - T_{P_i} \\ 0 & T_H - T_C \end{bmatrix} \begin{bmatrix} \alpha_s G_0 kB \\ \alpha_c G_0 kB \end{bmatrix} + \overline{n} = \overline{\overline{W}}_c \overline{x} + \overline{n} \quad (8)$$

where $\overline{\overline{W}}_c$ is calibration observation operator, x is a sensitivity vector to be determined, and f is an observation noise vector. The sensitivities were subsequently determined by unbiased linear minimum mean square error (LMMSE) estimation:

$$\begin{bmatrix} \hat{\alpha}_s G_0 kB \\ \hat{\alpha}_c G_0 kB \end{bmatrix} = \overline{\overline{D}}_c \begin{bmatrix} \langle v_a \rangle_{UD} - v_0 \\ \langle v_a \rangle_{UC} - v_0 \\ \langle v_a \rangle_{HD} - v_0 \\ \langle v_a \rangle_{HC} - v_0 \end{bmatrix} - \overline{\overline{D}}_c \overline{\overline{W}}_c \begin{bmatrix} \langle \alpha_s \rangle G_0 kB \\ \langle \alpha_c \rangle G_0 kB \end{bmatrix} + \begin{bmatrix} \langle \alpha_s \rangle G_0 kB \\ \langle \alpha_c \rangle G_0 kB \end{bmatrix} \quad (9)$$

where are $\langle \alpha_s \rangle$ and $\langle \alpha_c \rangle$ are determined sensitivities from preflight calibration. The LMMSE solution provides the calibration operator $\overline{\overline{D}}_c$ which minimizes the sensitivities estimation error $\overline{e} = \hat{\overline{x}} - \overline{x}$. For physical LMMSE estimation, $\overline{\overline{D}}_c$ is calculated as $$\overline{\overline{D}}_c = \overline{\overline{R}}_{xx} \overline{\overline{W}}_c' (\overline{\overline{W}}_c \overline{\overline{R}}_{xx} \overline{\overline{W}}_c + \overline{\overline{R}}_{nn})^{-1} \quad (10)$$

where $\overline{\overline{R}}_{xx}$ and $\overline{\overline{R}}_{nn}$ are sensitivity and observation noise covariance matrices. The sensitivity variations in the values obtained from preflight calibration and observation noises for different switch states are considered to be uncorrelated.

In this particular calibration, the observation noise was calculated from the standard deviation of LDCR analog output voltage, 2.8 mV, and the sensitivity error variance was estimated to be 10% based on the available precision in determining the internal source and antenna input path RF losses. The inflight sensitivities were estimated to be 0.34 and 0.19 mV/K for the internal source state and scene state, respectively. The estimation error $\overline{\overline{R}}_{ee}$ in this process may be calculated as $$\overline{\overline{R}}_{ee} = (\overline{\overline{I}} - \overline{\overline{D}}_c \overline{\overline{W}}) \overline{\overline{R}}_{xx} (\overline{\overline{I}} - \overline{\overline{D}}_c \overline{\overline{W}})^t + \overline{\overline{D}}_c \overline{\overline{R}}_{nn} \overline{\overline{D}}_c' \quad (11)$$

where $\overline{I}$ is a diagonal matrix. The sensitivity estimation error for both internal source and scene states were thus calculated to be 2%. The preflight sensitivities were 0.36 and 0.19 mV/K for the same pond overflight instrument temperature of 316 K. Although the inflight and preflight sensitivities are similar to each other, inflight calibration was used to correct the fitted models in FIG. 3 for all inflight calibration purposes.

FIG. 4 is a table 400 of calculated parameters from preflight and inflight calibrations of an embodiment of the LDCR 200 of FIGS. 2A and 2B. The parameters were calculated for time constant j=1.5 millisecond (msec) and a sampling time interval TS=1. Table 400 includes, for internal source state and scene state, apriori values of sensitivities $\alpha_c G_0 kB$, $\alpha_s G_0 kB$, analog output voltage standard deviation $\sigma_{v_a}$, and calculated values of $\Delta T_{rms}$ using equations (6) and (7). The observed sensitivities are lower by 0.1-1.2 dB than a priori values calculated based on estimated values of $G_0$, $\alpha_c$ and $\alpha_s$. The measured and a priori values of $\sigma_{v_a}$ are approximately the same.

With the sampling interval $T_s$ of 1 msec, a typical ~20 m/s UAS air speed, and decameter (~50 m) antenna 3-dB footprint size, it is reasonable to average the sampled data over ~0.5 second of flight. The output voltage standard deviation $\sigma_{v_a}'$ after averaging can be calculated as $$\sigma_{v_a}' = \frac{\sigma_{v_a}}{\sqrt{N_a}} \left[ \frac{N_a(1-\rho^2) - 2\rho(1-\rho^{N_a})}{N_a(1-\rho)^2} \right]^{1/2} \quad (12)$$

where $\rho = e^{-(\tau_s/\tau_1)}$ is inter-sample correlation that may be introduced by RC low pass filtering, and $N_a$ is the number of samples being digitally averaged. In an embodiment, the integration time was allocated equally to the four switch states with each calibration cycle being 42 msec. $N_a$ was ~100 and the pixel-averaged $\Delta T_{rms,s}$ for the scene state was reduced to 2.58 K.

LDCR Integration into u UAS and Radiofrequency Interference Mitigation

Figure 5:
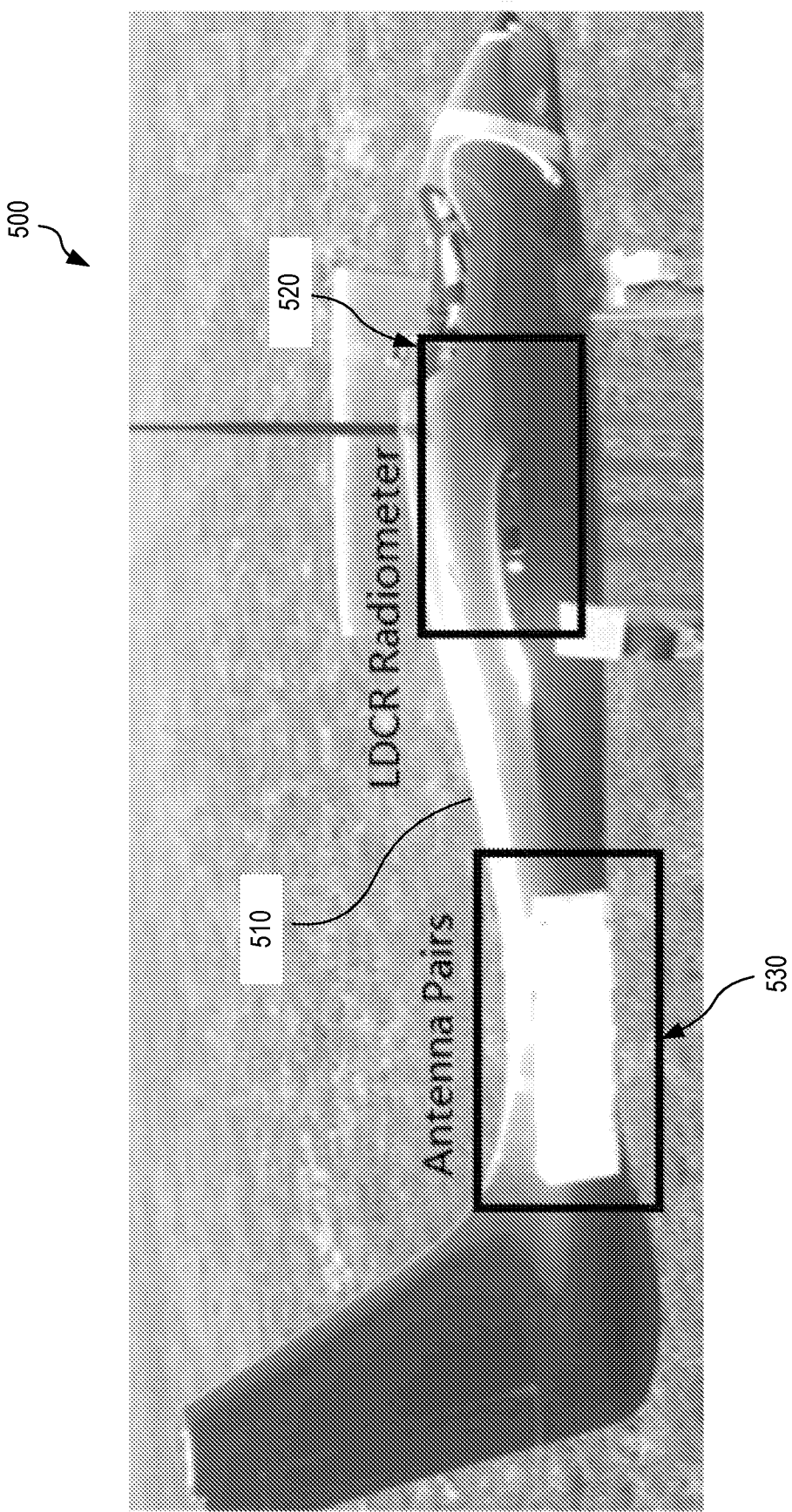
FIG. 5 illustrates an airborne LDCR system, in an embodiment.

FIG. 5 illustrates an airborne LDCR system 500. Airborne LDCR system 500 includes a UAS 510, a LDCR radiometer 520, and an antenna pair 530. LDCR radiometer 520 is an example of LDCR 200, and antenna pair 530 may include antennas 202 and 212 (FIG. 2). The description of airborne LDCR system 500 herein includes a use scenario of a LDCR Rev. A integrated into an UAS called Tempest. The description may be different when using other embodiments of LDCR radiometer and/or other aircraft without departing from the scope of this disclosure. In such a configuration, radio frequency interference (RFI) from UAS 510 is one of the main concerns for passive remote sensing. Upon integration of LDCR radiometer 520 into UAS 510, the motor and motor controller of UAS 510 were found to radiate wide band noise which coupled through LDCR MiCo antennas. This radiation caused the antenna temperature noise to increase up to ~4000 K in a flight test.

Figure 6:
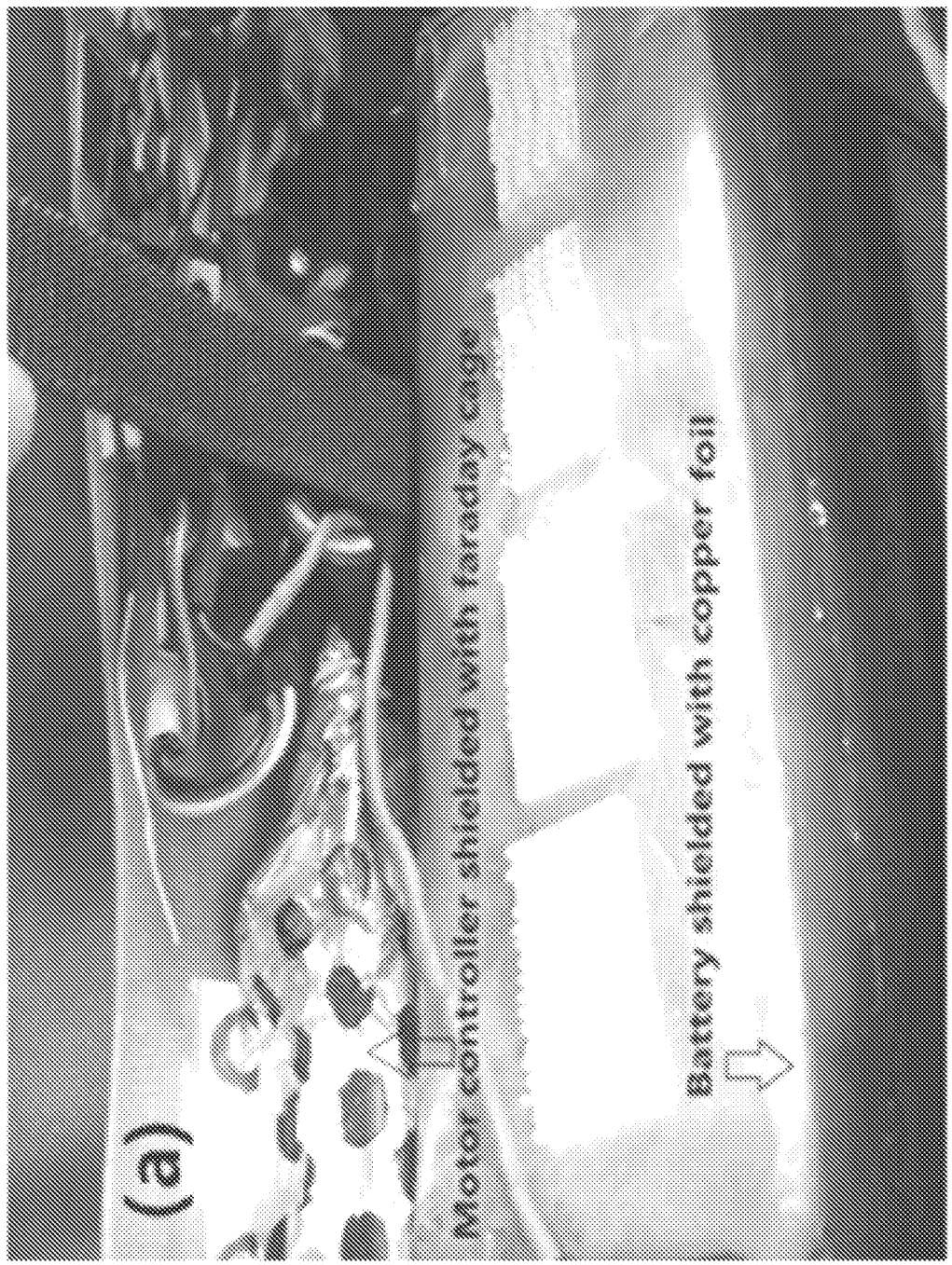
FIG. 6 illustrates an example of electromagnetic shielding in the airborne LDCR system of FIG. 5.
Figure 7:
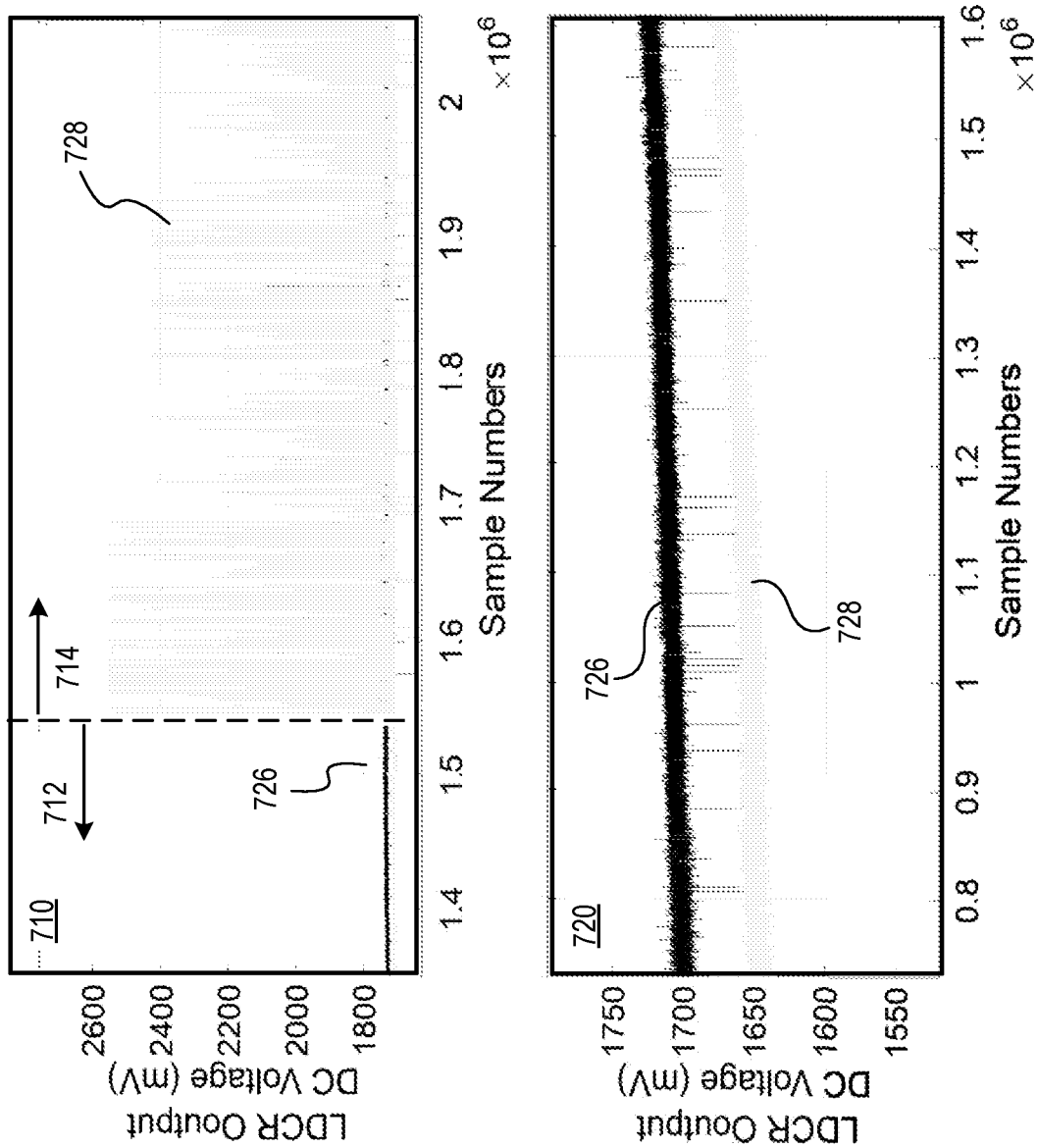
FIG. 7 shows plots illustrating the effectiveness of the electromagnetic shielding shown in FIG. 6.

FIG. 6 illustrates an example of electromagnetic shielding in airborne LDCR system 500 of FIG. 5. After shielding all potential radiating sources, including the motor, motor controller, battery, and all wire connections, the noise was decreased to a level less than the output voltage standard deviation ($\sigma_{v_o}$) for all follow-up flights. FIG. 7 shows plots 710 and 720 illustrating the effectiveness of the electromagnetic shielding shown in FIG. 6. In plot 710, output voltages (e.g., output voltage 132, FIG. 1) for internal source state 726 and scene state 728 show a dramatic difference between when the motor of UAS 510 is powered off 712 and when it is powered on 714. After the shielding is applied (e.g., FIG. 6), plot 720 shows the same output voltages for states 726 and 728 with the motor powered on, which indicate that the output voltages are at the same level as when the motor is powered off. Interference from the microcomputer was not detected.

Soil Moisture Retrieval Background

The LDCR mapping algorithm builds upon soil moisture retrieval techniques established for the Soil Moisture and Ocean Salinity (SMOS) and Soil Moisture Active Passive (SMAP) missions, which are space-borne satellite missions. However, due to the unique LDCR polarization-mixed signal, broad antenna beamwidth, and irregular sampling pattern, the algorithm necessarily departs from that of space-borne missions. The operational SMOS retrieval algorithm is based on the multiangular and dual-polarization observing capabilities of the SMOS interferometric sensor. Soil moisture and vegetation opacity are simultaneously retrieved using the SMOS multiangle polarimetric brightness temperature imagery. The operational soil moisture retrieval method for SMAP uses a single vertically polarized channel in the current baseline algorithm, in which the vegetation opacity is not simultaneously retrieved. Instead, it is calculated from vegetation water content (VWC) measurements which are estimated using normalized differential vegetation index (NDVI) data from NASA's Moderate Resolution Imaging Spectroradiometer (MODIS).

For LDCR, antenna temperature samples of mixed polarization and multiple incident angles are directly measured, and the vegetation opacity is estimated using VWC values from temporally interpolated Landsat normalized differential water index (NDWI) data. An observation operator, using volumetric soil moisture (VSM) data defined on a regular user-defined product grid and computing the observed $T_A$ on an irregular UAS flight sampling grid, was developed to support this method. The integral expression for the LDCR $T_A$ samples is based on a radiative transfer model, τ–ω vegetation opacity model, incorporating VWC correction, an empirical soil dielectric mixing model, and surface roughness correction provided by the so-called H-Q-N model. All models are described below. A linear fit to the integral expression is used to approximate the weakly nonlinear observation operator.

Figure 8:
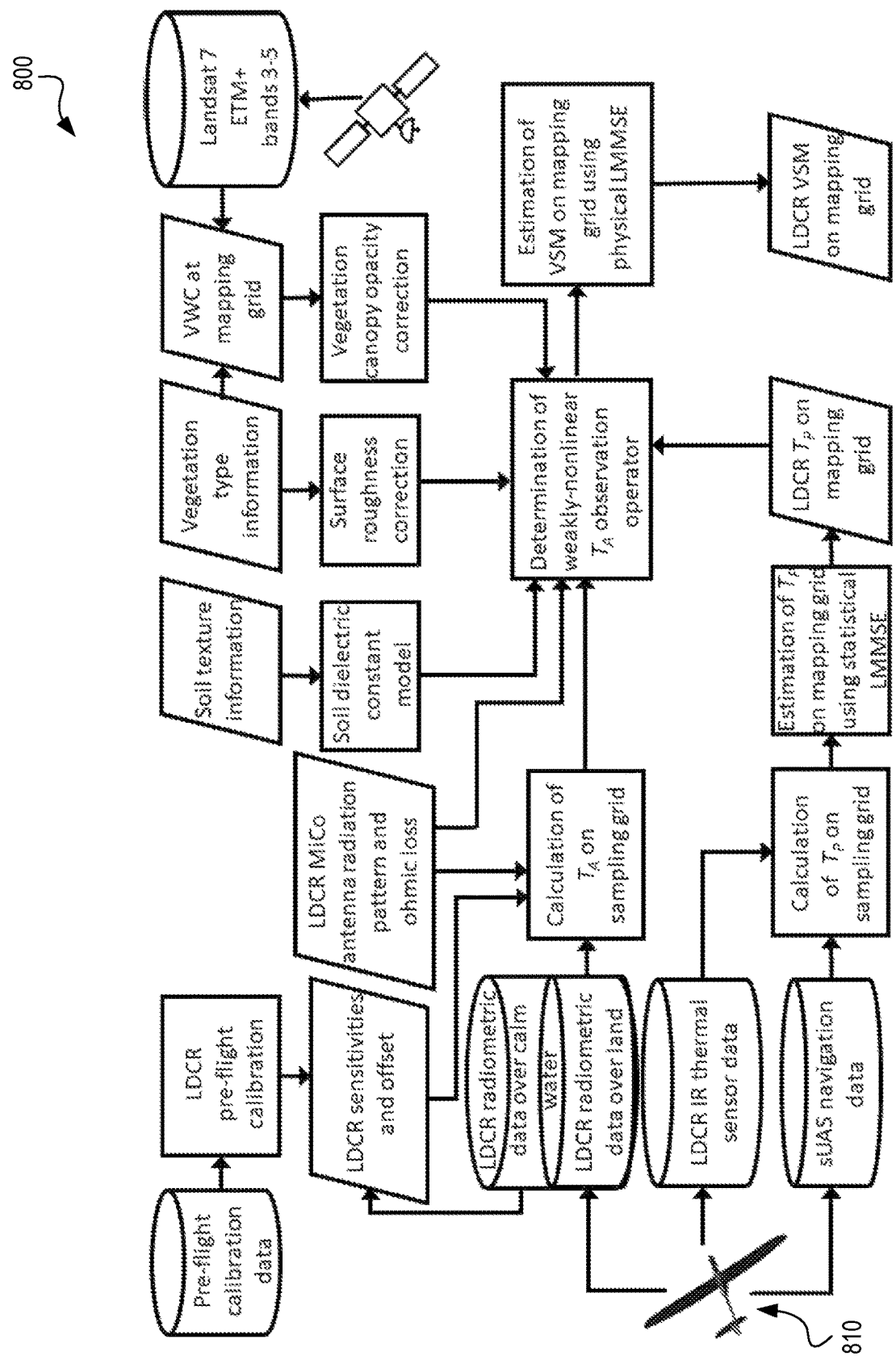
FIG. 8 is a block diagram of an algorithm used in the soil-vegetation radiative transfer model that retrieves and maps volumetric soil moisture data, in an embodiment.

FIG. 8 is a block diagram of an algorithm 800 used in the soil-vegetation radiative transfer (SVRT) model that retrieves and maps volumetric soil moisture data. Algorithm 800 retrieves the LDCR high spatial resolution $T_A$ data from an airborne LDCR system 810, which is an example of airborne LDCR system 500, and maps the VSM on a user-defined grid using a LMMSE estimation method. Algorithm 800 may be implemented partially or fully by one or more processors either onboard a LDCR board (e.g., LDCR radiometer 520) or a remote computing system. Algorithm 800 is described in detail in the following sections. The LMMSE inversion scheme, employed by algorithm 800, has been widely applied as an optimal estimator in passive and active remote sensing for decades. The mixture of polarizations and incident angles is addressed in the retrieval formulation along with the spatial covariance of VSM as relevant for managed cropland of various vegetation types and resulting VSM error variance. A priori information on vegetation and surface homogeneity is shown to be readily imposed on the retrieval operator by presetting the off-diagonal elements in the VSM spatial covariance matrix as described below.

Soil-Vegetation Radiative Transfer Models

For passive remote sensing of soil moisture, the SVRT model incorporating scattering to zeroth order is commonly used for tenuous vegetation cover such as cultivated crops and grasses, and to first order for heavy vegetation covers such as shrubs and trees. In the description below, soil moisture mapping over mostly cultivar and grass vegetation cover is described. Accordingly, the τ–ω zeroth order radiative transfer (RT) model is used for canopy attenuation.

τ–ω Model

Figure 9:
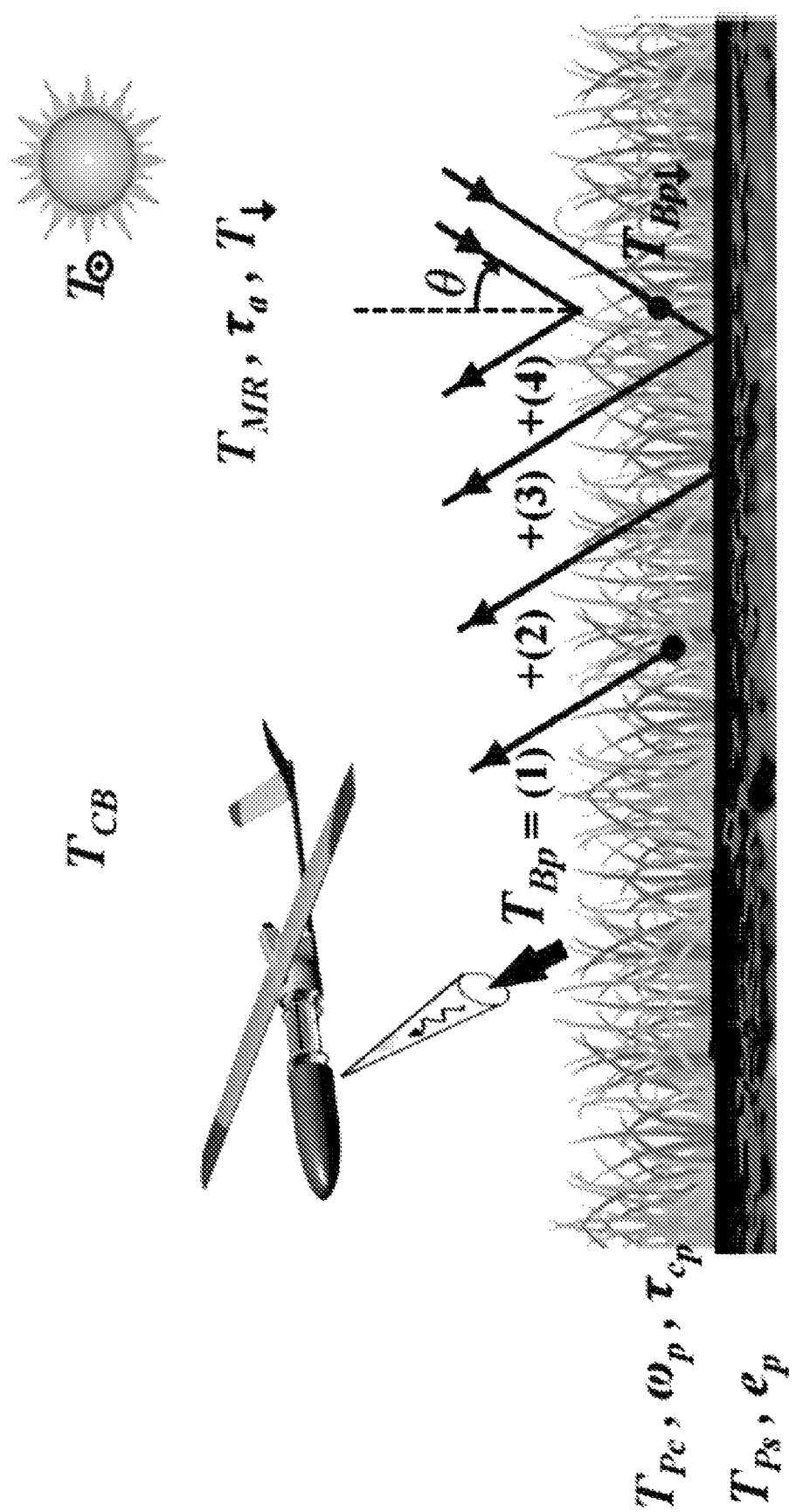
FIG. 9 illustrates radiation streams in the soil-vegetation radiative transfer model of FIG. 8.

FIG. 9 illustrates radiation streams in the SVRT model of FIG. 8. In the τ–ω model, the vegetation optical opacity $\tau_{c_p}(\theta)$ and effective canopy scattering albedo $\omega_p(\theta)$ are used to parametrize radiative transmission, where p is either vertical (v) or horizontal (h) polarization, and θ is the incidence angle from nadir. The thermal emission from a scene consisting of a vegetation layer above an infinite half-space representing the subjacent soil medium may be written as the sum of four terms shown in FIG. 9: (1) the upwelling vegetation emission; (2) upwelling soil emission attenuated by the vegetation canopy; (3) the downwelling canopy and sky emission reflected by the soil and attenuated by the canopy layer; and (4) the downwelling sky emission reflected by the canopy layer. The brightness temperature for polarization p at the canopy top can be expressed as $$T_{B_p} = (1-\omega_p)(1-e^{-\tau_{c_p}})T_{P_c} + e_p e^{-\tau_{c_p}} T_{P_s} + (1-e_p)e^{-\tau_{c_p}} T_{B_p\downarrow} + \omega_p T_\downarrow \qquad (13)$$

where $e_p$ is the soil emissivity at the presumed smooth soil-air interface for polarization p, and $T_{P_c}$ and $T_{P_s}$ are canopy and soil surface physical temperatures. The temperature $T_\downarrow$ is the downwelling sky brightness temperature calculated from the cold space brightness temperature, $T_{CB}$, of 2.73 K with atmospheric attenuation compensation:

$$T_\downarrow(\theta)=(1-e^{-\tau_a \sec\theta})T_{MR}+T_{CB}e^{\tau_a \sec\theta} \qquad (14)$$

where $\tau_a$ is the atmospheric opacity at L-band, and $T_{MR}$ is the atmospheric mean radiating temperature. The downwelling brightness temperature at the soil surface $T_{B_p}^{\ \ 1}$ is expressed as $$T_{B_p\downarrow} = (1-\omega_p)(1-e^{-\tau_{c_p}})T_{P_c}+(1-\omega_p)e^{-\tau_{c_p}} T_\downarrow. \qquad (15)$$

The canopy scattering albedo $\omega_p$ is found to be dependent on vegetation type. The vegetation opacity $\tau_{c_p}$ can be expressed as $$\tau_{c_p}(\theta)=b_p W_v \sec\theta \qquad (16)$$

where $W_v$ is the VWC which can be calculated from vegetation indexes, such as NDVI or NDWI data, and $b_p$ is an empirical coefficient dependent on vegetation type and polarization.

FIG. 10 is a table 1000 of land cover parameters for corrections in the soil-vegetation radiative transfer model of FIG. 8. Soil surface and vegetation canopy physical temperatures may differ by up to ~2-3 K. In addition, the soil physical temperature over the L-band probing depth of ~1-~10 cm may have a difference of several degrees in kelvin. For this disclosure, the soil and vegetation canopy are assumed to have the same physical temperature, that is $T_{P_c} = T_{P_s} = T_P$. Given this assumption, the $T_{B_p}$ can be approximated as $$T_{B_p} = (1 - \omega_p)(1 - e^{-\tau_{c_p}})T_P[1 + (1 - e_p)e^{-\tau_{c_p}}] + \quad (17)$$

$$e_p e^{-\tau_{c_P}} T_P + (1 - \omega_p)(1 - e^{-\tau_{c_p}})e^{-2\tau_{c_P}} T_\downarrow + \omega_p T_\downarrow.$$

Specular soil emissivity may be calculated from soil reflectivity $r_p$ as $e_p = 1 - r_p$. For a smooth soil surface, the Fresnel reflectivities at the soil-air interface may be expressed as $$r_v(\theta) = \left| \frac{\epsilon_s \cos\theta - \sqrt{\epsilon_s - \sin^2(\theta)}}{\epsilon_s \cos\theta + \sqrt{\epsilon_s - \sin^2(\theta)}} \right|^2 \quad (18)$$

$$r_h(\theta) = \left| \frac{\cos\theta - \sqrt{\epsilon_s - \sin^2(\theta)}}{\cos\theta + \sqrt{\epsilon_s - \sin^2(\theta)}} \right|^2 \quad (19)$$

These specular reflectivities may be further modified by surface roughness corrections factors as discussed below.

The MiCo antenna (e.g., antennas 102, 112) used in LDCR synthesizes two broad main beams pointing primarily to the nadir and zenith directions along with minor back lobes pointing in the opposite directions. The LDCR thus observes upwelling and downwelling antenna temperatures $T_U$ and $T_D$, which are the brightness temperatures integrated over these two beams:

$$T_{U/D} = \eta_l \frac{1}{4\pi} \int\int_{2\pi} [G_{vv,U/D} T_{B_V} + G_{hh,U/D} T_{B_h} + \text{Re}\{G_{vh,U/D}\} T_{B_U} \quad (20)$$
$$+ \text{Im}\{G_{hv,U/D}\} T_{B_V}] d\Omega$$
$$+ \eta_l \frac{1}{4\pi} \int\int_{2\pi} [G_{vv,U/D} + G_{hh,U/D} + \text{Re}\{G_{vh,U/D}\}$$
$$+ \text{Im}\{G_{hv,U/D}\}] T_\downarrow d\Omega + (1 - \eta_l) T_{P_A}$$

where $T_{BU}$ and $T_{BV}$ are the upwelling third and fourth Stokes brightness temperature parameters, $G_{vv,U/D}$, $G_{hh,U/D}$, $G_{vh,U/D}$, and $G_{hv,U/D}$ are the MiCo antenna gain matrix elements for the main beam pointing to the nadir/zenith directions (respectively), and $T_{P_A}$ is the physical temperature of the antenna pairs measured by thermistors during flight. The thin layer (~50 m) of atmosphere between the canopy top and UAS may be neglected. Therefore, the downwelling sky brightness temperature defined at canopy top $T_\downarrow$ is used for the integration over the upper hemisphere. In addition, the polarization effects on the downwelling sky brightness temperature $T_\downarrow$ are negligible at L-band.

Based on both simulation and measurement of LDCR MiCo antenna radiation patterns, the $G_{vh,U/D}$ and $G_{hv,U/D}$ terms are smaller in magnitude than $G_{vv,U/D}$ and $G_{hh,U/D}$ by over 20 dB. Additionally, the third and fourth Stokes parameters over typical soil and canopy scenes are far smaller than $T_{B_v}$ and $T_{B_h}$. Therefore, the LDCR antenna temperatures $T_U$ and $T_D$ may be approximated as $$T_{U/D} = \quad (21)$$
$$\eta_l \frac{1}{4\pi} \int\int_{2\pi} [G_{vv,U/D}(\theta, \phi) T_{B_V}(\theta, \phi) + G_{hh,U/D}(\theta, \phi) T_{B_h}(\theta, \phi)] \sin\theta d\theta d\phi +$$
$$\eta_l \frac{1}{4\pi} \int\int_{2\pi} [G_{vv,U/D}(\theta, \phi) + G_{hh,U/D}(\theta, \phi)] T_\downarrow \sin\theta d\theta d\phi + (1 - \eta_l) T_{P_A}$$

The direct solar contribution to the LDCR downwelling antenna temperature $T_D$ is included as follows:

$$T_D = \eta_l \frac{1}{4\pi} \int\int_{2\pi} (G_{vv,D}(\theta, \phi) + G_{hh,D}(\theta, \phi))(T_\odot - T_\downarrow) \sin\theta d\theta d\phi + \quad (21)$$
$$\eta_l \frac{1}{4\pi} \int\int_{2\pi} (G_{vv,D}(\theta, \phi) + G_{hh,D}(\theta, \phi)) T_\downarrow(\theta) \sin\theta d\theta d\phi +$$
$$\eta_l \frac{1}{4\pi} \int\int_{2\pi} [G_{vv,D}(\theta, \phi) T_{B_V}(\theta, \phi) + G_{hh,D}(\theta, \phi) T_{B_h}(\theta, \phi)] \sin\theta d\theta d\phi +$$
$$(1 - \eta_l) T_{P_A}$$

where $T_\odot$ is solar brightness temperature that ranges from $1 \times 10^5$ to $5 \times 10^5$ K at L-band. The solid angle $\omega_\odot$ is calculated from the mean sun-earth distance of $1.496 \times 10^8$ km. The maximum direct solar contribution to the LDCR $T_D$ thus ranges from 1.7 to 9 K, which may not be neglected. The direct solar and downwelling contribution may be operationally compensated based on solar zenith angle, solar cycle, cloud cover condition, UAS pitch and roll angle, and MiCo antenna radiation patterns.

The galactic background contribution to LDCR $T_D$ may be modeled using the galactic noise map at L-band, which may be obtained from sources, such as "Galactic noise and passive microwave remote sensing from space at L-band" by Le Vine et al., IEEE Trans. Geosci. Remote Sens., vol. 42, no. 1, pp. 119-129, January 2004, along with declination and right ascension. This contribution is calculated to be less than 0.5 K to the band-averaged LDCR received downwelling antenna temperature.

Dielectric Mixing Model

Using the soil dielectric mixing model, the effective soil dielectric constant can be written as a function of soil moisture and soil texture $$\epsilon_s = \epsilon_s' - j\epsilon_s'' \quad (23)$$

$$\epsilon_s' = \left[1 + \frac{\rho_b}{\rho_r} \epsilon_r^\alpha + m_v^{\beta'} \epsilon_{f\omega}^{\prime\alpha} - m_v\right]^{1/\alpha} \quad (24)$$

$$\epsilon_s'' = [m_v^{\beta''} \epsilon_{f\omega}^{\prime\prime\alpha}]^{1/\alpha} \quad (25)$$

where the dielectric constant parameter $\epsilon_r$ is calculated as $$\epsilon_r = (1.01 + 0.44\rho_r)^2 - 0.062, \quad (26)$$

and $m_v$ is VSM fraction, $\rho_b = 1.4$ g/cm$^3$ is bulk soil density, and $\rho_r = 2.66$ g/cm$^3$ is density of the solid soil particles. The parameter a is an empirical constant equal to 0.65, and $\beta'$ and $\beta''$ are calculated as $$\beta' = 1.2478 - 0.519S - 0.152C \quad (27)$$

$$\beta'' = 1.33797 - 0.603S - 0.166C \quad (28)$$

where S and C are the fractions of sand and clay, respectively, in the soil. The water dielectric constants $\epsilon_{f\omega}'$ and $\epsilon_{f\omega}''$ are calculated from:

$$\epsilon_{f\omega}' = \epsilon_{\omega\infty} + \frac{\epsilon_{\omega 0} - \epsilon_{\omega\infty}}{1 + (2\pi f \tau_\omega)^2} \qquad (29)$$

$$\epsilon_{f\omega}'' = \frac{2\pi f \tau_\omega (\epsilon_{\omega 0} - \epsilon_{\omega\infty})}{1 + (2\pi f \tau_\omega)^2} + \frac{\sigma_{\text{eff}}}{2\pi f \epsilon_0} \frac{\rho_r - \rho_b}{\rho_r m_v} \qquad (30)$$

where f is the frequency, $\epsilon_{\omega 0}$ is the static dielectric constant and $\epsilon_{\omega\infty}$ is the dielectric constant of water in the high frequency limit, $\tau_\omega$ is relaxation time of water, and $\sigma_{\text{eff}}$ is the soil conductivity calculated as $$\sigma_{\text{eff}} = -1.645 + 1.939\rho_b - 2.25622S + 1.594C \qquad (31)$$

where $\rho_b$ is in g/cm$^3$. The conductivity $\sigma_{\text{eff}}$ depends on soil constitution and bulk density.

SVRT Surface Roughness Correction

For both SMAP and SMOS soil moisture retrieval algorithms, the surface roughness correction is performed based on a semiempirical model referred to as the H-Q-N model. The original H-Q-N model included two primary parameters: $h_{R_p}$ and $Q_R$. An additional parameter $N_{R_p}$ was introduced in subsequent investigations to better model multi-angular and dual-polarization data. Using H-Q-N, the rough soil reflectivities $r_v^*$ and $r_h^*$ for v and h polarizations are calculated as $$r_v^*(\theta) = [(1 - Q_R(\theta))r_v(\theta) + Q_R(\theta)r_h(\theta)]e^{-h_{R_v}(\cos\theta)^{N_{R_v}}} \qquad (32)$$

$$r_h^*(\theta) = [(1 - Q_R(\theta))r_h(\theta) + Q_R(\theta)r_v(\theta)]e^{-h_{R_h}(\cos\theta)^{N_{R_h}}} \qquad (33)$$

where $h_{R_p}$ is a semiempirical surface roughness parameter accounting for both coherent and incoherent scattering effects, $Q_R$ is a polarization mixing parameter, and $N_{R_p}$ is an angular exponent.

The H-Q-N model was incorporated in the LDCR SVRT model under the assumptions of low vegetation cover for which $h_R = h_{R_v} = h_{R_h}$, $Q_R = 0$, and $N_{R_v} = N_{R_h} = 2$. These quantities follow the SMAP algorithm based on an independent VWC data. Given these assumptions, the rough surface soil reflectivities may be calculated as:

$$r_v^*(\theta) = r_v(\theta)e^{-h_R \cos^2(\theta)} \qquad (34)$$

$$r_h^*(\theta) = r_h(\theta)e^{-h_R \cos^2(\theta)} \qquad (35)$$

For the SVRT vegetation correction and surface roughness corrections, the parameters $\omega_p$, $b_p$, and $h_R$ are tabulated as functions of land cover types where $\omega_p$ is assumed to be independent of polarization (i.e., $\omega_h = \omega_v$ in table 1000, FIG. 10). For vegetation covers of corn, wheat, soybean and tall grass, the $\omega_p$, $b_h$, and $b_v$ values are taken to be the best-fit values with an average of three published values used the albedo of corn. The $\omega_p$, $b_h$, and $b_v$ values for land cover types of short grass, bare soil, and forests are set to be the same as used in the current SMAP baseline retrieval algorithm. For grain sorghum and sugar beets, which have been sparsely studied, the values of $\omega_p$ and $b_p$ are set to be the same as for wheat and soybean, respectively. For a built land cover, the scattering albedo $\omega_p$ ranges from 0.4 to 0.95 depending on building surface type (e.g., metal roof and concrete pad), and canopy attenuation is set to infinity to ensure that the soil moisture underneath is effectively immeasurable. The metal-roofed buildings were assigned an albedo of 0.95. The surface roughness correction parameter $h_R$ is set to be the same as used in the current SMAP baseline retrieval algorithm for all land cover types.

$T_P$ Mapping Methods

In the full-domain soil moisture retrieval algorithm, the antenna temperature measurements at all UAS sampling points are related to the soil moisture at all user-defined mapping grid points using an observation matrix. To obtain the observation matrix, surface physical temperature values at the user-defined mapping grid points were optimally determined using an unbiased statistical LMMSE estimator. This estimator mapped from the irregularly sampled flight data grid to a regular mapping grid. Letting $\bar{y}$ be the measured surface physical temperature $T_P$ at the trajectory sample points and x be the true values of $T_P$ at a user-defined rectangular grid of points, the relationship between these quantities can be expressed as $$\bar{y} = \overline{\overline{W}}_f \bar{x} + \bar{n} \qquad (36)$$

where $\bar{n}$ is the instrument observation noise and $\overline{\overline{W}}_f$ is the flight sampling operator. This operator is effectively a sparse matrix wherein only a small number of the $T_P$ values appear in any measured sample. Since the mean values of $\bar{y}$ and x are nonzero the estimated value of $\bar{x}$ is $$\hat{\bar{x}} = \langle \bar{x} \rangle + \overline{\overline{D}}_f (\bar{y} - \langle \bar{y} \rangle) \qquad (37)$$

Based on the orthogonality principle, the operator $\overline{\overline{D}}$ for statistical LMMSE is readily found to be $$\overline{\overline{D}}_f = \overline{\overline{R}}_{xy} \overline{\overline{R}}_{yy}^{-1} \qquad (38)$$

where $\overline{\overline{R}}_{xy}$ is the covariance matrix of $T_P$ for all pairs of user grid and observed sample points while $\overline{\overline{R}}_{yy}$ is the covariance matrix of $T_P$ values at the sample points. To ensure that the LMMSE is unbiased, equation (38) is modified as $$[\overline{\overline{D}}_f, \bar{\lambda}_x] \times \begin{bmatrix} \overline{\overline{R}}_{yy} & \bar{I}_y \\ \bar{I}_y^t & 0 \end{bmatrix} = [\overline{\overline{R}}_{xy}, \bar{I}_x] \qquad (39)$$

where $\bar{\lambda}$ is the Lagrange multiplier vector, and $\bar{I}_\alpha$ is a vector of one of dimension of the associated parameters. There is, in general, one Lagrange multiplier per user grid point. It is assumed that in a local neighborhood of each grid point, the mean values of $T_P$ at the sample points are the same as the mean values of $T_P$ at corresponding user grid point. This assumption is reasonable because the surface physical temperature may be regarded as a gradually spatially varying function.

Accordingly, unbiased LMMSE operator in equation (37) thus becomes $$\hat{\bar{x}} = \overline{\overline{D}}_f \bar{y} \qquad (40)$$

where the mean values are not explicitly needed, and the estimation operator $\overline{\overline{D}}$ is modified from equation (38) as $$\bar{\bar{D}}_f = \bar{\bar{R}}_{xy}\bar{\bar{R}}_{yy}^{-1}\left(\bar{\bar{I}} - \frac{1_x T'_y \bar{\bar{R}}_{yy}^{-1}}{1'_y \bar{\bar{R}}_{yy}^{-1} 1_y}\right) + \frac{1_x T'_y \bar{\bar{R}}_{yy}^{-1}}{1'_y \bar{\bar{R}}_{yy}^{-1} 1_y} \quad (41)$$

The surface physical temperature can be treated as geostatistical data with a spatially homogeneous radial covariance function that may be used to calculate $\bar{\bar{R}}_{xy}$ and $\bar{\bar{R}}_{yy}$. The $T_P$ correlation length depends on land cover type and cloud cover conditions. Land $\bar{\bar{R}}_{yy}$ surface temperature covariance at high spatial resolution (i.e., decameter to meters) has been sparsely studied. In this embodiment, the effective correlation length is chosen to be 85 meters to be consistent with the VSM correlation length used in the LDCR VSM retrieval algorithm 800. Selecting such a limited correlation length ensures that the physical temperature sample and the physical temperature at the estimation point have the same or nearly the same mean values.

The $T_P$ values at user-defined mapping grid points have an estimation error covariance using this unbiased LMMSE estimation method of $$\bar{\bar{R}} = \bar{\bar{R}}_{xx} - \bar{\bar{R}}_{xy}\bar{\bar{R}}_{yy}^{-1}\bar{\bar{R}}_{yx} + \lambda 1'_y \bar{\bar{R}}_{yy}^{-1} 1_y \bar{x}' \quad (42)$$

The unbiased LMMSE error may not be lower than that of biased LMMSE error $$\bar{\bar{R}}_{xx} - \bar{\bar{R}}_{xy}\bar{\bar{R}}_{yy}^{-1}\bar{\bar{R}}_{yx}.$$

The estimated $T_P$ and its estimation error are inputs into the LDCR soil moisture retrieval algorithm 800.

LDCR VSM Retrieval Algorithm

The retrieval of VSM on a user-defined mapping grid from LDCR $T_A \triangleq (T_U - (1-\eta_l)T_{P_A})/\eta_l$ samples uses a physical LMMSE estimator, which has been discussed in the context of remote sensing since the 1970s. With an observed vector $\bar{y}$ being $T_A$ measurements at sample locations on a full observation domain and an unknown vector $\bar{x}$ being the true value of VSM on a user-defined (e.g. rectilinear) grid, the relationship between $\bar{y}$ and $\bar{x}$ may be linearly approximated as $$\bar{y} - \langle\bar{y}\rangle = \bar{W}(\bar{x},\bar{P}) + \bar{n} \equiv (\bar{\bar{W}}_0 + \delta\bar{\bar{W}})(\bar{x} - \langle\bar{x}\rangle) + \bar{n} \quad (43)$$

where $\bar{W}(\bar{x}, \bar{P})$ is a forward observation operator, $\bar{n}$ is observation noise, $\bar{P}$ is a large parameter vector that is further described below and affects the determination of $\bar{W}$, and $\bar{\bar{W}}_0 = \bar{\bar{W}}|_{\langle\bar{x},\bar{P}\rangle}$ is the value of the Jacobian $(\partial\bar{W}/\partial\bar{x})$ at the expected value of $\bar{x}$ and $\bar{P}$.

The operator $\bar{W}$ is a weakly nonlinear function of the expected vegetation opacity and surface roughness, soil type and texture parameters. It may also depend on the antenna radiation pattern and a position vector from each sampling point to each corresponding mapping point. A random component $\delta\bar{\bar{W}}$ results from uncertainties in all parameters and includes small nonlinear terms in the radiative transfer model $$\delta\bar{W} = \sum_i \frac{\partial \bar{W}}{\partial \bar{P}_i}\bigg|_{\langle\bar{P}_i\rangle}\delta\bar{P}_i + \frac{1}{2}\frac{\partial \bar{W}}{\partial \bar{x}}\bigg|_{\langle\bar{x}\rangle}(\bar{x} - \langle\bar{x}\rangle) \quad (44)$$

where the parameters in $\bar{P}$ fall into two categories: geophysical measurements and empirical parameters. Geophysical measurements include VWC $W_v$, surface physical temperature $T_P$, and soil sand and clay percentages S and C. Empirical parameters include $b_h$, $b_v$, $\omega_p$, and surface roughness parameter $h_R$.

Since the mean values of $\bar{y}$ and $\bar{x}$ are nonzero, the estimated value of $\bar{x}$ is $$\hat{\bar{x}} = \bar{\bar{D}}_S(\bar{y} - \langle\bar{y}\rangle) + \langle\bar{x}\rangle \quad (45)$$

where the physical LMMSE operator $\bar{\bar{D}}_S$ is $$\bar{\bar{D}}_S = \bar{\bar{R}}_{xx}\bar{\bar{W}}'_0(\bar{\bar{W}}_0\bar{\bar{R}}_{xx}\bar{\bar{W}}'_0 + \langle\delta\bar{\bar{W}}(\bar{x}-\langle\bar{x}\rangle)(\bar{x}-\langle\bar{x}\rangle)'\delta\bar{\bar{W}}^t\rangle + \bar{\bar{R}}_{nn})^{-1} \quad (46)$$

The term $\bar{\bar{R}}_{xx}$ is spatial covariance matrix of soil moisture on the user grid and $\bar{\bar{R}}_{nn}$ is observation error covariance matrix that is only dependent on the LDCR radiometric noise. When the antenna temperature errors at different sampling points are uncorrelated $\bar{\bar{R}}_{xx}$ may be the same as $\Delta T_{rms,s}^2$, $\bar{\bar{R}}_{xx} = \Delta T_{rms,s}^2$.

A modified observation error covariance matrix $\bar{\bar{R}}'_{nn}$ that incorporate all uncertain quantities in equation (46) may then be defined as $\bar{\bar{R}}'_{nn} = \langle \delta\bar{\bar{W}} \langle\bar{x}-\langle\bar{x}\rangle\rangle(\bar{x}-\langle\bar{x}\rangle)' \delta\bar{\bar{W}}^t\rangle + \bar{\bar{R}}_{nn}$. This modified covariance accounts for uncertainties in vegetation and surface roughness correction parameter, temperature estimation error at the mapping grid point, soil texture information, observation operator nonlinearities, and radiometric measurement noise, as may be calculated as:

$$\begin{aligned}\bar{\bar{R}}'_{nn} = &\left\langle\frac{\delta\bar{W}}{\delta W_v}\bigg|_{\langle\bar{W}_v\rangle}\delta W_v(\bar{x}-\langle\bar{x}\rangle)(\bar{x}-\langle\bar{x}\rangle)'\left(\frac{\delta\bar{W}}{\delta W_v}\bigg|_{\langle\bar{W}_v\rangle}\delta W_v\right)^t\right\rangle \\ &+\left\langle\frac{\delta\bar{W}}{\delta T_P}\bigg|_{\langle\bar{T}_P\rangle}\delta T_P(\bar{x}-\langle\bar{x}\rangle)(\bar{x}-\langle\bar{x}\rangle)'\left(\frac{\delta\bar{W}}{\delta T_P}\bigg|_{\langle\bar{T}_P\rangle}\delta T_P\right)^t\right\rangle \\ &+\left\langle\frac{\delta\bar{W}}{\delta S}\bigg|_{\langle\bar{S}\rangle}\delta S(\bar{x}-\langle\bar{x}\rangle)(\bar{x}-\langle\bar{x}\rangle)'\left(\frac{\delta\bar{W}}{\delta S}\bigg|_{\langle\bar{S}\rangle}\delta S\right)^t\right\rangle \\ &+\left\langle\frac{\delta\bar{W}}{\delta C}\bigg|_{\langle\bar{C}\rangle}\delta C(\bar{x}-\langle\bar{x}\rangle)(\bar{x}-\langle\bar{x}\rangle)'\left(\frac{\delta\bar{W}}{\delta C}\bigg|_{\langle\bar{C}\rangle}\delta C\right)^t\right\rangle \\ &+\left\langle\frac{\delta\bar{W}}{\delta b_h}\bigg|_{\langle\bar{b}_h\rangle}\delta b_h(\bar{x}-\langle\bar{x}\rangle)(\bar{x}-\langle\bar{x}\rangle)'\left(\frac{\delta\bar{W}}{\delta b_h}\bigg|_{\langle\bar{b}_h\rangle}\delta b_h\right)^t\right\rangle \\ &+\left\langle\frac{\delta\bar{W}}{\delta b_v}\bigg|_{\langle\bar{b}_v\rangle}\delta b_v(\bar{x}-\langle\bar{x}\rangle)(\bar{x}-\langle\bar{x}\rangle)'\left(\frac{\delta\bar{W}}{\delta b_v}\bigg|_{\langle\bar{b}_v\rangle}\delta b_v\right)^t\right\rangle \\ &+\left\langle\frac{\delta\bar{W}}{\delta\omega_p}\bigg|_{\langle\bar{\omega}_p\rangle}\delta\omega_p(\bar{x}-\langle\bar{x}\rangle)(\bar{x}-\langle\bar{x}\rangle)'\left(\frac{\delta\bar{W}}{\delta\omega_p}\bigg|_{\langle\bar{\omega}_p\rangle}\delta\omega_p\right)^t\right\rangle \\ &+\left\langle\frac{\delta\bar{W}}{\delta h_R}\bigg|_{\langle\bar{h}_R\rangle}\delta h_R(\bar{x}-\langle\bar{x}\rangle)(\bar{x}-\langle\bar{x}\rangle)'\left(\frac{\delta\bar{W}}{\delta h_R}\bigg|_{\langle\bar{h}_R\rangle}\delta h_R\right)^t\right\rangle \\ &+\left\langle\frac{\delta\bar{W}}{\delta\bar{x}}\bigg|_{\langle\bar{x}\rangle}(\bar{x}-\langle\bar{x}\rangle)(\bar{x}-\langle\bar{x}\rangle)(\bar{x}-\langle\bar{x}\rangle)'\left(\frac{\delta\bar{W}}{\delta\bar{x}}\bigg|_{\langle\bar{x}\rangle}(\bar{x}-\langle\bar{x}\rangle)\right)^t\right\rangle \\ &+\Delta T_{rms,s}^2 \bar{\bar{I}}\end{aligned} \quad (47)$$

with the assumption that all parameter deviations are uncorrelated.

Spatial VSM Covariance

The covariance of soil moisture at any two mapping grid points is in general nonzero. This is particularly true for cropland areas managed using uniform field irrigation practices. One way to calculate the VSM covariance matrix is to use a stationary spatial covariance function:

$$\bar{R}_{xx}(\bar{r}_1, \bar{r}_2) = \begin{cases} \sigma_x^2 \left(1 - \frac{3}{2}\left(\frac{|\bar{r}_1 - \bar{r}_2|}{a}\right) + \frac{1}{2}\left(\frac{|\bar{r}_1 - \bar{r}_2|}{a}\right)^3\right) \\ \text{if } |\bar{r}_1 - \bar{r}_2| \le a \\ 0, \text{ if } |\bar{r}_1 - \bar{r}_2| > a \end{cases}, \quad (48)$$

where $\sigma_x^2$ is VSM variance. In the following soil moisture retrieval performance calculations, a value of $\sigma_{x_i}$ of 8.3% is used for all mapping grid points. This value of $\sigma_{x_i}$ presumes a Gaussian VSM distribution with 6-sigma range from 0% to 50% VSM. Equation (48) is effectively a VSM semi-variogram dependent only on the separation distance between two points. The value of a depends on crop land management practices, soil texture, and topography, and may also depend on the VSM itself. For calculations herein, a is set to be approximately 85 meters based on a least square fit to an empirical correlation function.

For crop land, a modified land section covariance (LSC) function based on managed land sections (e.g., irrigated or tilled) can further be specified. In this case, covariance is calculated using equation (48) when $\bar{r}_1$ and $\bar{r}_2$ are within the same crop section, that is, for example, for land with the same vegetation cover type, irrigation, tillage, and fertilization practices, and general cultivation state. When $\bar{r}_1$ and $\bar{r}_2$ are in different sections, the covariance is zero.

A third method for generating the VSM covariance matrix is to assume that the VSM correlation is unity within the same crop section and thus $R_{xx}(\bar{r}_1,\bar{r}_2)=\sigma_x^2$, whereas when $\bar{r}_1$ and $\bar{r}_2$ are in different sections the covariance is zero. The above is effectively a uniform correlation LSC (UCLSC) model. By enforcing unity correlation, the resulting VSM estimate is constant within any given crop section. While this condition detracts from identifying subsection spatial variations in VSM, it also results in a more accurate section-averaged value of VSM. The improved accuracy results from the weighting of all available LDCR observations in determining a single section-averaged VSM value.

Spatial VSM $T_A$ Operator $\bar{W}_0$

To determine the linear observation operator $\bar{W}_0$, which relates the $T_A$ at any sampling point to VSM at any user-defined mapping point, the LDCR measured $T_A$ at the $k^{th}$ sampling point, $T_{A_k}$, may be rewritten from the integral equation (20) to second order in VSM as $$T_{A_k} = T_{A_{k,s}} + \sum_{i=1}^{M} T_{A_{k,i}} \cong \qquad (49)$$

$$T_{A_{k,s}} + \sum_{i=0}^{M} \left( W_{0_{k,i}}(m_{v_i} - \langle m_{v_i}\rangle) + W'_{0_{k,i}}(m_{v_i} - \langle m_{v_i}\rangle)^2 + \langle T_{A_{k,i}}\rangle \right)$$

where $T_{A_{k,i}}$ is the antenna temperature contribution, $\langle T_{A_{k,i}}\rangle$ is its mean value at the i-th user-defined mapping point, $m_{v_i}$ and $\langle m_{v_i}\rangle$ are the VSM and its mean value, respectively, at this mapping point, M is the total number of user mapping grid points, and $T_{A_{k,s}}$ is the combined sky and solar downwelling antenna temperature contribution. The values of $T_{A_{k,i}}$ and $T_{A_{k,s}}$ can be calculated from equation (20) separately as $$T_{A_{k,i}} = \qquad (50)$$

$$\frac{1}{4\pi} \int\int_{\delta\theta_{k,i},\delta\phi_{k,i}} (G_{vv,U}(\theta,\phi)T_{B_v}(\theta,\phi) + G_{hh,U}(\theta,\phi)T_{B_h}(\theta,\phi))\sin\theta d\theta d\phi$$

$$T_{A_{k,s}} = \frac{1}{4\pi} \int\int_{2\pi} (G_{vv,U}(\theta,\phi) + G_{hh,U}(\theta,\phi))T_\downarrow(\theta,\phi)\sin\theta d\theta d\phi + \qquad (51)$$

$$\frac{1}{4\pi} \int\int_{\Omega\odot} (G_{vv,U}(\theta,\phi) + G_{hh,U}(\theta,\phi))(T_\odot - T_\downarrow)\sin\theta d\theta d\phi$$

where $\delta\theta_{k,i}$ and $\delta\phi_{k,i}$ are determined by the vector between the i-th user mapping point and the k-th sampling point along with UAS flight direction, altitude, and pitch and roll angle at the k-th sampling point.

Figure 11:
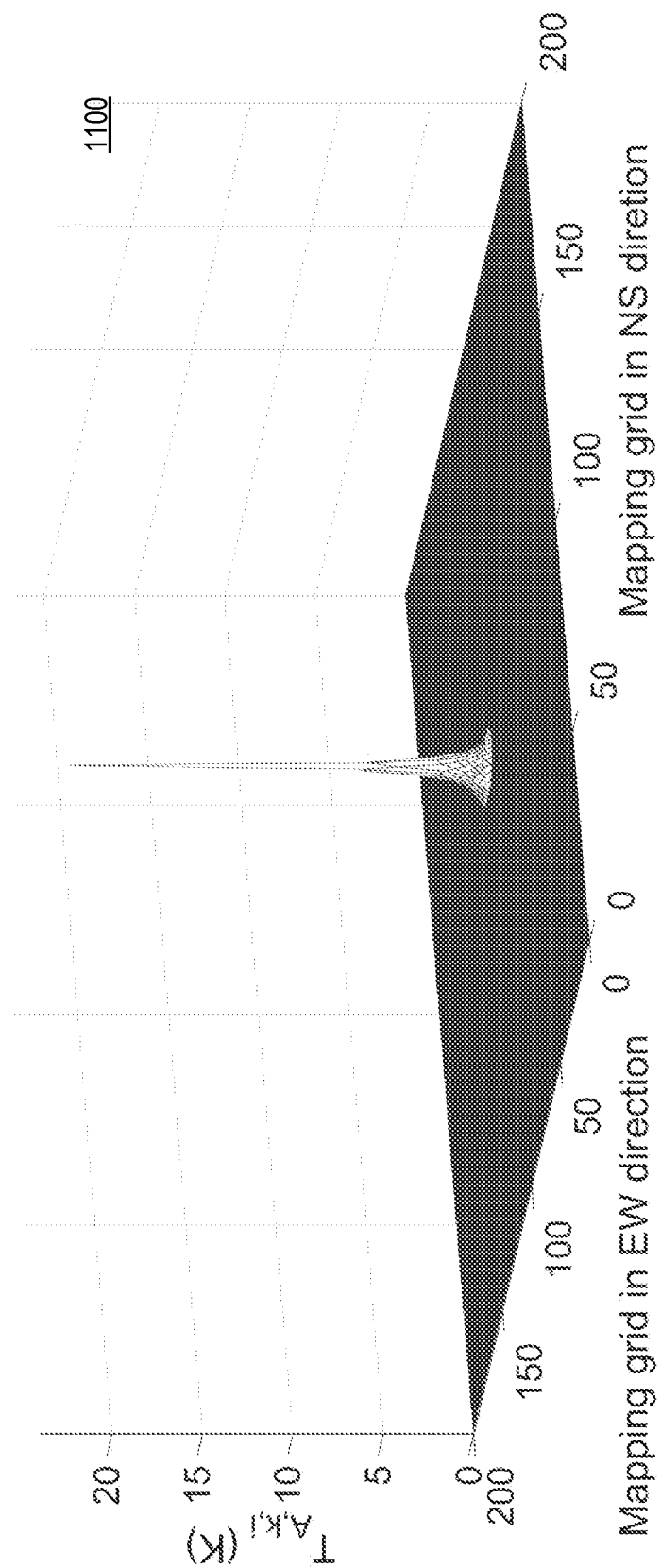
FIG. 11 is a plot illustrating antenna temperature contribution from all mapping grid points in the volumetric soil moisture retrieval algorithm of FIG. 8.
Figure 12:
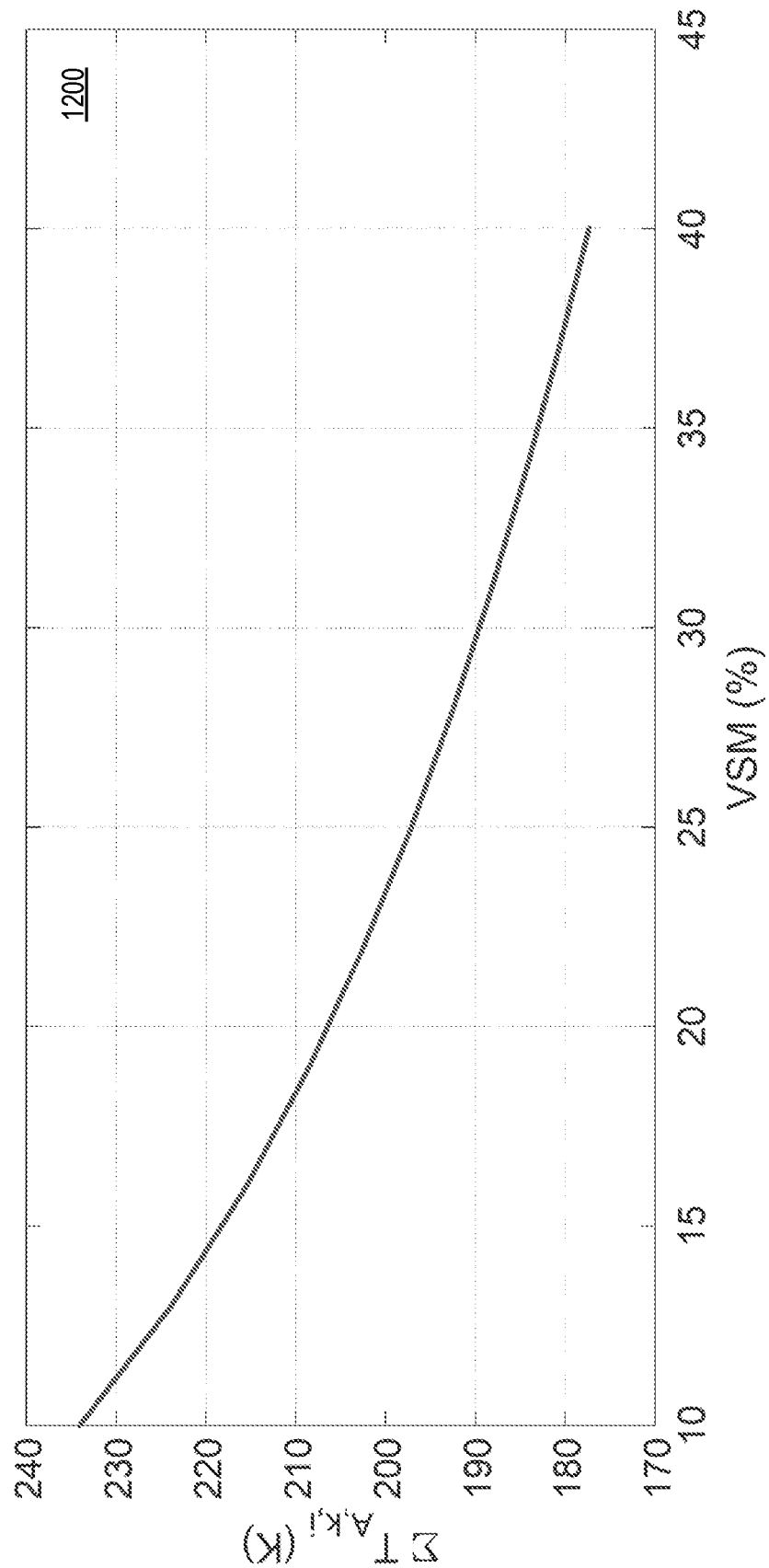
FIG. 12 is a plot illustrating antenna temperature contribution of FIG. 11 as a function of volumetric soil moisture.

FIG. 11 is a plot 1100 illustrating antenna temperature contribution from all mapping grid points in the VSM retrieval algorithm of FIG. 8. Plot 1100 shows a calculated values of $T_{A_{800,i}}$ using a test flight data, with the 800th LDCR sampling point, assuming 298 K for $T_P$, corn vegetation cover, and VSM of 25%. Plot 1100 shows essentially the spatial sensitivity pattern of the UAS sensor. More than 95% percent of the antenna temperature contribution is from mapping points located within a circle of ~50 meters diameter. This range is consistent with LDCR MiCo antenna footprint size at UAS flight altitude of ~50 meters and the LDCR MiCo antenna 3-dB beamwidth of ~45°. FIG. 12 is a plot 1200 illustrating antenna temperature contribution of FIG. 11 as a function of VSM. Plot 1200 shows the sum of antenna temperature contribution from all mapping points, $$\sum_{i=1}^{M} T_{A_{k,i}},$$

for various VSM values. Plot 1200 shows the sum decreasing from 235 to 178 K with increasing VSM from 10% to 40%. This calculation indicates a dynamic range of 95 K over the full 0%-50% VSM range.

In equation (49), values of $W_{0_{k,i}}$ and $W_{0_{k,i}}'$ that are determined using a second order polynomial fit can be plotted for the $k=800^{th}$ sampling point as well. FIG. 13 shows plots 1310 and 1320 illustrating fitting parameters for the antenna temperature contributions in the algorithm of FIG. 8. Plots 1310 and 1320 show second-order polynomial fit parameters $W_{0_{k,i}}$ and $W_{0_{k,i}}'$, respectively, for the antenna temperature contributions for a given sampling point, which is $k=800^{th}$ sampling point. Plot 1310 shows negative $W_{0_{k,i}}$ values with largest minimum value of $\sim-20$ K/100% while plot 1320 shows the parameter $W_{0_{k,i}}'$ having a maximum value of ~42 K/(100%)². The $W_{k,j}$ nonlinearity is accounted for as a model error in equation (43) as $$W'_{0_{k,i}} = (1/2)(\partial W_{k,i}/\partial m_{v_i})\Big|_{\langle m_{v_i}\rangle},$$

and $(\partial W_{k,i}/\partial m_{v_j})=0$ when $i \ne j$. The second-order component in equation (49) is less than 2% of the antenna temperature contribution for most of the mapping grid.

The partial derivatives of $\bar{W}$ with respect to $\bar{P}$ are determined similarly. Variations in any parameter are used to calculate the value of $W_{k,i}$, and partial derivatives ($\partial W_{k,i}/$ $\partial P_i$) are then determined using a linear fit of $W_{k,i}$ to variations in any parameter $P_i$ while keeping the other parameters fixed. Similarly, values of $(\partial W_{k,i}/\partial P_j)$ are set to zero so that the estimation of $\overline{P}_i$ at the i-th mapping point only effects the determination of $\overline{W}$ relative to i-th mapping point. Once $\overline{W}_0$ and $\delta \overline{W}$ are determined, the LDCR VSM at all mapping grid points may be estimated using equations (43)-(46).

VSM Estimation Error

The VSM estimation error covariance for the full mapping grid using the physical LMMSE is calculated as $$\overline{\overline{R}}_{ee} = (\overline{\overline{I}} - \overline{\overline{D}}_s \overline{\overline{W}}_0) \overline{\overline{R}}_{xx} (\overline{\overline{I}} - \overline{\overline{D}}_s \overline{\overline{W}}_0)^t + \overline{\overline{D}}_s \overline{\overline{R}}'_{nn} \overline{\overline{D}}'_s \quad (52)$$

This estimation error depends on $\Delta T_{rms,s}$, as described above in reference to equation (46), along with the estimation errors of all model parameters. It is assumed that for any parameter P at any mapping point, the estimation error includes estimation bias and variation:

$$\delta P = \beta_{e_p} + \delta_{e_p} \quad (53)$$

When the bias correlates within a crop land section, $\beta_{e_p}$ has a uniform value within each such section. The parameter error variations $\delta_{e_p}$ at different mapping grid points are assumed to be uncorrelated, with standard deviation $\sigma_{e_p}$. Considering the empirical parameters in table 1000 in FIG. 10, it is reasonable to assume $\sigma_{e_p}$ to be zero, but not $\beta_{e_p}$. In addition to these assumptions, assuming VSM process variations are uncorrelated, the observation error covariance matrix consequently becomes conservatively bounded by $$\overline{\overline{R}}'_{nn} = \sum_{i=1}^{M} \sigma^2_{e_{W_{v_i}}} \sigma^2_x \left( \frac{\delta \overline{W}}{\delta W_{v_i}} \left( \frac{\delta \overline{W}}{\delta W_{v_i}} \right)^t \right) + \sum_{i=1}^{M} \sigma^2_{e_{T_{P_i}}} \sigma^2_x \left( \frac{\delta \overline{W}}{\delta T_{P_i}} \left( \frac{\delta \overline{W}}{\delta T_{P_i}} \right)^t \right)$$

$$+ \sum_{i=1}^{M} \sigma^2_{e_{S_i}} \sigma^2_x \left( \frac{\delta \overline{W}}{\delta S_i} \left( \frac{\delta \overline{W}}{\delta S_i} \right)^t \right) + \sum_{i=1}^{M} \sigma^2_{e_{C_i}} \sigma^2_x \left( \frac{\delta \overline{W}}{\delta C_i} \left( \frac{\delta \overline{W}}{\delta C_i} \right)^t \right)$$

$$+ \sum_{l=1}^{L} \beta^2_{e_{W_{v_l}}} \sigma^2_x \left( \frac{\delta \overline{W}}{\delta W_{v_l}} \overline{1}_{M_l} \overline{1}^t_{M_l} \left( \frac{\delta \overline{W}}{\delta W_{v_l}} \right)^t \right)$$

$$+ \sum_{l=1}^{L} \beta^2_{e_{T_{P_l}}} \sigma^2_x \left( \frac{\delta \overline{W}}{\delta T_{P_l}} \overline{1}_{M_l} \overline{1}^t_{M_l} \left( \frac{\delta \overline{W}}{\delta T_{P_l}} \right)^t \right)$$

$$+ \sum_{l=1}^{L} \beta^2_{e_{S_l}} \sigma^2_x \left( \frac{\delta \overline{W}}{\delta S_l} \overline{1}_{M_l} \overline{1}^t_{M_l} \left( \frac{\delta \overline{W}}{\delta S_l} \right)^t \right)$$

$$+ \sum_{l=1}^{L} \beta^2_{e_{C_l}} \sigma^2_x \left( \frac{\delta \overline{W}}{\delta C_l} \overline{1}_{M_l} \overline{1}^t_{M_l} \left( \frac{\delta \overline{W}}{\delta C_l} \right)^t \right)$$

$$+ \sum_{l=1}^{L} \beta^2_{e_{b_{h_l}}} \sigma^2_x \left( \frac{\delta \overline{W}}{\delta b_{h_l}} \overline{1}_{M_l} \overline{1}^t_{M_l} \left( \frac{\delta \overline{W}}{\delta b_{h_l}} \right)^t \right)$$

$$+ \sum_{l=1}^{L} \beta^2_{e_{b_{v_l}}} \sigma^2_x \left( \frac{\delta \overline{W}}{\delta b_{v_l}} \overline{1}_{M_l} \overline{1}^t_{M_l} \left( \frac{\delta \overline{W}}{\delta b_{v_l}} \right)^t \right)$$

$$+ \sum_{l=1}^{L} \beta^2_{e_{\omega_{P_l}}} \sigma^2_x \left( \frac{\delta \overline{W}}{\delta \omega_{P_l}} \overline{1}_{M_l} \overline{1}^t_{M_l} \left( \frac{\delta \overline{W}}{\delta \omega_{P_l}} \right)^t \right)$$

$$+ \sum_{l=1}^{L} \beta^2_{e_{h_{R_l}}} \sigma^2_x \left( \frac{\delta \overline{W}}{\delta h_{R_l}} \overline{1}_{M_l} \overline{1}^t_{M_l} \left( \frac{\delta \overline{W}}{\delta h_{R_l}} \right)^t \right) + \frac{1}{4} \sum_{i=1}^{M} 3 \sigma^4_{x_i} \left( \frac{\delta \overline{W}}{\delta x_i} \left( \frac{\delta \overline{W}}{\delta x_i} \right)^t \right)$$

$$+ \Delta T^2_{rms,s} \overline{\overline{I}}$$

where i is mapping point number, l is land section number, L is the total number of land sections, $M_l$ is the total number of mapping points in the l-th land section, and the following variances and biases are:

$$\sigma^2_{e_{W_{v_i}}}$$

is the VWC error variance at the i-th mapping grid point, $\beta_{e_{W_{v_l}}}$ is the VWC bias in the lth land section, $$\frac{\partial \overline{W}}{\partial W_{v_l}}$$

is the partial derivative of $\overline{W}$ with respect to VWC $W_v$ at all mapping grid points in the l-th land section, and $$\frac{\partial \overline{W}}{\partial W_{v_l}} \overline{1}_{M_l} = \frac{\partial \overline{W}}{\partial W_{v_1}} + \frac{\partial \overline{W}}{\partial W_{v_2}} + \ldots + \frac{\partial \overline{W}}{\partial W_{v_{M_l}}}$$

is a matrix of size of N×M where N is the total number of sampling points. Spatial indexing using i and l is necessary since the values of parameter error variances at different mapping points or error biases in different land sections are not necessarily the same. The uncorrelated estimation error covariances have smaller effects on VSM estimation error compared with the bias error. In an embodiment, this smaller effect is a result of the application of the full-domain retrieval algorithm in that the observation operator $\overline{\overline{W}}_0$ relates $T_A$ measurements at each sampling grid point to VSM at ~150 mapping grid points, and the VSM at each single mapping grid point is estimated from UAS measurements at ~14 sampling points using the estimator $\overline{\overline{D}}_s$. Thus, the estimation error variance at each single mapping grid point is significantly reduced by the full-domain retrieval method. However, errors due to parameter bias are not reduced by this averaging process. This full-domain retrieval algorithm and estimation error are validated using experimental data described below in experimental demonstration cases.

To summarize, an LDCR high spatial resolution soil moisture mapping algorithm using the SVRT model and LMMSE full domain retrieval method is disclosed above. The SVRT-based VSM estimation method translates radiometric measurements at all sampling points to soil moisture at all user mapping points, and the VSM is retrieved based on the full-domain relations. Vegetation and surface roughness corrections are also included in the SVRT model, and accounted for in the retrieval algorithm.

Additionally, the slope and orientation of the land surface may affect the LDCR antenna temperature measurements. For example, in a field experiment, the effect of the slope of land surface led to a 10-15 K difference in antenna temperature measurements, which resulted in 5-10% error in the calculated VSM. To remedy the effect of the non-uniform land surface in a user-defined mapping grid, LDCR may be equipped with a sensor that provides elevation data for the land surface. For example, the sensor may be a camera, such as an Altum mapping camera. From the elevation data along with the orientation of the LDCR, for example the pitch angle of the UAS, the angle of incidence and reflection of the thermal emission may be adjusted in the VSM calculation. Advantageously, when the elevation sensor is a camera capable of further providing NDVI, effectively a greenness of the user-defined mapping grid, or if LDCR is further equipped with a NDVI sensor, such information may provide subscale vegetation cover information, which may be used as a correction for the VSM calculation.

Experimental Demonstration

Flight tests of a LDCR integrated in a UAS (e.g., airborne LDCR system 500, FIG. 5), where the embodiment of LDCR was a LDCR Rev. A and the UAS was a Tempest modified by Black Swift Technologies LLC, were performed at the Canton, Oklahoma Soilscape site and Irrigation Research Foundation (IRF) in Yuma, Colorado.

Figure 14:
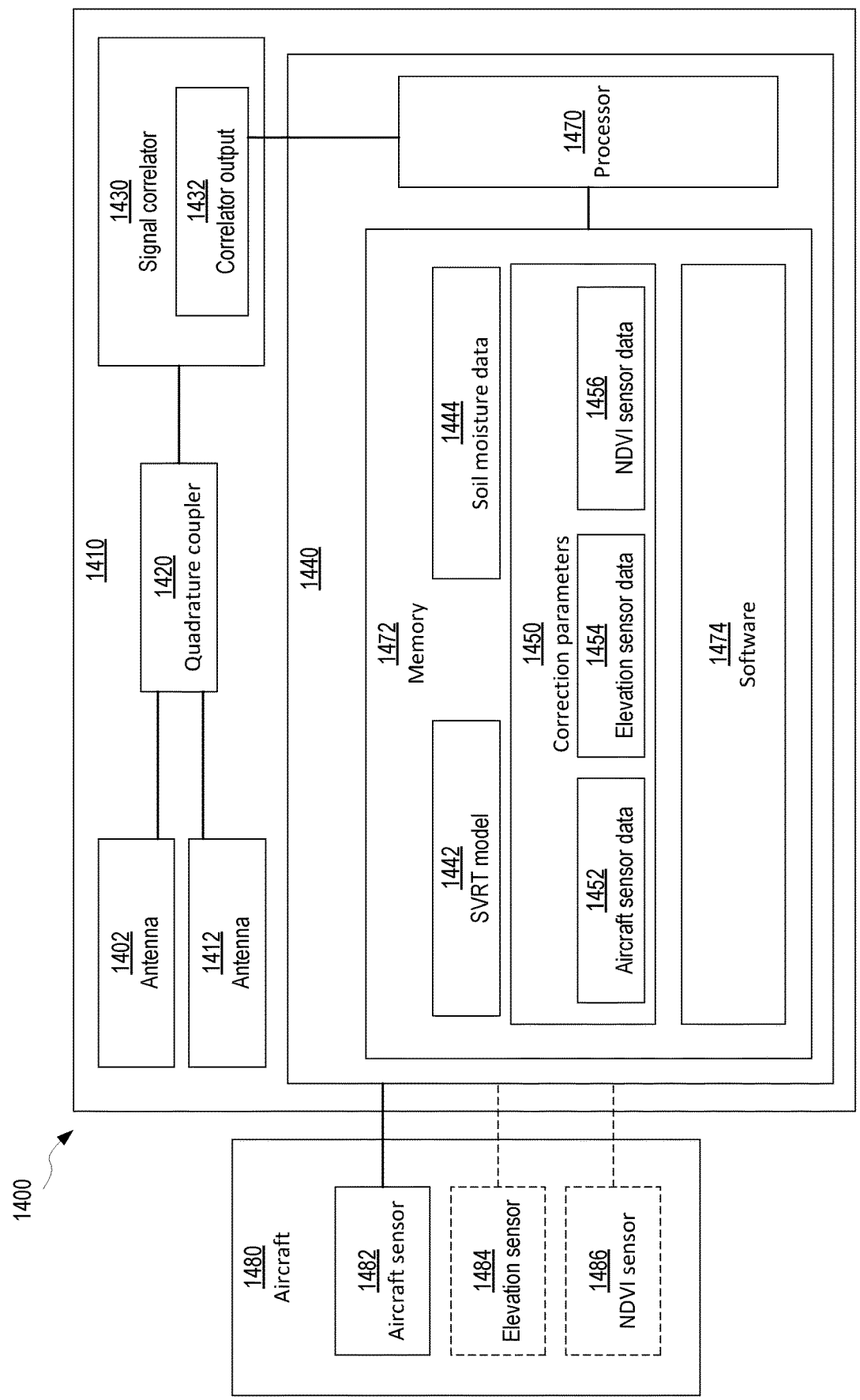
FIG. 14 is a block diagram of a system for determining soil moisture of a scene that includes an LDCR integrated in an aircraft, in an embodiment.

FIG. 14 is a block diagram of a system 1400 for determining soil moisture of a scene that includes an LDCR 1410 integrated in an aircraft 1480. LDCR 1410 is an example of LDCR 200. Aircraft 1480 may be a UAS, an example of UAS 510. System 1400 is an example of airborne LDCR system 500. An embodiment of system 1400 was used in the flight tests. Aircraft 1480 includes an aircraft sensor 1482. Aircraft sensor 1482 may include positional sensors that detect location and orientation, such as pitch and roll angles, of the aircraft. Aircraft 1480 may also include an elevation sensor 1484 that detects the elevation of the surface in the user-defined grid. The elevation data may be used, in part, to calculate surface characteristics, such as slope and orientation. Aircraft 1480 may also include an NDVI sensor 1486 that provides the vegetation cover information. Elevation sensor 1484 and NDVI sensor 1486, if available, are coupled with and provide data to LDCR 1410.

LDCR 1410 includes a first passive microwave antenna 1402 having a nadir-pointing first main lobe, a second passive microwave antenna 1412 having a zenith-pointing first main lobe. Antennas 1402 and 1412, which are examples of antenna 102 and 112, are vertically separated by a quarter of a resonant wavelength of the two antennas. LDCR 1410 also includes a quadrature coupler 1420 and a signal correlator 1430. Quadrature coupler 1420 is an example of signal coupler 120, FIG. 1, and signal correlator 1430 is an example of signal correlator 130. Quadrature coupler 1420 has a first input connected to an output of antenna 1402 and a second input connected to an output of antenna 1412. Signal correlator 1430 is coupled to an output of quadrature coupler 1420, and outputs a correlator output 1432, an example of output voltage 132, linearly related to a difference between the first and the second inputs of quadrature coupler 1420.

LDCR 1410 further includes a processing circuitry 1440, which is an example of processing circuitry 140, FIG. 1. Processing circuitry 1440 includes a processor 1470 and a memory 1472. Memory 1472 may be transitory and/or non-transitory and may include one or both of volatile memory (e.g., SRAM, DRAM, computational RAM, other volatile memory, or any combination thereof) and non-volatile memory (e.g., FLASH, ROM, magnetic media, optical media, other non-volatile memory, or any combination thereof). Part or all of memory 1472 may be integrated into processor 1470. Memory 1472 stores non-transitory computer-readable instructions as software 1474. When executed by processor 1470, software 1474 causes processor 1470 to implement the functionality of determining soil moisture as described herein. Software 1474 may be or may include firmware. Processor 1470 may include a plurality of processors, each performing one or more steps of determining soil moisture. Processor 1470 may also implement additional steps, such as the calibration described herein.

Memory 1472 additionally includes a SVRT model 1442, a soil moisture data 1444, and correction parameters 1450. Correction parameters 1450 includes memory locations for an aircraft sensor data 1452, an elevation sensor data 1454, and an NDVI sensor data 1456, which stores data from sensors 1482, 1484, and 1486, if available, in aircraft 1480. SVRT model 1442 implements algorithm 800 of FIG. 8. Processor 1470 uses SVRT model 1442 along with corrections using at least partially from sensor data 1452, 1454, and 1456 to calculate soil moisture and may store the calculated results in soil moisture data 1444. The calculated soil moisture may be further adjusted by processor 1470, an external post-processor, or manually based on at least partially the further corrections described hereinbelow.

The LDCR antenna temperature $T_A$ and surface physical temperature $T_P$ were measured as primary inputs to map retrieved soil moisture over regions of size of approximately one-quarter of a section. However, there were several challenging aspects when using an airborne LDCR system L-band data for retrieving volumetric soil moisture (VSM). Those challenges included (i) UAS flight lines were inherently irregular due to wind variations, line of site flight, and obstacle avoidance requirements, and other operational considerations; (ii) the desired regular mapping grid was more dense than typical flight patterns would permit; and (iii) the vegetation cover was often inhomogeneous at the spatial scale of the available observations. To remedy these unique spatial attributes, a new high spatial resolution soil moisture mapping algorithm was developed specifically for sparse irregular observations of an airborne LDCR system. The LDCR calibration method, LDCR VSM retrieval algorithm, field campaigns, $T_P$ and VSM maps, and intercomparisons with in situ soil moisture data and irrigation records are detailed herein.

Field experiment in Canton, Oklahoma

Two successful field experiments were performed at the Canton Soilscape site, the Canton site hereinafter, in September 2015. FIG. 15 illustrates a flight path of an embodiment of airborne LDCR system 500 of FIG. 5 and the measured vegetation water content of a surveyed area at the Canton site. FIG. 15 includes maps 1510, 1520 and 1530. Map 1510 illustrates a flight trajectory 1512 for the September $8^{th}$ and $9^{th}$ sorties overlayed on a rectangular area of approximately 32 acres. On these dates, Tempest was flown in serpentine trajectories 1512 with North-South (NS) flight lines. During the flight on September 8 with an 11:30 A.M. takeoff, cloud cover was ~60% and the ambient temperature was ~300 K. The test site was covered by dry green grass of ~7 inches height. On September 9 with an 8:00 A.M. take off, the cloud cover was ~100% and the ambient temperature was ~293 K. The grass was lightly moistened with dew. No precipitation was observed on either test day. Each flight was approximately 16 minutes in duration. Map 1530 illustrates soil type of land cover for the area. The user-defined mapping grid size was ~5×5 meters. Map 1520 shows VWC for the same area generated using Landsat 7 Enhanced Thematic Mapper Plus (ETM+) data observed on September 5 with a spatial resolution of 30 meters.

Figure 16:
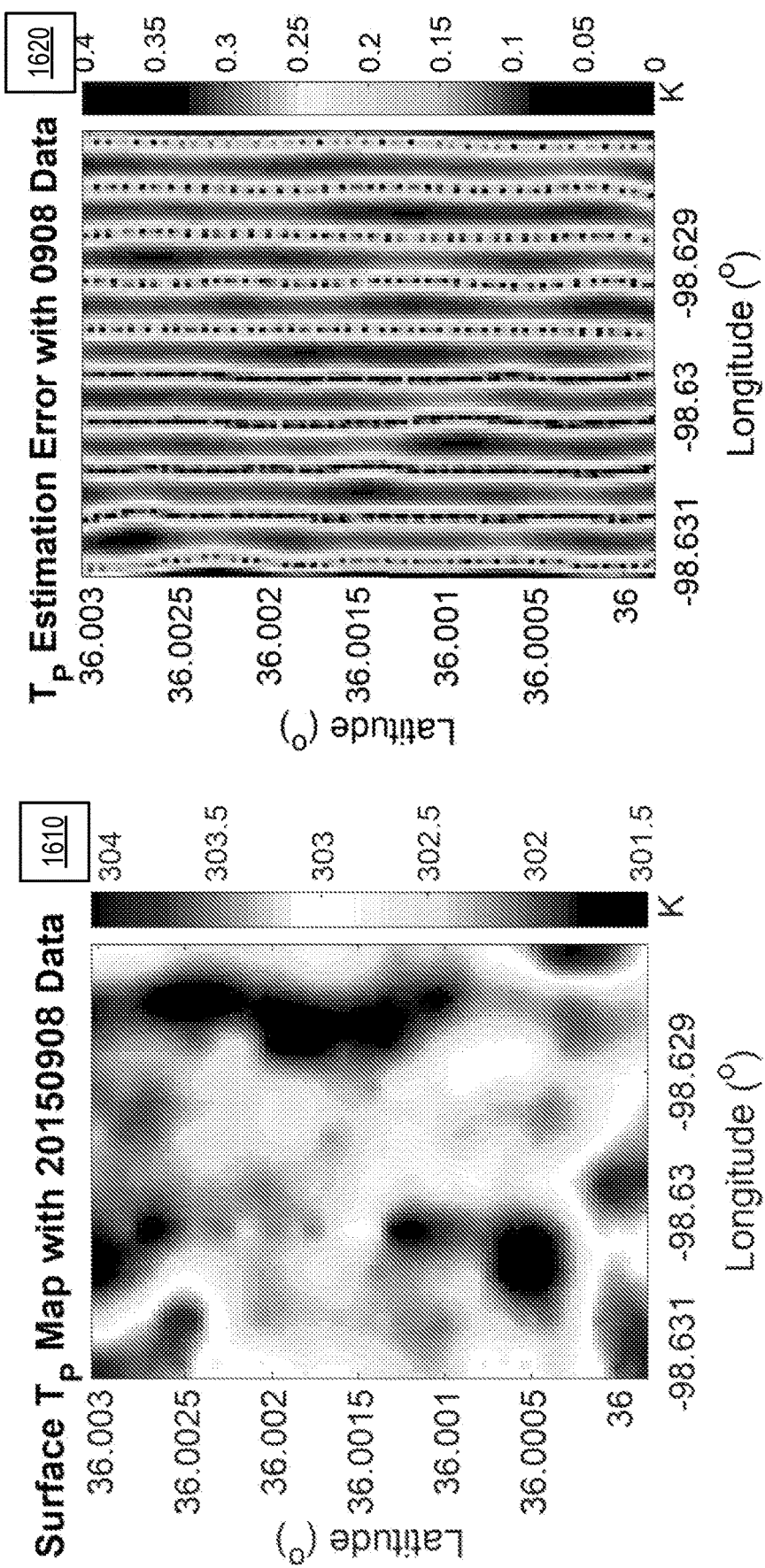
FIG. 16 shows maps of surface temperature and the estimation error in the measurements of the surveyed area of FIG. 15.

FIG. 16 shows maps 1610 and 1620 of surface temperature and the estimation error in the measurements of the surveyed area of FIG. 15 from the September $8^{th}$ flight. Map 1610 shows surface temperature $T_P$ measured by a down-looking infrared (IR) sensor onboard the LDCR. The surface temperature $T_P$ was calculated using the unbiased statistical LMMSE method with its estimation error shown in map 1620. Map 1620 shows the estimation error with a minimum error of ~0.13 K beneath the flight lines and a maximum error of ~0.32 K between flight lines. The measured surface temperature $T_P$ had a mean value of 302.9 K with standard deviation of 0.79 K during the mapping period of approximately 7 minutes.

For the September 9th data, the measured $T_P$ had a mean value of 292.9 K and a standard deviation of 0.16 K, and the $T_P$ estimation error has a similar spatial variation to the previous day; however, the values were lower by ~70% due to the lower overall $T_P$ standard deviation. Due to the short duration of each flight, a relatively small change in surface temperature between takeoff and landing was likely.

FIGS. 17 and 18 show maps 1710, 1720, 1810, and 1820 of measured VSM and the estimation error in the measurements of the surveyed area of FIG. 15. Maps 1710 and 1810 show LDCR retrieved VSM from the September $8^{th}$ and $9^{th}$ flights, respectively. Maps 1720 and 1820 show the estimation error in the retrieved VSM from the September $8^{th}$ and $9^{th}$ flights, respectively. The retrieved VSM shown in maps 1710 and 1810 was calculated using the full-domain algorithm from $T_A$ measurement on the flight sampling grid along with estimated $T_P$ maps (e.g., map 1610, FIG. 16). A uniform spatial correlation function was used in the retrieval process to describe the vegetation cover homogeneity in the mapping area. With the assumption that all parameters $\overline{P}$ are accurately known, the VSM estimation error standard deviations, shown in maps 1720 and 1820, were calculated and found to be mainly dependent on the $T_A$ estimation error and measurement locations of the airborne LDCR system. The minimum error was observed directly beneath flight lines to be ~3.5%-4% VSM, and the maximum error was ~5%-5.5% VSM at locations between flight lines.

Figure 19:
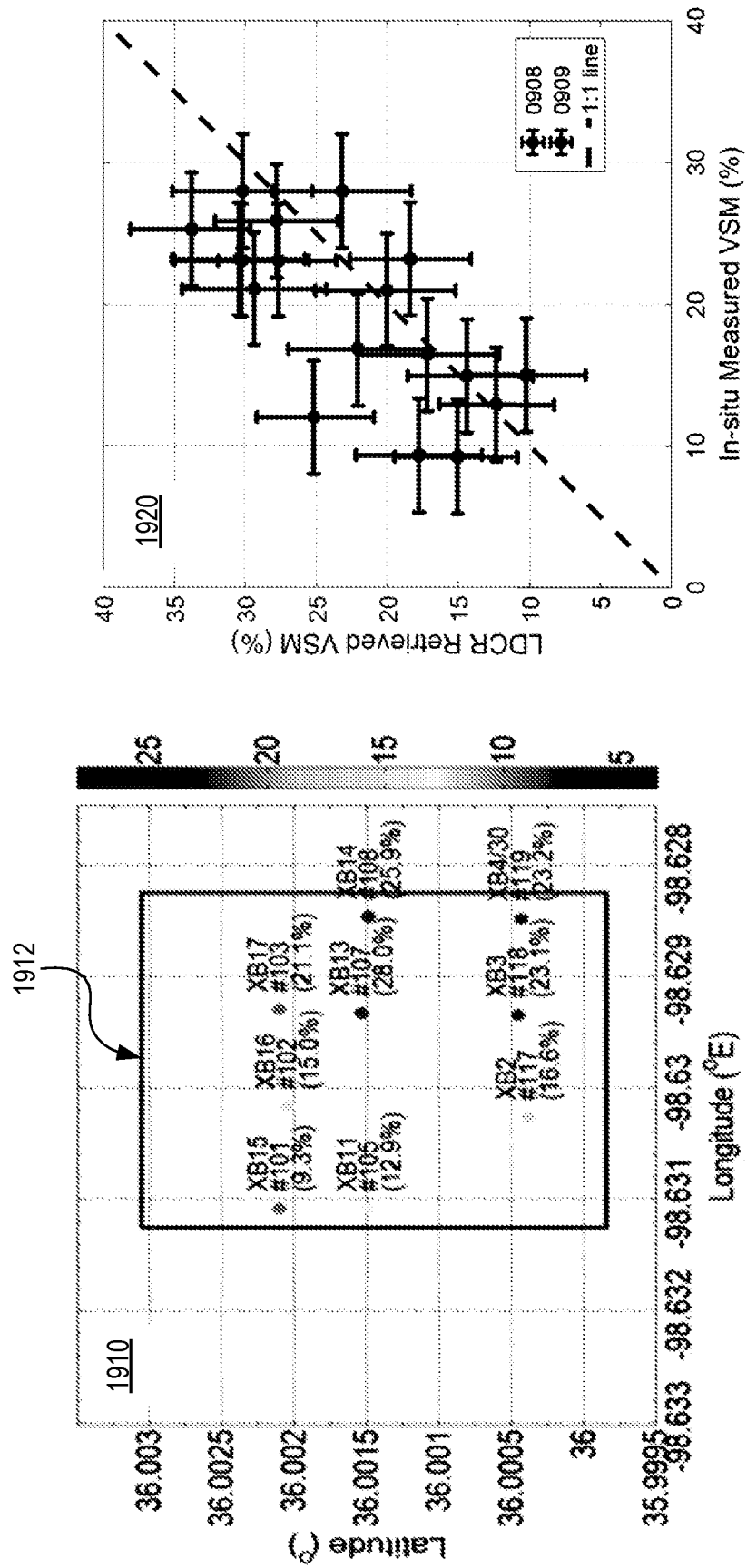
FIG. 19 shows plots of in situ volumetric soil moisture measurements and the locations those measurements, and comparison of those measurements to volumetric soil moisture measured from the surveyed area of FIG. 15.

FIG. 19 shows plots 1910 and 1920 of in situ VSM measurements and the locations those measurements, and comparison of those measurements to VSM measured from the surveyed area of FIG. 15. Plot 1910 includes a surveyed area 1912 where the UAS was flown. Plot 1920 shows the in situ VSM measurements at nine locations in surveyed area 1912. At each location, sensors were installed at three different depths, 5, 15, and 30 centimeters below the soil surface. The sensor measurement error was estimated to be 4%. The LDCR retrieved VSM values are compared with these measurements in plot 1920, where a correlation coefficient of 0.70 is obtained.

Field experiment in Yuma, Colorado

Figure 21:
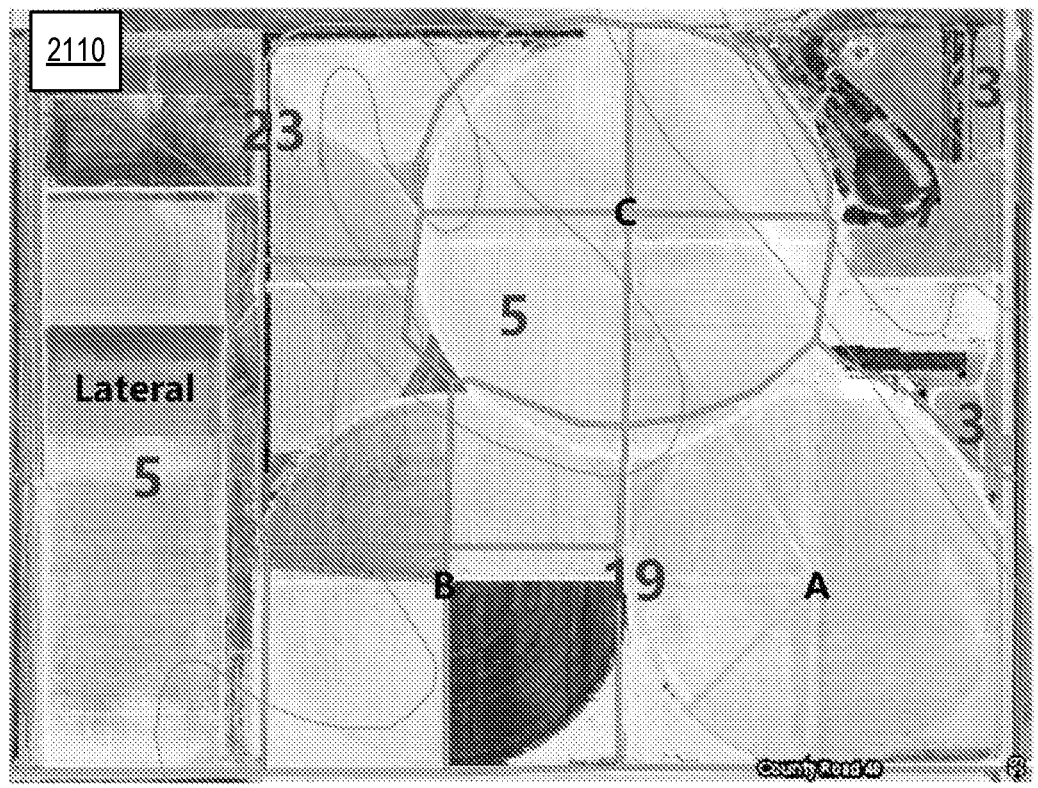
FIG. 21 shows a map and a table summarizing the soil types in the mapping area of FIG. 20.

Four successful field experiments were performed at the IRF site in Yuma, Colorado, the IRF site hereinafter, in 2016 with a Tempest UAS equipped with a LDCR Rev A. FIG. 20 shows maps 2010, 2020, and 2030 illustrating flight paths of an embodiment of airborne LDCR system 500 of FIG. 5, the land cover type, and vegetation water content of a mapping area at the IRF site. Map 2010 shows a mapping area 2012 and two flight paths 2014 and 2016. Flight path 2014 was flown in the NS direction between 12:19 P.M. to 12:34 P.M, and flight path 2016 was flown in east-west (EW) direction (10:46 A.M. to 11:06 A.M.) on June 14. Another flight with flight path 2016 in the EW direction took place between 12:50 P.M. to 13:07 P.M. on June 20, and the last flight with flight path 2014 in the NS direction was performed between 10:04 A.M. to 10:22 A.M. on June 23. Map 2020 shows the land cover types in mapping area 2012. The land cover types in mapping area 2012 included ten distinct vegetation covers including corn, soybean, wheat, grain sorghum, sugar beets, grass, standing water, trees, bare soil, and buildings. Map 2030 shows VWC derived from Landsat 7 ETM+ data for comparison. FIG. 21 shows a map 2110 and a table 2120 summarizing the soil types in the mapping area 2012 of FIG. 20. Soil types in mapping area 2012 are classified according to sand and clay percentage in table 2120.

Figure 22:
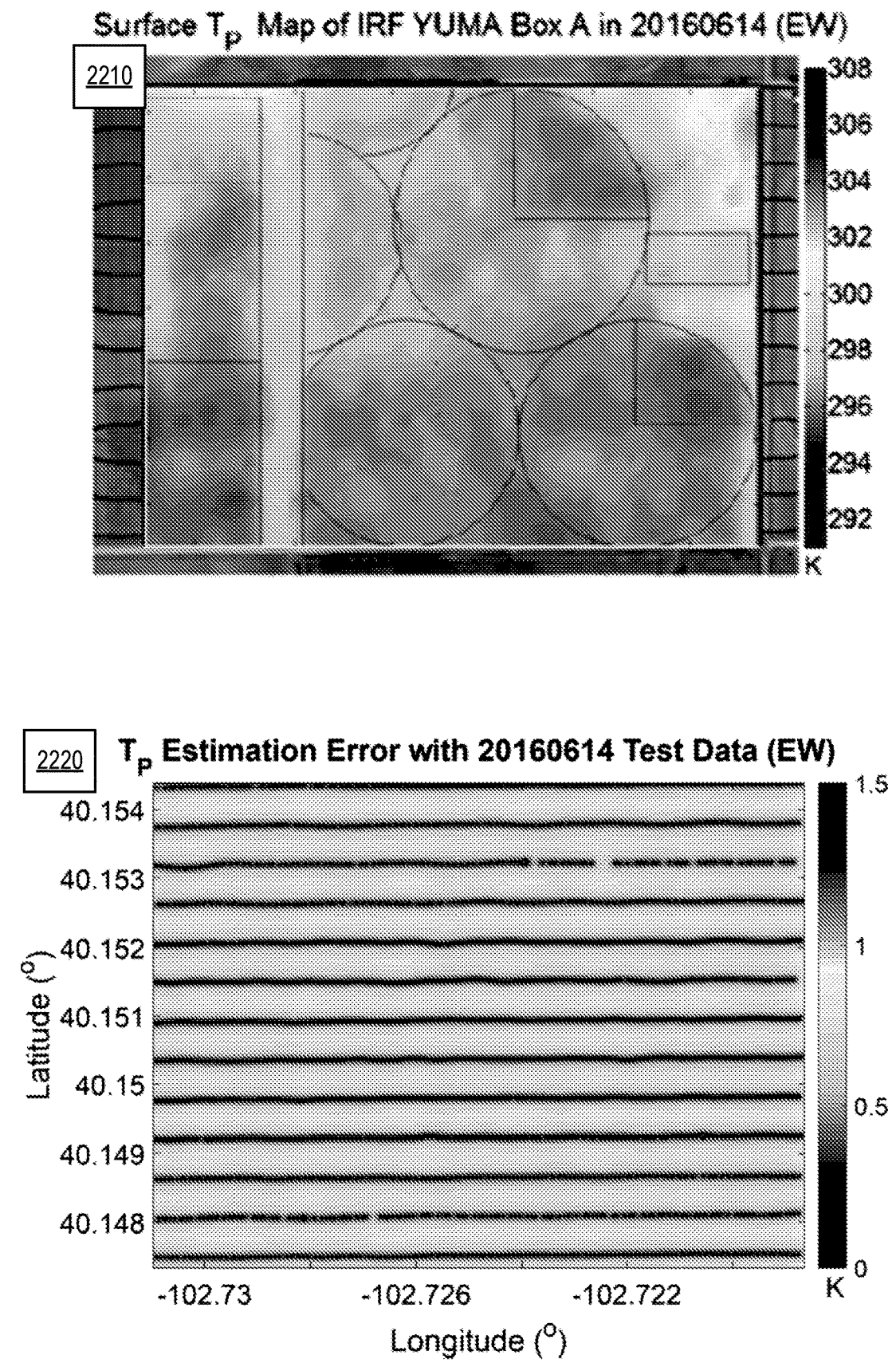

FIGS. 22 and 23 show maps 2210, 2220, 2310, and 2320 of surface temperature $T_P$ and the estimation error in the measurements of the mapping area 2012 of FIG. 20. Maps 2210 and 2310 show interpolated surface temperatures $T_P$ measured during the EW and NS flight paths, respectively. Maps 2220 and 2320 show the corresponding estimation error in the surface temperature measurements. Measurements for surface temperatures $T_P$ were taken in the two successive flights, the EW flight path followed by the NS flight path, on June 14. The two $T_P$ maps 2210 and 2310 are consistent. For examples, the measured $T_P$ for the noon (NS flight) shown in map 2310 is ~3 K higher than that in the morning (EW flight) shown in map 2210, while the surface $T_P$ for bare soil and grass areas is higher than that for cropland by ~5 K on both maps. The two $T_P$ estimation error maps show similar spatial variation associated with the location of flight lines, similar to map 1620 in FIG. 16. For flights on June 20 and 23, $T_P$ show higher values at bare soil and its estimation error show similar spatial variation. In all cases, the $T_P$ error does not dominate the $T_A$ error.

FIG. 24 shows maps 2410, 2412, 2414, 2420, 2422, and 2424 of VSM retrieved from the mapping area 2012 of FIG. 20 using two different functions in the algorithm 800 of FIG. 8. Maps 2410 and 2420 show VSM retrieved on June $14^{th}$; maps 2412 and 2422 show VSM retrieved on June $20^{th}$; and maps 2414 and 2424 show VSM retrieved on June $23^{rd}$. VSM maps were retrieved using the full-domain LMMSE estimation method and the user-defined mapping grid size is ~5×5 meters. For the vegetation cover complexity and land management practices in this mapping area, both land section covariance (LSC) function, results of which are shown in maps 2410, 2412, and 2414, and uniform correlation LSC (UCLSC) function, with results shown in maps 2420, 2422, and 2424, are used in this retrieval process. For the June 14th flights, the LDCR VSM are retrieved by combining both EW and NS flight data, and for June $20^{th}$ and $23^{rd}$ data, the VSM are retrieved from single flight direction data. As expected, the retrieved VSM using the LSC function, shown in maps 2410, 2412, and 2414, exhibit more detail in each land usage section while the VSM retrieved using the UCLSC function, shown in maps 2420, 2422, and 2424, exhibit a uniform value in each section.

Figure 25:
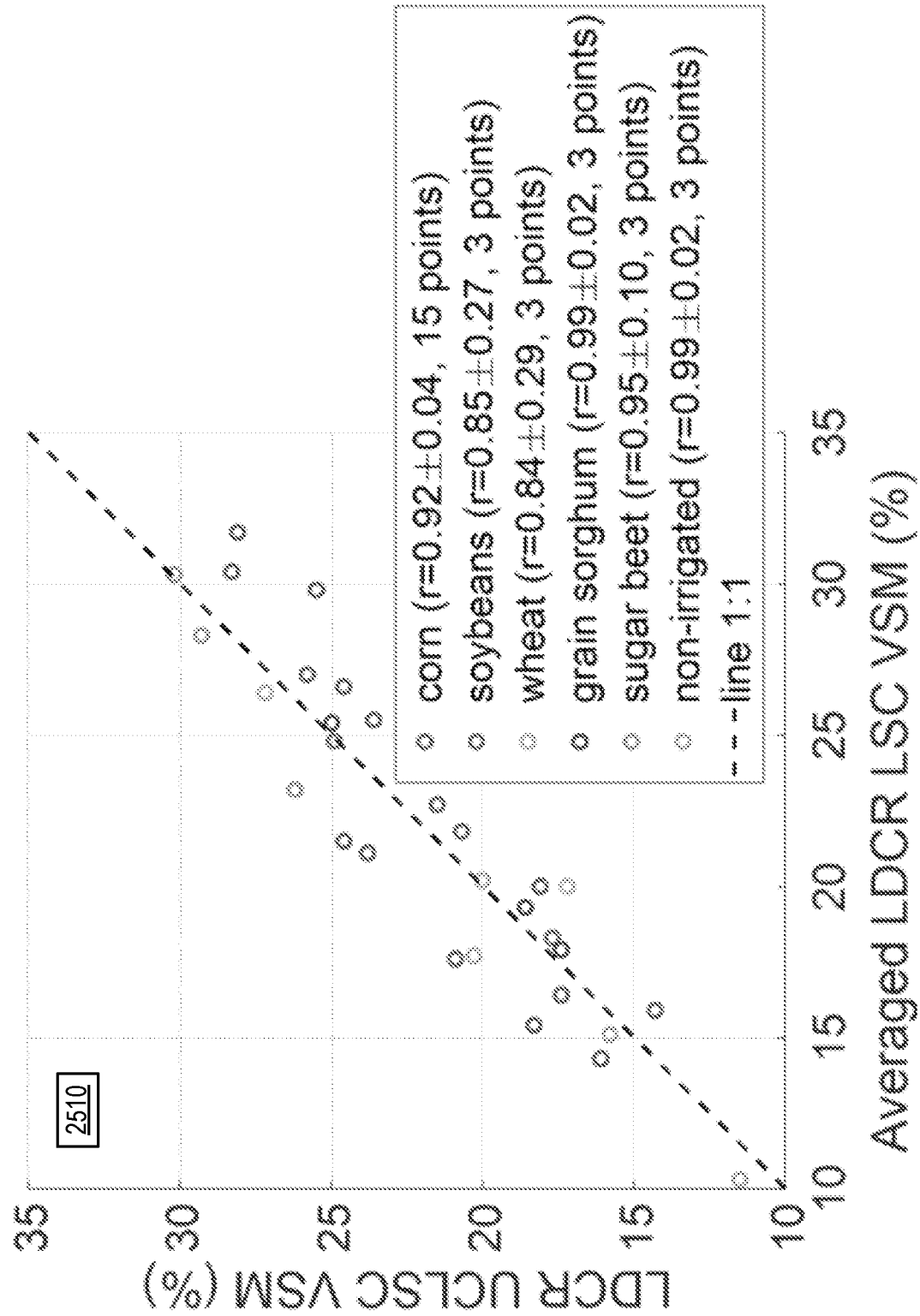
FIG. 25 shows a plot comparing the results from using two different functions of FIG. 24.

FIG. 25 shows a plot 2510 comparing the results from using two different functions of FIG. 24. Plot 2510 shows a high correlation between the two functions, LSC and UCLSC, with a correlation coefficient of 0.93±0.03 for all vegetation cover. Correlations for individual crop types are similarly high, although the number of samples available is small. The UCLSC function is based on the assumption that the VSM within each land section has a unity correlation coefficient. The reason for this assumption primarily depends on the land section size, soil texture homogeneity, and soil topography within the land section. UCLSC is anticipated to be useful in precision irrigation due to its weighted averaging of all available measurements over a section.

Figure 26:
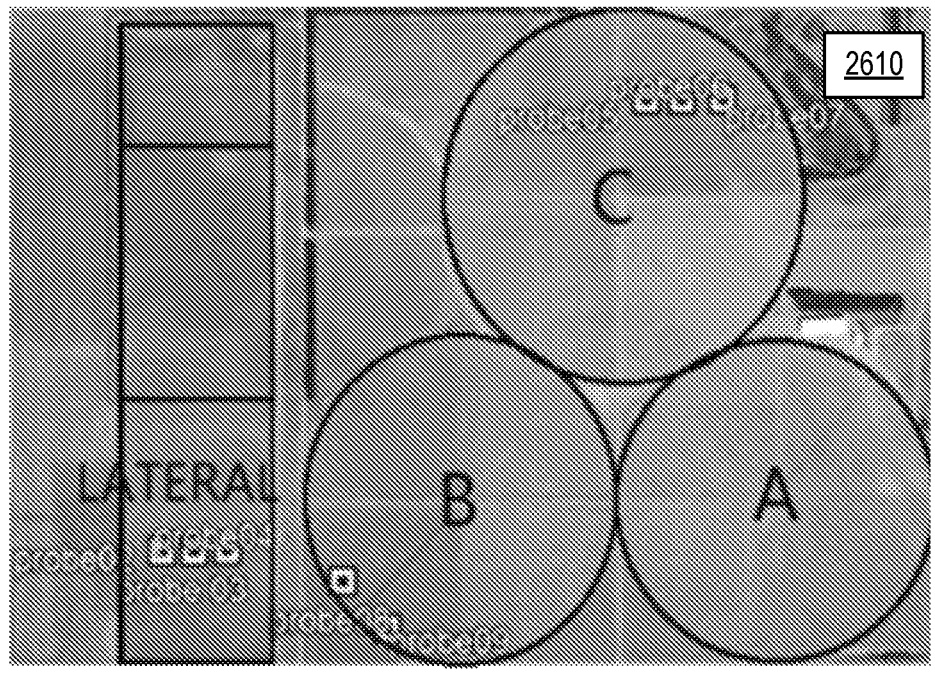
FIGS. 26 and 27 show in situ volumetric soil moisture data of the mapping area of FIG. 20, supplied by the Irrigation Research Foundation, for comparison.
Figure 27:
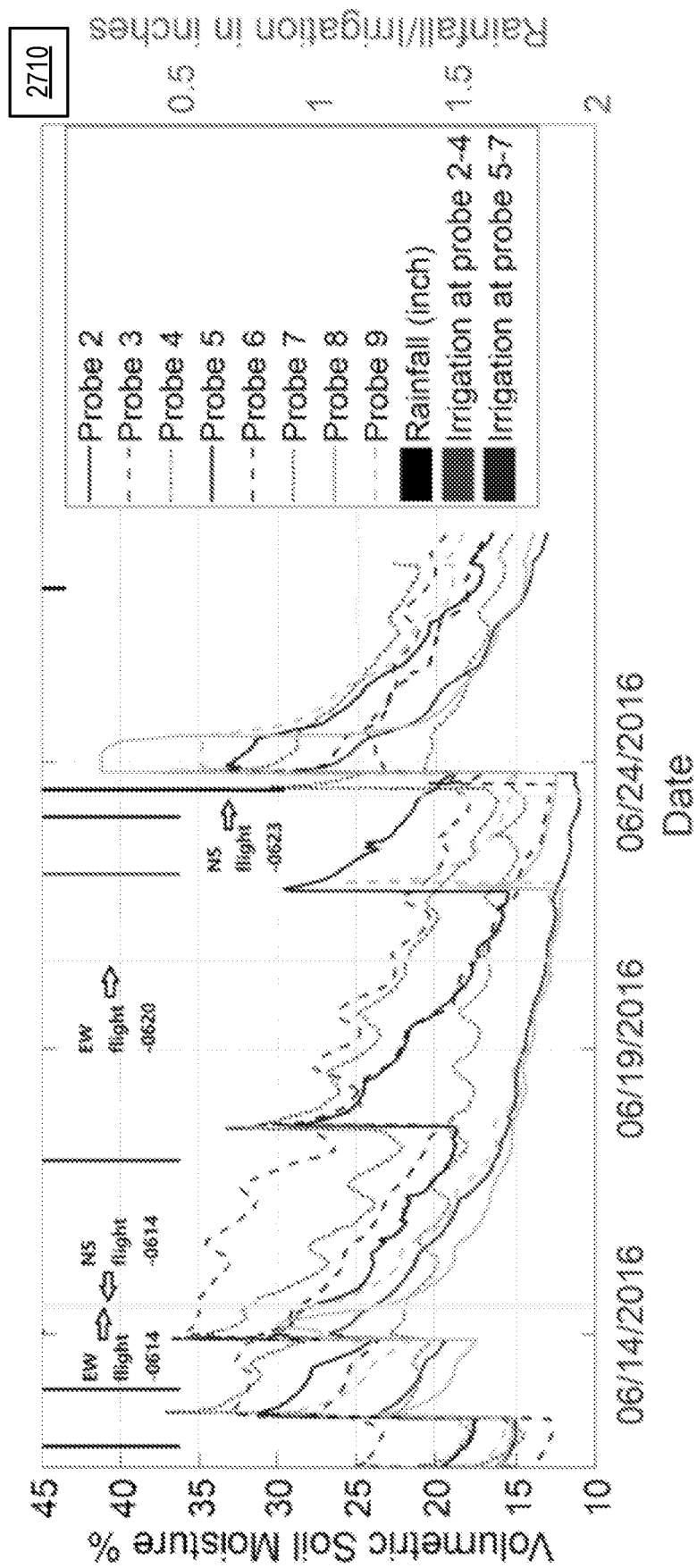

FIGS. 26 and 27 show in situ VSM data of the mapping area 2012 of FIG. 20, supplied by the Irrigation Research Foundation, for comparison. Map 2610 in FIG. 26 shows the locations of eight probes in the mapping area. Table 2620 shows the in situ VSM measured by each probe for the three days of UAS flight. Probes 8 and 9 are within the corn sector of circle B; probes 2 to 4 are within the soybeans portion of the lateral area; and probes 5 to 7 are within the sugar beet sector of circle C. Sensors at different depths, 10, 20, and 30 centimeters, at each probe location recorded data every 15 minutes. Plot 2710 shows historical in situ VSM data for each probe, along with irrigation and precipitation data, around the days of UAS flight. The in situ VSM at 10 centimeters deep was found to be consistent with IRF irrigation records and precipitation data history during which no precipitation was recorded from June 14 to June 23.

Figure 28:
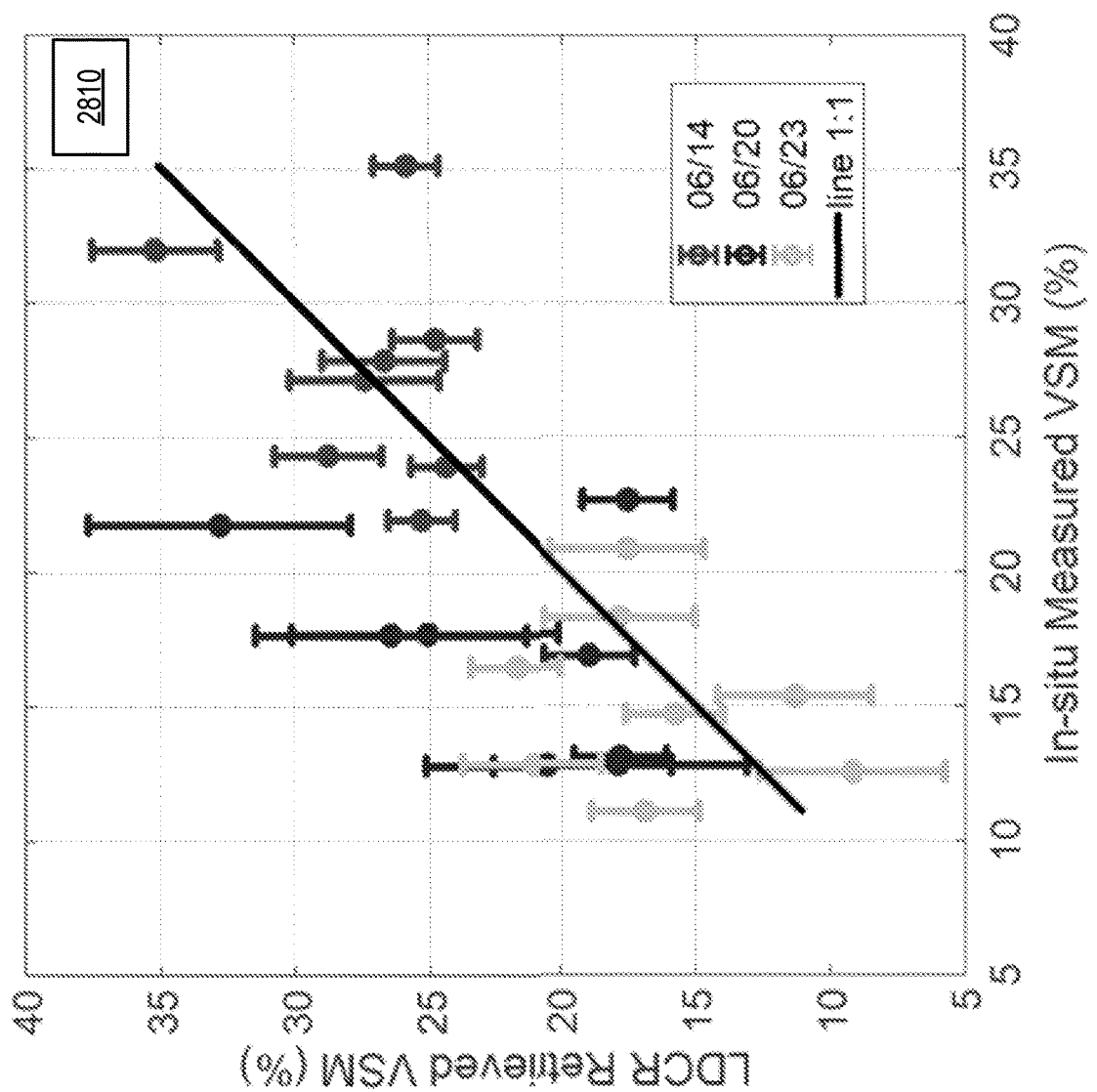
FIG. 28 is a plot comparing in situ data of FIG. 27 with calculated results using the algorithm of FIG. 8.

FIG. 28 is a plot 2810 comparing in situ data of FIG. 27 with calculated results using algorithm 800 of FIG. 8. The LDCR retrieved VSM was calculated using the LSC function, and in situ VSM data were provided from probes at 10 centimeters in depth. Plot 2810 shows correlation coefficient of 0.69 between the two sets of measurements.

FIG. 29 is a table 2910 showing calculated VSM for each section of the mapping area 2012 of FIG. 20 using two different functions of FIG. 24. Each VSM data retrieved using the LSC function was averaged over each land usage section. From June 20 to June 23, table 2910 shows that the wheat in the lateral area became wetter by 6.4%-10% while the corn and soybeans in the lateral area dried by 2%-6.5%. These changes are consistent with irrigation of the wheat by 1 inch of water on June 17. Table 2910 also shows that the NE quarter of circle C (in map 2610, FIG. 26) became dry by 0.9%-2.0% while the other 3 quarters became dry by 1.9%-2.8%. These changes are also consistent with irrigation of only the NE quarter of circle C by 0.5 in of water on June 17. Lastly, table 2910 shows that the NE quarter of circle A became dry by 6.1%-6.4% while the other three quarters became dry by 7.6%-8.6%. While these changes are also consistent with irrigation of only the NE quarter of circle A by 0.5 inches of water on June 17, the changes may also be due to a smaller water demand by the grain sorghum relative to that of the corn.

From June 20 to June 23, table 2910 indicates that the soybeans in the lateral section have approximately the same soil moisture while the wheat and corn became dry by ~8%. These changes are consistent with irrigation of the soybeans by 0.5 inches of water on June 22. In circle B, the north half became wetter by 5.2%-9.5% while the south half dried by 0.7%-3.6%. These changes are consistent with irrigation of the north half by 0.5 in of water on June 21. In some cases, reduction in averaged moisture is sometimes observed after an irrigation event. These reductions may have been caused by the water demand of specific crops.

Figure 30:
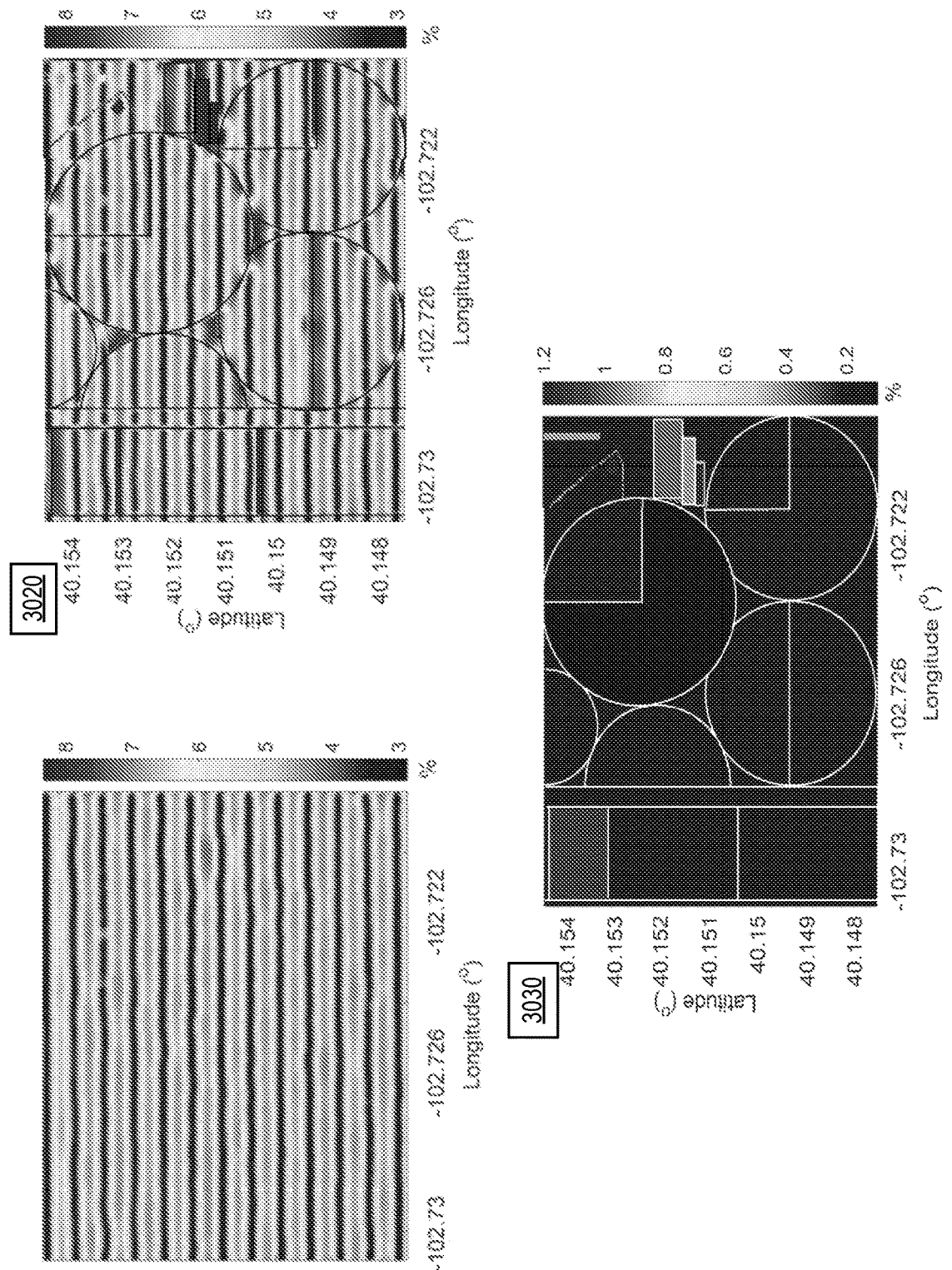
FIG. 30 shows maps of estimation error in the data shown in FIG. 29 from one east-west flight shown in FIG. 20 using three different spatial covariance functions in the algorithm of FIG. 8.

FIG. 30 shows maps 3010, 3020, and 3030 of estimation error in the data shown in FIG. 29 from one east-west flight shown in FIG. 20 using three different spatial covariance functions in algorithm 800 of FIG. 8. Map 3010 shows VSM estimation error using a uniform spatial covariance function, while maps 3020 and 3030 show the error when using the LSC function and the UCLSC function, respectively. The VSM data is from the EW flight on June 14 and is used in the estimation error analysis below. Map 3020 shows that for VSM retrieval using the LSC function, the estimation errors at the boundaries between different land sections are increased by ~1%-2% VSM compared with the estimation errors provided by a uniform spatial covariance function shown in map 3010. These increases near boundaries are due effectively to a reduction of the data volume of the relevant set of observations at land section boundaries. For VSM retrieval using the UCLSC function, shown in map 3030, the estimation error has a uniform value within each managed land section. This estimation error is mostly below ~0.2%. This low value is a result of the weighted averaging of all available observations over each of the 31 identified land usage sections. The number of spatially independent antenna temperature measurements within each land usage section varies from ~15 to ~250 and results in a considerable increase in effective integration time relative to that of the LSC and the uniform spatial covariance methods.

Figure 31:
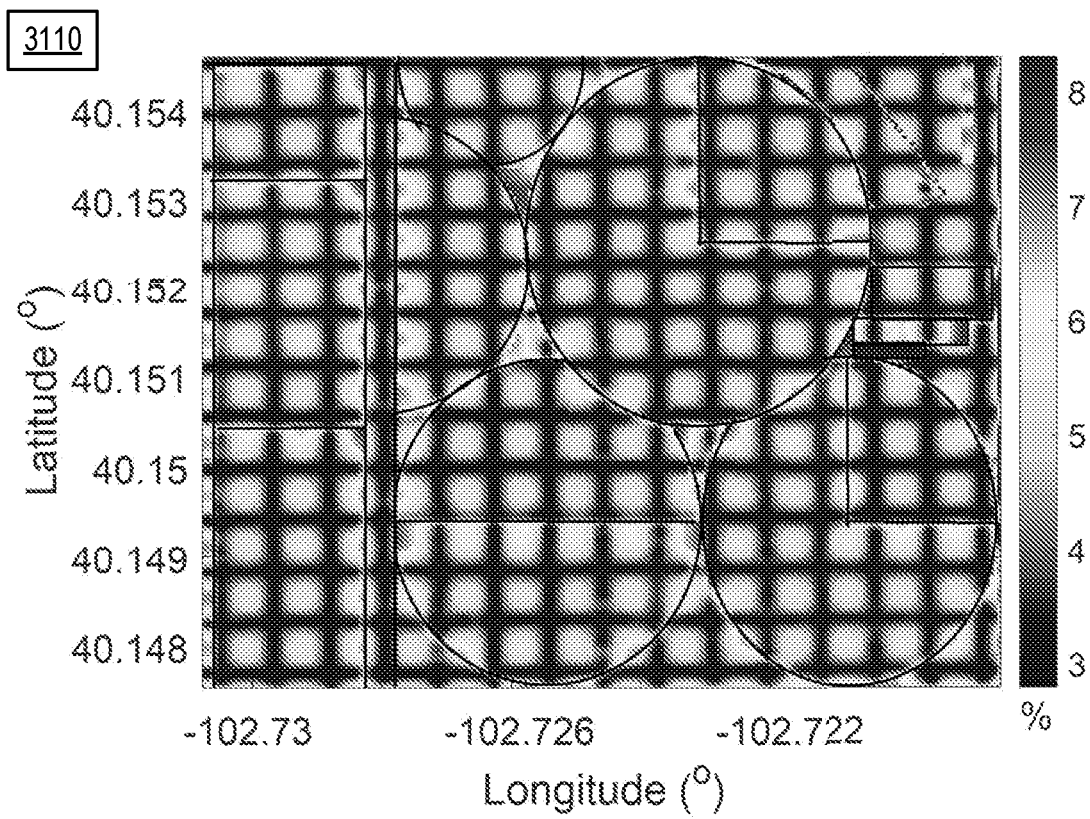
FIG. 31 is a map of estimation error in the data shown in FIG. 29 when combining one east-west flight data with one north-south flight data.

FIG. 31 is a map 3110 of estimation error in the data shown in table 2910 in FIG. 29 when combining one east-west flight data with one north-south flight data. By combining of the EW and NS flight data, the estimation error is decreased as shown in map 3110 when compared to maps 3010, 3020, and 3030. The minimum error is ~3% beneath the intersection of the orthogonal flight lines, and maximum error is ~5.5% between neighboring flight lines while the maximum estimation error between flight lines is ~6.5%-7.5% with EW flight data only. The minimum VSM error is approximately equal to the value of sensor $\Delta T_{rms,s}$ propagated using a nominal 1 K/% $T_A$ response to VSM.

FIG. 32 is a table 3210 showing the estimation error in the data shown in FIG. 29. The VSM estimation error in table 3210 accounts for uncertainties in integration, parameters, and estimation operator nonlinearity for corn, wheat, and soybeans from the data collected at the IRF site. For purpose of illustration, the error bias and variance of each parameter were set to be identical for all vegetation types. In an embodiment, the VWC estimation bias and covariance used is 0.2 kg/m², and the $T_P$ bias error and variance used is 5 K. In addition, sand and clay bias percentage error and variance were set to 5%. Table 3210 compares, for each vegetation type, estimation error for both beneath the flight lines and in-between flight lines. Among all parameters, the estimation bias in VWC W, has the largest impact on the VSM estimation error, and $T_P$ bias has the second largest impact. For the vegetation correction parameters, $b_h$ has a larger impact than $b_v$ which is consistent with higher attenuation at horizontal polarization from vegetation layers. Biases contribute larger errors than their associated variances for all geophysical measurements. The total estimation error is increased by these systematic uncertainties by ~2% VSM beneath the flight lines and ~0.5% between the flight lines.

To summarize the experimental demonstration, an aerial system, such as an airborne LDCR system 500 of FIG. 5, comprising a version of LDCR, LDCR Rev. A, and an UAS, a Tempest aircraft modified by Black Swift Technologies LLC, was field tested for high spatial resolution soil moisture mapping experiments. Calibration was performed to determine the LDCR sensitivities and offset. The sensitivities and offset voltage thermal drift induced by the analog correlator chip self-heating was determined and compensated. Noise interference from the UAS platform was observed and effectively mitigated by electromagnetic shielding. Six combined successful field experiments were performed in 2015 and 2016 at the Canton site and the IRF site. The LDCR surface physical temperature $T_P$ and antenna temperature $T_A$ were measured on the UAS sampling grid. The retrieved LDCR soil moisture maps agreed with in situ VSM measurements and irrigation records.

A linearized observation operator for the LDCR antenna temperature observed on an arbitrary UAS sampling grid due to VSM values on a user-defined mapping grid was determined. The LDCR VSM error covariance was determined using a physical LMMSE estimation method. The VSM estimation error was found to be primarily dependent on radiometer $\Delta T_{rms,s}$ and flight line separation. The vegetation correction was also critical to improve the LDCR VSM estimation accuracy.

Figure 33:
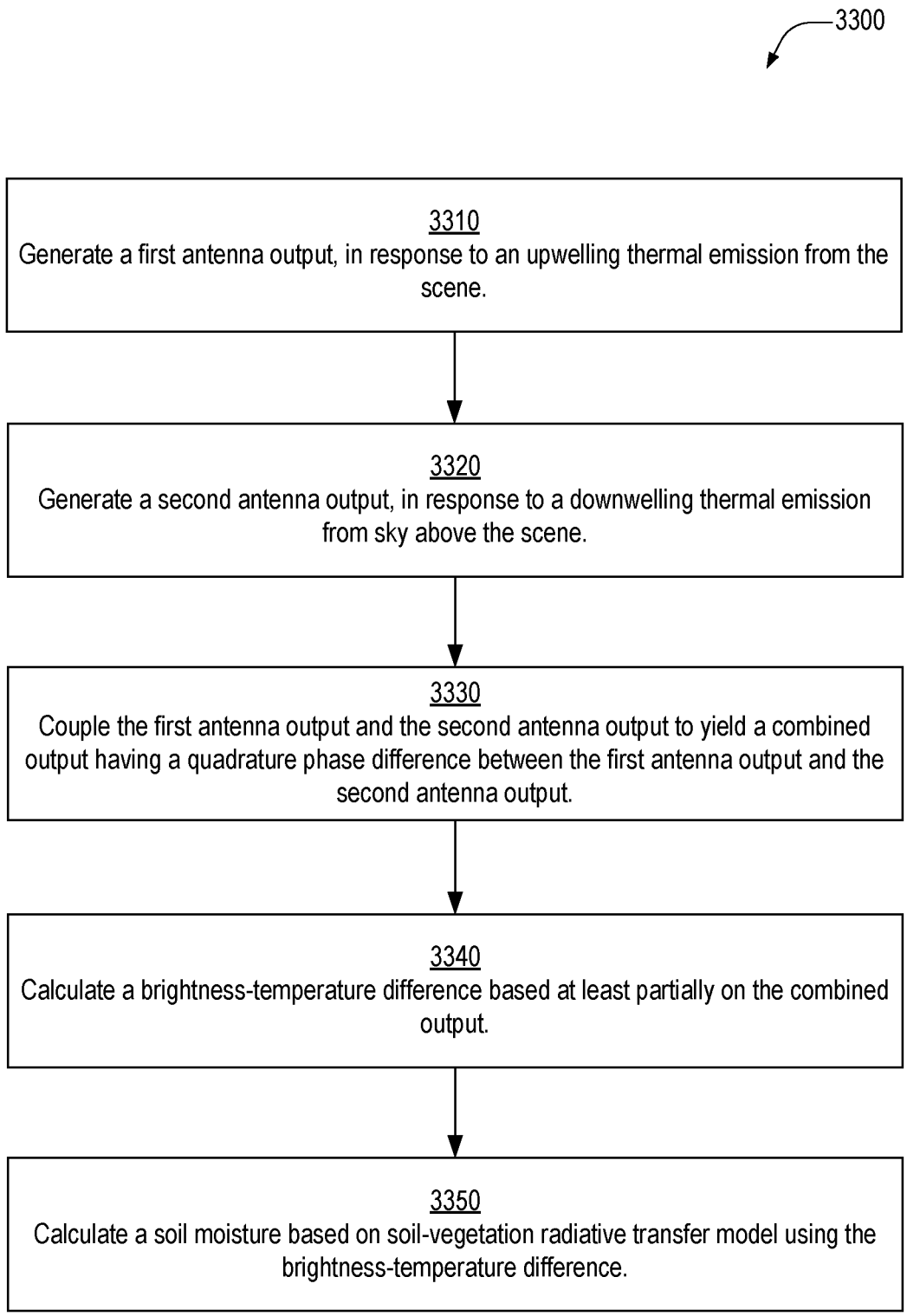
FIG. 33 is a flowchart illustrating a method for determining soil moisture of a scene, in an embodiment.

FIG. 33 is a flowchart illustrating a method 3300 for determining soil moisture of a scene. Method 3300 may be implemented in part or fully by radiometer 100 or airborne LDCR system 500. Method 3300 includes steps 3310, 3320, 3330, 3340, and 3350.

Step 3310 includes generating a first antenna output, in response to an upwelling thermal emission from a scene. The first passive microwave antenna has a nadir-pointing main lobe. In an example step 3310, antenna 212 in FIG. 2A generates a first antenna output in response to an upwelling thermal emission, that may include, as shown in FIG. 9, (1) the upwelling vegetation emission, (2) upwelling soil emission attenuated by the vegetation canopy, (3) the downwelling canopy and sky emission reflected by the soil and attenuated by the canopy layer, and (4) the downwelling sky emission reflected by the canopy layer.

Step 3320 includes generating a second antenna output, in response to a downwelling thermal emission from sky above the scene. The second passive microwave antenna has a zenith-pointing main lobe and is vertically separated from the first passive microwave antenna by a quarter of a resonant wavelength of the second passive microwave antenna. In an example step 3320, antenna 202 in FIG. 2A generates a second antenna output based on the well-known downwelling brightness temperature of cold space.

Step 3330 includes coupling the first antenna output and the second antenna output to yield a combined output having a quadrature phase difference between the first antenna output and the second antenna output. In an example of step 3330, signal coupler 220 in FIG. 2B couples respective outputs of antennas 202 and 212 to yield a combined output voltage 232. In an embodiment, the quadrature phase difference is achieved by (i) having the first and the second passive microwave antennas vertically separated by a quarter of the resonant wavelength of the antennas, and (ii) coupling the first and the second antenna output with a quadrature coupler.

Step 3340 includes calculating a brightness-temperature difference based at least partially on the combined output of step 3330. In an example of step 3340, processor 1470 in FIG. 14 calculates, based on correlator output 1432, a brightness-temperature difference.

Step 3350 includes calculating a soil moisture based on SRVT model using the brightness-temperature difference of step 3340. In an example of step 3350, processing circuitry 140 in FIG. 1 calculates a soil moisture measurement 142 from the combined output of step 3340 using at least SVRT model 1442 of FIG. 14. The SVRT model 1442 includes contributions from at least: (i) composition of thermal emission observed in the upwelling brightness temperature of the scene, (ii) dielectric mixing model, which ties the observed brightness temperature to soil moisture, and (iii) correction from at least surface roughness.

Advantageously, using a similar approach of using dielectric mixing model, LDCR (e.g., LDCR 200) may be used to determine salinity of a body of water. In salt water, due to the increase in conductivity from increased salt content in water, the imaginary part of permittivity increases.

Combinations of Features

Features described above as well as those claimed below may be combined in various ways without departing from the scope hereof. The following enumerated examples illustrate some possible, non-limiting combinations.

(A1) A method for determining soil moisture of a scene includes (i) generating a first antenna output in response to an upwelling thermal emission from the scene, (ii) generating a second antenna output in response to a downwelling thermal emission from sky above the scene, (iii) coupling the first antenna output and the second antenna output to yield a combined output having a quadrature phase difference between the first antenna output and the second antenna output, (iv) calculating a brightness-temperature difference based at least partially on the combined output, and (v) calculating a soil moisture based on soil-vegetation radiative transfer model using the brightness-temperature difference. The first microwave antenna has a nadir-pointing main lobe. The second microwave antenna has a zenith-pointing main lobe and is vertically separated from the first microwave antenna by a quarter of the resonant wavelength of the second passive microwave antenna.

(A2) In embodiment of method (A1), a resonant wavelength of the first and the second passive microwave antennas is in the L-band.

(A3) In embodiments of either of the methods (A1) and (A2), said coupling further includes coupling the first and the second antenna outputs with a quadrature coupler.

(A4) In embodiments of any of the methods (A1)-(A3), the method further includes, when the first and the second passive microwave antennas are part of a radiometer, calibrating the radiometer by (i) measuring a first calibration source output of a first calibration source, (ii) measuring a second calibration source output of a second calibration source, and (iii) calculating an offset and a drift in the radiometer based on at least a difference between the first and the second calibration source outputs.

(A5) In embodiments of method (A4), said calibrating the radiometer further includes, prior to calibrating, setting temperatures of the first and the second calibration sources to a first calibration temperature and a second calibration temperature, respectively.

(B1) A radiometer for determining soil moisture of a scene includes a first passive microwave antenna, a second passive microwave antenna, a quadrature coupler, and a signal correlator. The first passive microwave antenna has a nadir-pointing main lobe. The second passive microwave antenna has a zenith-pointing main lobe, and is vertically separated from the first passive microwave antenna by a quarter of a resonant wavelength of the second passive microwave antenna. The quadrature coupler has a first input connected to an output of the first passive microwave antenna and a second input connected to an output of the second passive microwave antenna. The signal correlator is coupled to an output of the quadrature coupler, and outputs a correlator voltage linearly related to a difference between the first and the second inputs of the quadrature coupler.

(B2) In embodiments of the radiometer (B1), the first and the second passive microwave antennas are microstrip collinear antennas.

(B3) Embodiments of either of the radiometers (B1) and (B2), further include a first calibration source, a second calibration source, a first switch, and a second switch. The first switch has input contacts connected to the first calibration source and the first passive microwave antenna, and an output contact connected to the first input of the quadrature coupler. The second switch has input contacts connected to the second calibration source and the second passive microwave antenna, and an output contact connected to the second input of the quadrature coupler.

(B4) Embodiments of the radiometer (B3), further include a control circuitry coupled to the first and the second switches that, upon receiving instructions to select an operating mode, controls the first and the second switches to connect one of a plurality of input pairs to the quadrature coupler. The plurality of input pairs includes (i) the first calibration source and the second calibration source, (ii) the first calibration source and the second passive microwave antenna, (iii) the first passive microwave antenna and the second calibration source, and (iv) the first passive microwave antenna and the second passive microwave antenna.

(B5) Embodiments of the radiometer (B4), further include a processing circuitry, coupled to the output of the signal correlator. The processing circuitry includes a processor and a memory. The memory stores instructions that, when executed by the processor, control the processor to execute a plurality of steps including: (i) controlling the control circuitry to select the operating mode, and (ii) calculating soil moisture based on soil-vegetation radiative transfer model using the correlator voltage.

(B6) In embodiments of the radiometer (B5), the memory further stores instructions that, when executed by the processor, further control the processor to calculate a drift in the correlator voltage based on calibrated characteristics of the first and the second calibration sources.

(C1) An aerial system for determining soil moisture of a scene includes an aircraft and embodiments of the radiometer (B5). The radiometer is attached to a body of the aircraft.

(C2) In embodiments of the aerial system (C1), the processor, when further instructed to perform calibration, calculates a correction factor, based on the correlator voltage, for each of the plurality of input pairs when the scene has known soil moisture.

(C3) In embodiments of either of the aerial systems (C1) and (C2), the aircraft is an unmanned aircraft having a motor and a controller.

(C4) Embodiments of any of the aerial systems (C1)-(C3), further includes a sensor, configured to provide normalized difference vegetation index of the scene, communicatively coupled to the processor.

(C5) Embodiments of any of the aerial systems (C1)-(C4), further includes a sensor, configured to provide a surface elevation of the scene, communicatively coupled to the processor.

Changes may be made in the above methods and systems without departing from the scope of the present embodiments. It should thus be noted that the matter contained in the above description or shown in the accompanying drawings should be interpreted as illustrative and not in a limiting sense. Herein, and unless otherwise indicated the phrase "in embodiments" is equivalent to the phrase "in certain embodiments," and does not refer to all embodiments. The following claims are intended to cover all generic and specific features described herein, as well as all statements of the scope of the present method and system, which, as a matter of language, might be said to fall therebetween.

What is claimed is:

1. A method for determining soil moisture of a scene, comprising:
    generating a first antenna output, in response to an upwelling thermal emission from the scene, of a first passive microwave antenna that has a nadir-pointing main lobe;
    generating a second antenna output, in response to a downwelling thermal emission from sky above the scene, of a second passive microwave antenna has a zenith-pointing main lobe, the second passive microwave antenna being vertically separated from the first passive microwave antenna by a quarter of a resonant wavelength of the second passive microwave antenna;
    coupling the first antenna output and the second antenna output to yield a combined output having a quadrature phase difference between the first antenna output and the second antenna output;
    calculating a brightness-temperature difference based at least partially on the combined output; and
    calculating a soil moisture based on soil-vegetation radiative transfer model using the brightness-temperature difference.

2. The method of claim 1, wherein a resonant wavelength of the first and the second passive microwave antennas is in the L-band.

3. The method of claim 1, said coupling further includes coupling the first and the second antenna outputs with a quadrature coupler.

4. The method of claim 1, the first and the second passive microwave antennas being part of a radiometer, and further comprising calibrating the radiometer by:
    measuring a first calibration source output of a first calibration source;
    measuring a second calibration source output of a second calibration source; and
    calculating an offset and a drift in the radiometer based on at least a difference between the first and the second calibration source outputs.

5. The method of claim 4, calibrating the radiometer further comprising, prior to calibrating:
    setting temperatures of the first and the second calibration sources to a first calibration temperature and a second calibration temperature, respectively.

6. A radiometer for determining soil moisture of a scene, comprising:
    a first passive microwave antenna having a nadir-pointing main lobe;
    a second passive microwave antenna having a zenith-pointing main lobe, the second passive microwave antenna being vertically separated from the first passive microwave antenna by a quarter of a resonant wavelength of the second passive microwave antenna;
    a quadrature coupler having a first input connected to an output of the first passive microwave antenna and a second input connected to an output of the second passive microwave antenna; and
    a signal correlator coupled to an output of the quadrature coupler, that outputs a correlator voltage linearly related to a difference between the first and the second inputs of the quadrature coupler.

7. The radiometer of claim 6, wherein the first and the second passive microwave antennas are microstrip collinear antennas.

8. The radiometer of claim 6, further comprising:
    a first calibration source;
    a second calibration source;
    a first switch having input contacts connected to the first calibration source and the first passive microwave antenna, and an output contact connected to the first input of the quadrature coupler; and
    a second switch having input contacts connected to the second calibration source and the second passive microwave antenna, and an output contact connected to the second input of the quadrature coupler.

9. The radiometer of claim 8, further comprising:
    a control circuitry coupled to the first and the second switches that, upon receiving instructions to select an operating mode, controls the first and the second switches to connect one of a plurality of input pairs to the quadrature coupler;
    wherein the plurality of input pairs includes (i) the first calibration source and the second calibration source, (ii) the first calibration source and the second passive microwave antenna, (iii) the first passive microwave antenna and the second calibration source, and (iv) the first passive microwave antenna and the second passive microwave antenna.

10. The radiometer of claim 9, further comprising a processing circuitry, coupled to the output of the signal correlator, that includes:
a processor; and
a memory storing instructions that, when executed by the processor, control the processor to execute a plurality of steps including:
controlling the control circuitry to select the operating mode; and
calculating soil moisture based on soil-vegetation radiative transfer model using the correlator voltage.

11. The radiometer of claim 10, the memory further storing instructions that, when executed by the processor, further control the processor to calculate a drift in the correlator voltage based on calibrated characteristics of the first and the second calibration sources.

12. An aerial system for determining soil moisture of a scene, comprising:
an aircraft; and
the radiometer of claim 10, the radiometer being attached to the aircraft.

13. The aerial system of claim 12, further comprising instructions that, when executed by the processor, controls the processor to: calculate a correction factor, based on the correlator voltage, for each of the plurality of input pairs when the scene has known soil moisture.

14. The aerial system of claim 12, wherein the aircraft is an unmanned aircraft having a motor and a controller.

15. The aerial system of claim 12, further comprising a sensor, communicatively coupled to the processor, that provides a normalized difference vegetation index of the scene.

16. The aerial system of claim 12, further comprising a sensor, communicatively coupled to the processor, that provides a surface elevation of the scene.

* * * * *